United States Patent
Choi et al.

(10) Patent No.: US 12,331,364 B2
(45) Date of Patent: Jun. 17, 2025

(54) METHOD FOR DIAGNOSING CANCER AND PREDICTING TYPE OF CANCER BASED ON SINGLE NUCLEOTIDE VARIANT IN CELL-FREE DNA

(71) Applicant: GC GENOME CORPORATION, Gyeonggi-do (KR)

(72) Inventors: JungKyoon Choi, Daejeon (KR); Gyuhee Kim, Daejeon (KR); Eun Hae Cho, Gyeonggi-do (KR); Chang-Seok Ki, Gyeonggi-do (KR); Junnam Lee, Gyeonggi-do (KR)

(73) Assignee: GC GENOME CORPORATION, Yongin-si (KR)

( * ) Notice: Subject to any disclaimer, the term of this patent is extended or adjusted under 35 U.S.C. 154(b) by 0 days.

(21) Appl. No.: 18/169,750

(22) Filed: Feb. 15, 2023

(65) Prior Publication Data

US 2023/0407405 A1    Dec. 21, 2023

(30) Foreign Application Priority Data

Jun. 15, 2022    (KR) .................. 10-2022-0072680

(51) Int. Cl.
| | | |
|---|---|---|
| *C12Q 1/6886* | (2018.01) | |
| *G16B 20/20* | (2019.01) | |
| *G16B 30/10* | (2019.01) | |
| *G16B 40/00* | (2019.01) | |

(52) U.S. Cl.
CPC ........... *C12Q 1/6886* (2013.01); *G16B 20/20* (2019.02); *G16B 30/10* (2019.02); *G16B 40/00* (2019.02); *C12Q 2600/112* (2013.01); *C12Q 2600/156* (2013.01)

(58) Field of Classification Search
None
See application file for complete search history.

(56) References Cited

FOREIGN PATENT DOCUMENTS

| KR | 1020170144237 A | 10/2017 |
|---|---|---|
| KR | 1020170185041 B1 | 12/2017 |
| KR | 1020180124550 B1 | 10/2018 |

OTHER PUBLICATIONS

Huang et al. in Cancers (2019) vol. 11:15 pages.*
Danyi et al. (Life (2022) vol. 12:No. 1:20 pages).*
Alexandrov et al. (Nature (2013) vol. 500:415-421).*
Salvadores et al. (PLoS Computational Biology (2019) vol. 15(4):23 pages).*
Brownlee (Loss and Loss Functions for Training Deep Learning Neural Networks, Oct. 23, 2019 from Machine Learning Mastery. com; 19 pages).*
Chabon, J.J., et al., "Integrating genomic features for non-invasive early lung cancer detection", Nature, 2020, pp. 245-251; https://doi.org/10.1038/s41586-020-2140-0, vol. 580, Publisher: www.nature.com.
Cristiano, S., et al., "Genome-wide cell-free DNA fragmentation in patients with cancer", Nature, 2019, pp. 385-389, vol. 570, No. 7761, Publisher: www.nature.com/nature.
Jiao, W., et al., "A deep learning system accurately classifies primary and metastatic cancers using passenger mutation patterns", Nature Communications, 2020, https://doi.org/10.1038/s41467-019-13825-8, vol. 11, No. 728, Publisher: www.nature.com/naturecommunications.
Metzker, M.L., "Sequencing technlogies—the next generation", Nature Reviews/Genetics, 2010, pp. 31-46, vol. 11, Publisher: Macmillan Publishers Limited.
Zviran, A., et al., "Genome-wide cell-free DNA mutational integration enables ultra-sensitive cancer monitoring", Nature Medicine, 2020, pp. 1114-1124; https://doi.org/10.1038/s41591-020-0915-3, vol. 26, Publisher: www.nature.come/naturemedicine.

* cited by examiner

*Primary Examiner* — Lori A. Clow
(74) *Attorney, Agent, or Firm* — Knobbe, Martens, Olson & Bear, LLP

(57) ABSTRACT

Disclosed is a method of diagnosing cancer and predicting the type of cancer based on a single nucleotide variant in a cell-free nucleic acid including extracting nucleic acids from a biological sample to obtain sequence information, extracting cancer-specific single nucleotide variants through filtering based on aligned reads, calculating the regional mutation density of single nucleotide variants and the frequency of mutation signature of single nucleotide variants, and inputting the calculated values into a trained s: artificial intelligence model to analyze output values. This method is capable of exhibiting high sensitivity and accuracy compared to other methods of diagnosing cancer and predicting the type of cancer using genetic information of cell-free nucleic acids, and of ensuring the same level of sensitivity and accuracy as cancer-tissue-cell-based methods, and can be usefully applied to other analyses using single nucleotide variants in cell-free nucleic acids.

16 Claims, 8 Drawing Sheets

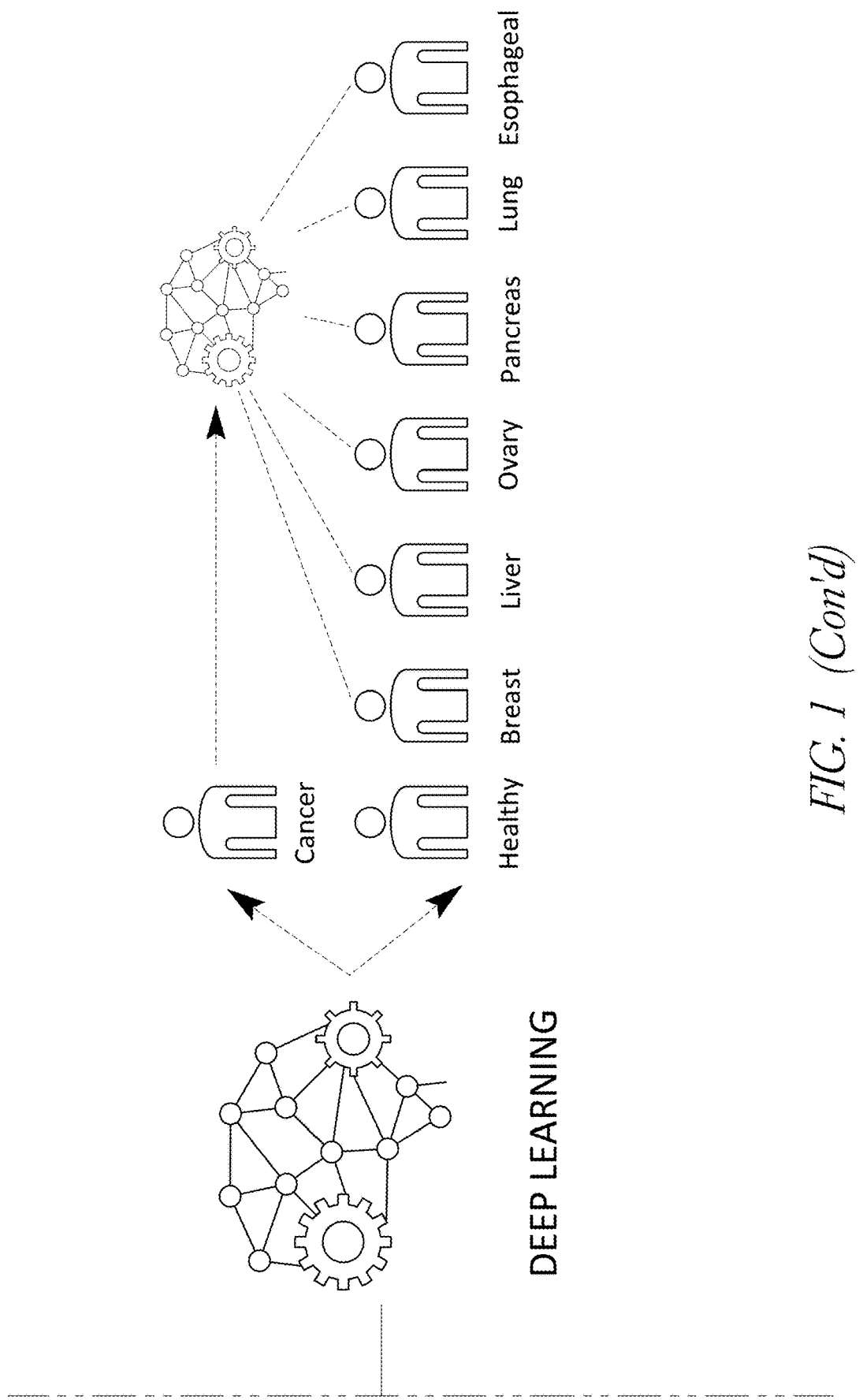
FIG. 1 (Con'd)

(A) Cancer detection (B) Tissue of origin

METHOD FOR DIAGNOSING CANCER AND PREDICTING TYPE OF CANCER BASED ON SINGLE NUCLEOTIDE VARIANT IN CELL-FREE DNA

CROSS-REFERENCE TO RELATED APPLICATION

The priority under 35 USC 119 of Korean Patent Application filed Jun. 15, 2022 is hereby claimed, and the disclosure thereof is hereby incorporated herein by reference in its entirety, for all purposes.

FIELD OF THE INVENTION

The present invention relates to a method of diagnosing cancer and predicting the type of cancer based on a single nucleotide variant in a cell-free nucleic acid, and more particularly to a method of diagnosing cancer and predicting the type of cancer based on a single nucleotide variant in a cell-free nucleic acid including extracting nucleic acids from a biological sample to obtain sequence information, extracting cancer-specific single nucleotide variants through filtering based on aligned reads, calculating the regional mutation density of single nucleotide variants and the frequency of mutation signature of single nucleotide variants, and inputting the calculated values into a trained artificial intelligence model to analyze output values.

DESCRIPTION OF THE RELATED ART

Cancer diagnosis in clinical practice is usually confirmed by performing tissue biopsy after health history examination, physical examination, and clinical evaluation. Cancer diagnosis by clinical trials is possible only when the number of cancer cells is 1 billion or more and the diameter of cancer is 1 cm or more. In this case, cancer cells already have metastasis capability, and at least half thereof have already metastasized. In addition, tissue biopsy is invasive, which causes considerable inconvenience to patients, and there are often cases in which tissue biopsy cannot be performed when treating cancer patients. In addition, although tumor markers for monitoring materials produced directly or indirectly from cancer are used in cancer screening, at least half of tumor marker screening results appear to be normal even in the presence of cancer, and often positive even in the absence of cancer, so there is a limit to the accuracy thereof.

Thorough research into diagnosing cancer through single nucleotide variant analysis of cell-free DNA is ongoing, and targeted sequencing of recurrent mutations frequently found in cancer by increasing sequencing depth has been mainly used (Chabon J. J. et al., *Nature*, Vol. 580, pp. 245-251, 2020). However, it has recently been found that sensitivity of examining more types of mutations using whole-genome sequencing (WGS) data of cell-free DNA is high even when the sequencing depth is low compared to targeted sequencing (Zviran A. et al., *Nat. Med.*, Vol. 26, pp. 1114-1124, 2020).

However, current technology is incapable of applying cell-free DNA WGS to cancer diagnosis because there is a problem with the accuracy of mutation detection in cell-free DNA WGS, and cell-free DNA WGS has been used only to monitor cancer recurrence by filtering and following-up the given mutation when patient's mutation information is provided through tumor tissue WGS (Zviran A. et al., *Nat. Med.*, Vol. 26, pp. 1114-1124, 2020). Specifically, it is effective to use cell-free DNA WGS for cancer diagnosis, but cell-free DNA WGS cannot be employed in cancer diagnosis due to the absence of an effective filtering method.

The mutation rate in cancer differs by region in the genome, and furthermore, the mechanism of mutation and the pattern of mutation accumulation vary depending on the type of cancer. Using these characteristics, it has been reported that it is possible to determine the type of cancer using regional mutation density and mutation signature in cancer tissue (Jia Wei et al., *Nat. Communications*, Vol. 11, No. 728, 2020). In this case, however, theoretical possibility is explored in the state that diagnosis of cancer and determination of the type of cancer have already been completed through surgery, and cell-free DNA WGS is not applied to cancer diagnosis technology.

Meanwhile, there are provided various patents (KR 10-2017-0185041, KR 10-2017-0144237, KR 10-2018-0124550) useful in life sciences using artificial neural networks, but methods of predicting the type of cancer by analyzing mutations based on sequencing information of cell-free DNA (cfDNA) WGS in blood are insufficient due to inaccuracy in the detection of cancer-specific mutations.

Accordingly, the present inventors have made great efforts to solve the above problems and to develop methods of diagnosing cancer and predicting the type of cancer with high sensitivity and accuracy based on single nucleotide variants in cell-free nucleic acids, and ascertained that, by extracting nucleic acids from a biological sample to obtain sequence information, extracting cancer-specific single nucleotide variants through filtering based on aligned reads, calculating the regional mutation density of single nucleotide variants and the frequency of mutation signature of single nucleotide variants, and inputting the calculated values into a trained artificial intelligence model to analyze output values, cancer may be diagnosed and the type of cancer may be predicted with high sensitivity and accuracy, thus culminating in the present invention.

SUMMARY OF THE INVENTION

It is an object of the present invention to provide a method of diagnosing cancer and predicting the type of cancer based on a single nucleotide variant in a cell-free nucleic acid.

It is another object of the present invention to provide an apparatus for diagnosing cancer and predicting the type of cancer based on a single nucleotide variant in a cell-free nucleic acid.

It is still another object of the present invention to provide a computer-readable storage medium including instructions configured to be executed by a processor for diagnosing cancer and predicting the type of cancer through the above method.

In order to accomplish the above objects, the present invention provides a method for diagnosing cancer and predicting a cancer type using a single nucleotide variant, including (a) extracting nucleic acids from a biological sample to obtain sequence information, (b) aligning the obtained sequence information (reads) to a reference genome database, (c) extracting cancer-specific single nucleotide variants by detecting single nucleotide variants in the aligned sequence information (reads) and performing filtering, (d) dividing the reference genome into predetermined bins and calculating the regional mutation density (RMD) of extracted single nucleotide variants in each bin, (e) calculating the frequency of mutation signature of the extracted single nucleotide variants, and (f) inputting the regional mutation density of single nucleotide variants calculated in step (d) and the frequency of mutation signature of single nucleotide variants calculated in step (e) into an artificial intelligence model trained to perform cancer diagnosis and comparing an output value with a reference value.

In addition, the present invention provides an apparatus for diagnosing cancer and predicting the type of cancer based on artificial intelligence, including a decoding unit configured to decode sequence information by extracting nucleic acids from a biological sample, an alignment unit configured to align the decoded sequence to a reference genome database, a mutation detection unit configured to extract cancer-specific single nucleotide variants by detecting single nucleotide variants in the aligned sequence and performing filtering, a single nucleotide variant distribution calculation unit configured to divide a reference genome into predetermined bins and calculate the regional mutation density of extracted single nucleotide variants in each bin, a mutation frequency calculation unit configured to calculate the frequency of mutation signature of the extracted single nucleotide variants, a cancer diagnosis unit configured to determine whether cancer is present or not by inputting the calculated regional mutation density of single nucleotide variants and the calculated mutation frequency thereof into an artificial intelligence model trained to perform cancer diagnosis and comparing an output value with a reference value, and a cancer-type prediction unit configured to predict the type of cancer by inputting the regional mutation density of single nucleotide variants of the sample determined to be cancer and the mutation frequency thereof to a second artificial intelligence model trained to classify types of cancer and comparing output values.

In addition, the present invention provides a computer-readable storage medium including instructions configured to be executed by a processor for diagnosing cancer and predicting the type of cancer, by (a) extracting nucleic acids from a biological sample to obtain sequence information, (b) aligning the obtained sequence information (reads) to a reference genome database, (c) extracting cancer-specific single nucleotide variants by detecting single nucleotide variants in the aligned sequence information (reads) and performing filtering, (d) dividing the reference genome into predetermined bins and calculating the regional mutation density of extracted single nucleotide variants in each bin, (e) calculating the frequency of mutation signature of the extracted single nucleotide variants, (f) determining whether cancer is present or not by inputting the regional mutation density of single nucleotide variants calculated in step (d) and the frequency of mutation signature of single nucleotide variants calculated in step (e) into an artificial intelligence model trained to perform cancer diagnosis and comparing an output value with a reference value, and (g) predicting the type of cancer by inputting the regional mutation density of single nucleotide variants and the frequency of mutation signature of single nucleotide variants of the sample determined to be cancer in step (f) into a second artificial intelligence model trained to classify types of cancer and comparing output values.

BRIEF DESCRIPTION OF THE DRAWINGS

The above and other objects, features, and other advantages of the present invention will be more clearly understood from the following detailed description taken in conjunction with the accompanying drawings, in which.

DETAILED DESCRIPTION OF THE INVENTION

Figure 1:
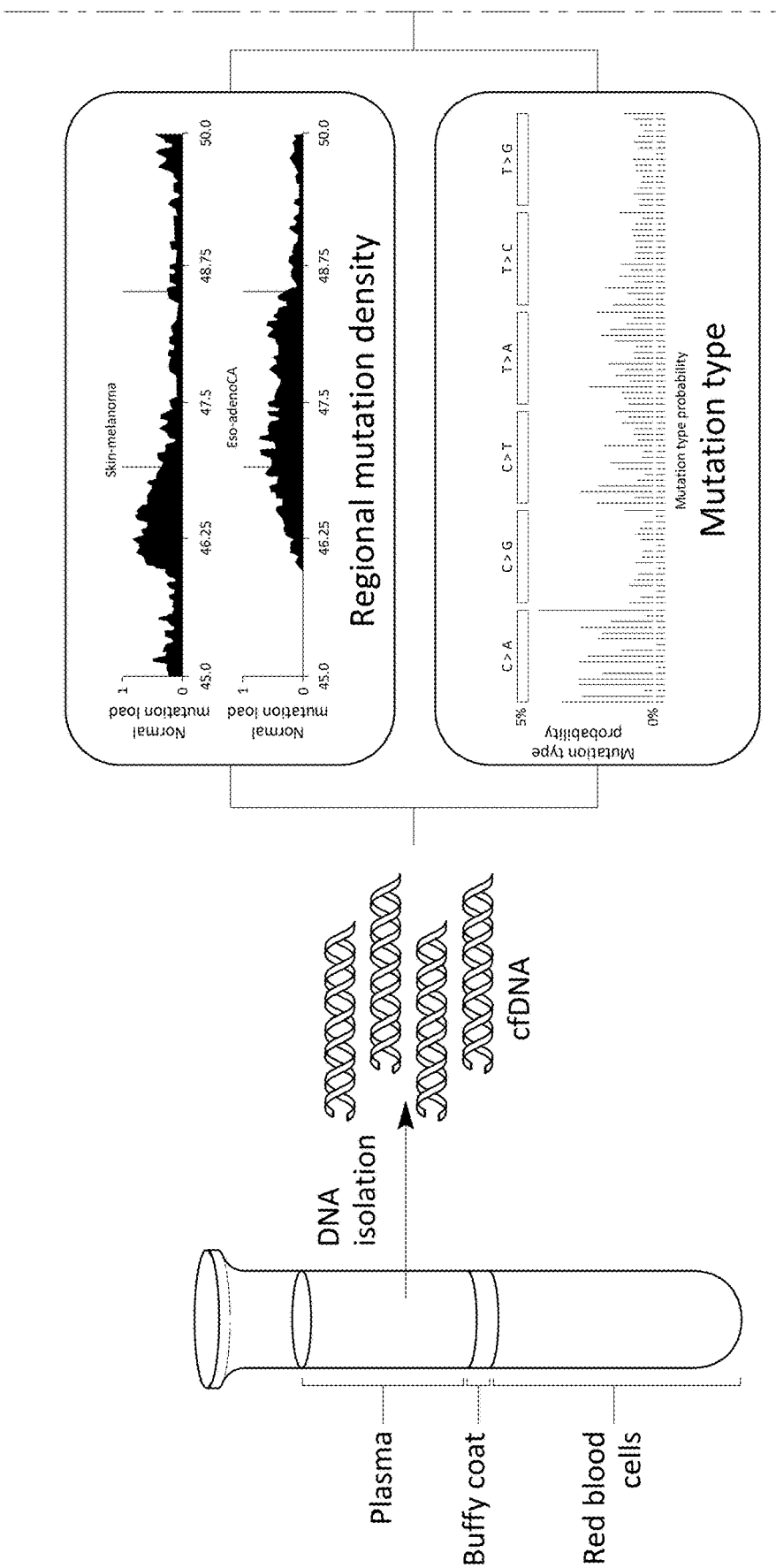
FIG. 1 shows an overall flowchart for determining chromosomal abnormality using a single nucleotide variant in a cell-free nucleic acid according to the present invention.

Unless otherwise defined, all technical and scientific terms used herein have the same meanings as typically understood by those skilled in the art to which the present invention belongs. In general, the nomenclature used herein and test methods described below are well known in the art and are typical.

Although terms such as "first", "second", "A", "B", etc. may be used to describe various components, these components are not to be limited by these terms, and the terms are only used to distinguish one component from another component. For instance, a "first" component may be named as a "second" component, and similarly, the "second" component may also be referred to as a "first" component, without departing from the scope of the technology to be described below. The term "and/or" includes a combination of a plurality of related listed items or any of a plurality of related listed items.

In the terms used herein, the singular forms are intended to include plural forms as well, unless the context clearly indicates otherwise, and it will be further understood that the terms such as "comprise", "include", etc. specify the presence of stated features, integers, steps, operations, components, parts, or combinations thereof, but do not preclude the presence or addition of one or more other features, integers, steps, operations, components, parts, or combinations thereof.

Before a detailed description of the drawings, it should be clarified that the classification of the constituent units in the present specification is merely a division depending on the main function that each constituent unit is responsible for. Specifically, two or more constituent units to be described below may be combined into one constituent unit, or one constituent unit may be divided into two or more for each more subdivided function. Furthermore, it will be understood that each of the constituent units to be described below may additionally perform some or all of the functions of other constituent units in addition to the main function it is responsible for and also that some of the main functions that the constituent units are responsible for may be exclusively performed by other constituent units.

Moreover, in performing the method or operation method, individual processes constituting the method may occur differently from the specified order unless a specific order is clearly described in context. Specifically, individual processes may occur in the same order as specified, may be performed substantially simultaneously, or may be performed in reverse order.

In the present invention, sequencing data obtained from a sample is aligned to a reference genome, nucleic acids are extracted from a biological sample to obtain sequence information, cancer-specific single nucleotide variants are extracted through filtering based on the aligned reads, and the regional mutation density of single nucleotide variants and the frequency of mutation signature of single nucleotide variants are calculated and input into a trained artificial intelligence model to analyze the calculated values, thereby making it possible to diagnose cancer and predict the type of cancer with high sensitivity and accuracy.

A method developed according to an embodiment of the present invention includes sequencing DNA extracted from blood, aligning the same to a reference genome, extracting cancer-specific single nucleotide variants through filtering based on the aligned reads, dividing the reference genome into predetermined bins, calculating the regional mutation density of single nucleotide variants in bins, calculating the frequency of mutation signature of single nucleotide variants, inputting the regional mutation density of single nucleotide variants and the frequency of mutation signature of single nucleotide variants into an artificial intelligence model trained to perform cancer diagnosis, comparing an output value with a reference value to diagnose cancer, inputting the regional mutation density of single nucleotide variants and the frequency of mutation signature of single nucleotide variants of the sample determined to be cancer into a second artificial intelligence model trained to classify types of cancer, and determining the type of cancer showing the highest value among output values to be the type of cancer of the sample (FIG. 1).

Accordingly, an aspect of the present invention pertains to a method for diagnosing cancer and predicting a cancer type using single nucleotide variants, including:
(a) extracting nucleic acids from a biological sample to obtain sequence information;
(b) aligning the obtained sequence information (reads) to a reference genome database;
(c) extracting cancer-specific single nucleotide variants by detecting single nucleotide variants in the aligned sequence information (reads) and performing filtering;
(d) dividing the reference genome into predetermined bins and calculating the regional mutation density of the extracted single nucleotide variants in each bin;
(e) calculating the frequency of mutation signature of the extracted single nucleotide variants; and
(f) inputting the regional mutation density of single nucleotide variants calculated in step (d) and the frequency of mutation signature of single nucleotide variants calculated in step (e) into an artificial intelligence model trained to perform cancer diagnosis and comparing an output value with a reference value.

In the present invention, the cancer may be solid cancer or blood cancer, is preferably selected from the group consisting of non-Hodgkin lymphoma, Hodgkin lymphoma, acute myeloid leukemia, acute lymphoid leukemia, multiple myeloma, head and neck cancer, lung cancer, glioblastoma, colorectal/rectal cancer, pancreatic cancer, breast cancer, ovarian cancer, melanoma, prostate cancer, thyroid cancer, liver cancer, stomach cancer, gallbladder cancer, biliary tract cancer, bladder cancer, small intestine cancer, cervical cancer, cancer of unknown primary site, kidney cancer, and mesothelioma, and is most preferably liver cancer or ovarian cancer, but the present invention is not limited thereto.

In the present invention, step (a) includes:
(a-i) obtaining nucleic acids from a biological sample;
(a-ii) obtaining purified nucleic acids by removing proteins, fats, and other residues from the collected nucleic acids using a salting-out method, a column chromatography method, or a bead method;
(a-iii) constructing a single-end sequencing library or a pair-end sequencing library for the purified nucleic acids or nucleic acids randomly fragmented through an enzymatic digestion, pulverization, or HydroShear method;
(a-iv) allowing the constructed library to react in a next-generation sequencer; and
(a-v) obtaining sequence information (reads) of the nucleic acids in the next-generation sequencer.

In the present invention, the obtaining the sequence information in step (a) may be characterized in that the isolated cell-free DNA is obtained through whole-genome sequencing to a depth of 1 million to 100 million reads.

In the present invention, the biological sample is any material, biological fluid, tissue, or cell obtained from or derived from a subject, and examples thereof may include, but are not limited to, whole blood, leukocytes, peripheral blood mononuclear cells, buffy coat, blood (including plasma and serum), sputum, tears, mucus, nasal washes, nasal aspirate, breath, urine, semen, saliva, peritoneal washings, pelvic fluids, cystic fluid, meningeal fluid, amniotic fluid, glandular fluid, pancreatic fluid, lymph fluid, pleural fluid, nipple aspirate, bronchial aspirate, synovial fluid, joint aspirate, organ secretions, cells, cell extract, hair, oral cells, placental cells, cerebrospinal fluid, and mixtures thereof.

As used herein, the term "reference group" refers to a reference population that may be compared like a reference nucleotide sequence database, and means a group of people who do not currently have a specific disease or condition. In the present invention, the reference nucleotide sequence in the reference genome database of the reference group may be a reference chromosome registered with a public health institution such as NCBI, etc.

In the present invention, the nucleic acid in step (a) may be cell-free DNA, preferably circulating tumor DNA, but is not limited thereto.

In the present invention, the next-generation sequencer may be used for any sequencing method known in the art. Sequencing of nucleic acids isolated through the selected method is typically performed using next-generation sequencing (NGS). Next-generation sequencing includes any sequencing method that determines the nucleotide sequence of any one of each nucleic acid molecule and a proxy clonally expanded from each nucleic acid molecule in a highly similar manner (e.g. $10^5$ or more molecules are sequenced simultaneously). In an exemplary embodiment, the relative abundance of nucleic acid species in a library may be estimated by counting the relative number of occurrences of cognate sequences thereof in data generated by sequencing experiments. The next-generation sequencing method is known in the art and is described in, for example, Metzker M. (2010) *Nature Biotechnology Reviews* 11:31-46, which is incorporated herein by reference.

In one embodiment, next-generation sequencing is performed to determine the nucleotide sequence of each nucleic acid molecule (e.g. HeliScope Gene Sequencing system from Helicos BioSciences and PacBio RS system from Pacific Biosciences). In another embodiment, sequencing, for example, massively parallel short-read sequencing (e.g. Solexa sequencer from Illumina Inc. of San Diego, CA) methods that yield more nucleotides of the sequence per sequencing unit than other sequencing methods that yield fewer but longer reads determine the nucleotide sequence of a proxy clonally expanded from each nucleic acid molecule (e.g. Solexa sequencer from Illumina Inc. of San Diego, CA; 454 Life Sciences (Branford, Connecticut) and Ion Torrent). Other methods or devices for next-generation sequencing may be provided by 454 Life Sciences (Branford, Connecticut), Applied Biosystems (Foster City, CA; SOLID Sequencer), Helicos Biosciences Corporation (Cambridge, Massachusetts), and emulsion and microfluidic sequencing nanodrops (e.g. GnuBIO Drops), but the present invention is not limited thereto.

Platforms for next-generation sequencing may include, but are not limited to, Roche/454's Genome Sequencer (GS) FLX System, Illumina/Solexa's Genome Analyzer (GA), Life/APG's Support Oligonucleotide Ligation Detection (SOLID) system, Polonator's G.007 system, Helicos Biosciences' HeliScope Gene Sequencing system, and Pacific Biosciences' PacBio RS system.

In the present invention, the aligning in step (b) may be performed using a BWA algorithm or an Hg19 sequence, but the present invention is not limited thereto.

In the present invention, the BWA algorithm may include, but is not limited to, BWA-ALN, BWA-SW, or Bowtie2.

In the present invention, the length of the sequence information (reads) in step (b) is 5 to 5,000 bp, and the number of reads that are used may be 5,000 to 5 million, but the present invention is not limited thereto.

In the present invention, the filtering in step (c) may be performed using any method capable of distinguishing a single nucleotide variant occurring in a normal person from a single nucleotide variant occurring specifically in cancer, and preferably includes extracting single nucleotide variants in which the read depth of a mutation region with detected single nucleotide variants is 3 or more and the average sequencing quality is 30 or more, but the present invention is not limited thereto.

In the present invention, the mutation region indicates the exact position of the single nucleotide variant, and the read depth of the mutation region of 3 or more means that the number of reads aligned at the corresponding position is 3 or more.

In the present invention, the filtering in step (c) may be characterized in that a process of removing artifacts and germline mutations generated during the sequencing process is further performed, and the process may include removing at least one mutation selected from the group consisting of:
 i) a mutation detected in only one of a read pair;
 ii) a mutation detected in two or more types at one position;
 iii) a mutation in which a normal base is not detected at each position; and
 iv) a mutation detected in a population database, but the present invention is not limited thereto.

In the present invention, the population database may be used without limitation, so long as it is a database including nucleotide sequence mutation information of normal persons, preferably a database including cfDNA WGS data of normal persons, WGS data of tissue samples, etc., more preferably a public database such as dbSNP, 1000 Genome, Hapmap, ExAC, Gnomad, etc., but the present invention is not limited thereto.

In the present invention, the bin in step (d) may be arbitrarily set, so long as it is a bin in which the regional mutation density of single nucleotide variants may be calculated, and is preferably 100 kb to 10 Mb, more preferably 500 kb to 5 Mb, most preferably 1 Mb, but the present invention is not limited thereto.

In the present invention, the calculating the regional mutation density (RMD) of the extracted single nucleotide variants in step (d) may be performed through a method including:
 (d-i) calculating the number of extracted single nucleotide variants in bins except for bins in which no mutation is detected at a reference value or more of the entire sample; and
 (d-ii) normalizing the calculated number by dividing the same by the total number of mutations in bins.

In the present invention, the reference value may be used without limitation, so long as it is a value capable of significantly discriminating the extracted single nucleotide variants, and is preferably 40 to 60%, more preferably 45 to 55%, most preferably 50%, but the present invention is not limited thereto.

In the present invention, for bins except for bins in which no mutation is detected at a reference value or more of the entire sample, when the reference value is 50%, it means that bins in which extracted single nucleotide variants are not present in 50% or more of the entire sample are excluded.

In the present invention, the bin may be at least one selected from among bins shown in Table 1.

In the present invention, the regional mutation density (RMD) of single nucleotide variants is used as a meaning similar to a background mutation rate, and means that the whole genome is divided into predetermined bins and mutation frequency thereof is calculated.

In the present invention, the regional mutation density of single nucleotide variants depending on the type of cancer is a quantitative value for a mutation-enriched region or a mutation-depleted region in the corresponding cancer. Cancer single nucleotide variants are not uniformly distributed throughout the human genome. The number of single nucleotide variants accumulated varies depending on the whole genome region, and the pattern of accumulation for each type of cancer is also very different. In addition, epigenetic characteristics (histone modification, replication time) are the main cause of the regional mutation density of single nucleotide variants depending on the type of cancer, and the regional mutation density of single nucleotide variants includes epigenetic characteristics of the corresponding cancer.

Since the regional mutation density of single nucleotide variants varies depending on the whole genome region and on the type of cancer, it may be a useful indicator for cancer diagnosis and cancer-type determination. Whether the detected mutation is a mutation located in a region with a high probability of occurrence in the corresponding cancer may be determined using the regional mutation density of single nucleotide variants.

In the present invention, the calculating the frequency of mutation signature of single nucleotide variants in step (e) may be performed through a method including:
- (e-i) calculating the number of mutations depending on the type of mutation below:
  - (1) a mutation in which cytosine (C) is substituted with thymine (T), adenine (A), or guanine (G),
  - (2) a mutation in which thymine is substituted with cytosine, adenine, or guanine,
  - (3) a mutation in which the mutation (1) or (2) further includes a base in a 5' direction thereof,
  - (4) a mutation in which the mutation (1) or (2) further includes a base in a 3' direction thereof, and
  - (5) a mutation in which a mutation in which adenine, guanine, cytosine, and thymine are substituted with different bases further includes a base in each of 5' and 3' directions thereof; and
- (e-ii) normalizing the sum of the calculated number of mutations by dividing the same by the total number.

In the present invention, the mutation signature may be at least one selected from among mutations shown in Table 2.

In the present invention, the mutation signature of single nucleotide variants may be used without limitation, so long as it is a mutation in which a normal base is mutated to a different base and functional abnormality of the gene occurs, and is preferably at least one selected from the group consisting of C→A, C→G, C→T, T→A, T→C, and T→G, but the present invention is not limited thereto.

In the present invention, C→A means that the detected mutation confirms whether a normal base C is mutated to a variant base A, and C→G means that the detected mutation confirms whether a normal base C is mutated to a variant base G, and the rest have the same meaning.

In the present invention, the reference value in step (f) may be used without limitation, so long as it is a value capable of diagnosing cancer, and is preferably 0.5, but is not limited thereto. When the reference value is 0.5, a case of 0.5 or more may be determined to be cancer.

In the present invention, the artificial intelligence model is trained such that the output result is close to 1 in the presence of cancer and the output result is close to 0 in the absence of cancer, and based on the reference value of 0.5, it is judged that there is cancer at 0.5 or more, whereas it is judged that there is no cancer at 0.5 or less, followed by performance measurement (training, validation, test accuracy).

Here, it is obvious to those skilled in the art that the reference value of 0.5 is a value that may be changed at any time. For example, if false positives are to be lowered, a reference value higher than 0.5 is set such that a criterion for determining that there is cancer may be made strict, and if false negatives are to be lowered, a reference value is set to be lower such that a criterion for determining that there is cancer may be made lenient.

In the present invention, the method may further include (g) predicting the type of cancer by inputting the regional mutation density of single nucleotide variants and the frequency of mutation signature of single nucleotide variants of the sample determined to be cancer into a second artificial intelligence model trained to classify types of cancer and comparing output values.

In the present invention, the comparing the output values in step (g) may be performed through a method including determining the type of cancer showing the highest value among the output values to be cancer of the sample.

In the present invention, the artificial intelligence model may be used without limitation, so long as it is a model capable of diagnosing cancer or determining the type of cancer, and is preferably an artificial neural network model, more preferably selected from the group consisting of a convolutional neural network, CNN), a deep neural network (DNN), a recurrent neural network (RNN), and an autoencoder, and most preferably a deep neural network, but the present invention is not limited thereto.

In the present invention, when the artificial intelligence model is a DNN and binary classification is trained, a loss function may be binary cross-entropy represented by Equation 1 below.

$$BCE = -\frac{1}{N}\sum_{i=0}^{N} y_i \cdot \log(\hat{y}_i) + (1-y_i) \cdot \log(1-\hat{y}_i) \quad \text{Equation 1}$$

Here, N is the total number of samples $\hat{y}_i$ is the probability value predicted by the model that the $i^{th}$ input value is close to class 1, and $y^i$ is the actual class of the $i^{th}$ input value.

In the present invention, when the second artificial intelligence model is a DNN and multi-class classification is trained, a loss function may be categorical cross-entropy represented by Equation 2 below.

$$CCE = -\frac{1}{N}\sum_{i=0}^{N}\sum_{j=0}^{J} y_j \cdot \log(\hat{y}_j) + (1-y_j) \cdot \log(1-\hat{y}_j) \quad \text{Equation 2}$$

Here, N is the total number of samples, J is the total number of classes, $y_j$ is the value representing an actual class of a sample, in which, if the actual class is j, it is represented as 1, and if the actual class is not j, it is represented as 0, and $\hat{y}j$ is the predicted probability value that the sample belongs to class j and is the predicted probability value that the closer to 1, the higher the probability of belonging to the class.

In the present invention, when the artificial intelligence model is a DNN, training may be performed as follows:
- i) classifying the produced data into training, validation, and test (performance evaluation) data, in which the training data is used when training the DNN model, the validation data is used for hyper-parameter tuning validation, and the test data is used for performance evaluation after optimal model production;
- ii) constructing an optimal DNN model through hyper-parameter tuning and training; and
- iii) determining the model having the best validation data performance as an optimal model by comparing the performance of various models obtained through hyper-parameter tuning using validation data.

In the present invention, the hyper-parameter tuning is a process of optimizing the values of various parameters (number of layers, number of filters, etc.) constituting the DNN model. As the hyper-parameter tuning process, hyper-band optimization, Bayesian optimization, or grid search techniques may be performed.

In the present invention, the training process optimizes the internal parameters (weights) of the DNN model using predetermined hyper-parameters, and when validation loss starts to increase relative to training loss, the model may be determined to be overfitting, and model training may be stopped before that.

Another aspect of the present invention pertains to an apparatus for diagnosing cancer and predicting the type of cancer based on artificial intelligence, including:

a decoding unit configured to decode sequence information by extracting nucleic acids from a biological sample;

an alignment unit configured to align the decoded sequence to a reference genome database;

a mutation detection unit configured to extract cancer-specific single nucleotide variants by detecting single nucleotide variants in the aligned sequence and performing filtering;

a single nucleotide variant distribution calculation unit configured to divide a reference genome into predetermined bins and calculate the regional mutation density of extracted single nucleotide variants in each bin;

a mutation frequency calculation unit configured to calculate the frequency of mutation signature of the extracted single nucleotide variants;

a cancer diagnosis unit configured to determine whether cancer is present or not by inputting the calculated regional mutation density of single nucleotide variants and the calculated mutation frequency thereof into an artificial intelligence model trained to perform cancer diagnosis and comparing an output value with a reference value; and a cancer-type prediction unit configured to predict the type of cancer by inputting the regional mutation density of single nucleotide variants of the sample determined to be cancer and the mutation frequency thereof into a second artificial intelligence model trained to classify types of cancer and comparing output values.

In the present invention, the decoding unit may include a nucleic acid injector configured to inject nucleic acids extracted by an independent device and a sequence information analyzer configured to analyze sequence information of the injected nucleic acids, and is preferably an NGS analysis device, but is not limited thereto.

In the present invention, the decoding unit may be configured to receive and decode sequence information data generated by an independent device.

Still another aspect of the present invention pertains to a computer-readable storage medium including instructions configured to be executed by a processor for diagnosing cancer and predicting the type of cancer, by:

(a) extracting nucleic acids from a biological sample to obtain sequence information;

(b) aligning the obtained sequence information (reads) to a reference genome database;

(c) extracting cancer-specific single nucleotide variants by detecting single nucleotide variants in the aligned sequence information (reads) and performing filtering;

(d) dividing the reference genome into predetermined bins and calculating the regional mutation density of the extracted single nucleotide variants in each bin;

(e) calculating the frequency of mutation signature of the extracted single nucleotide variants;

(f) determining whether cancer is present or not by inputting the regional mutation density of single nucleotide variants calculated in step (d) and the frequency of mutation signature of single nucleotide variants calculated in step (e) into an artificial intelligence model trained to perform cancer diagnosis and comparing an output value with a reference value; and (g) predicting the type of cancer by inputting the regional mutation density of single nucleotide variants and the frequency of mutation signature of single nucleotide variants of the sample determined to be cancer in step (f) into a second artificial intelligence model trained to classify types of cancer and comparing output values.

The method according to the present disclosure may be implemented using a computer. In one embodiment, the computer includes one or more processors coupled to a chipset. In addition, a memory, storage device, keyboard, graphics adapter, pointing device, and network adapter are connected to the chipset. In one embodiment, performance of the chipset is enabled by a memory controller Hub and an I/O controller hub. In other embodiments, the memory may be used by being directly connected to the processor instead of the chipset. The storage device is any device capable of holding data, including a hard drive, CD-ROM (compact disc read-only memory), DVD, or other memory devices. The memory is associated with data and instructions used by the processor. The pointing device may be a mouse, track ball, or another type of pointing device, and is used in combination with a keyboard to transmit input data to a computer system. The graphics adapter presents images and other information on the display. The network adapter is connected to the computer system through a local-area or long-distance communication network. The computer used herein is not limited to the above configuration, but may not include some configuration or may include an additional configuration, and may also be a part of a storage area network (SAN), and the computer of the present disclosure may be configured to be adapted to the execution of a module in a program for implementing the method according to the present invention.

As used herein, the module may be a functional and structural combination of hardware for performing the technical idea according to the present disclosure and software for driving the hardware. For example, the module may indicate a logical unit of a predetermined code and a hardware resource for executing the predetermined code, and does not necessarily mean a physically connected code or one type of hardware, as will be apparent to those skilled in the art.

EXAMPLES

A better understanding of the present invention may be obtained through the following examples. These examples are merely set forth to illustrate the present invention, and are not to be construed as limiting the scope of the present invention, as will be apparent to those of ordinary skill in the art.

Example 1. Extraction of DNA from Blood and Next-Generation Sequencing 10 mL of blood from each of 471 normal personas, 151 ovarian cancer patients, and 131 liver cancer patients was collected and stored in EDTA tubes. Within 2 hours after collection, only the plasma portion was primarily centrifuged under conditions of 1200 g, 4° C., and 15 minutes, after which the primarily centrifuged plasma was secondarily centrifuged under conditions of 16000 g, 4° C., and 10 minutes, thereby isolating the plasma supernatant excluding the precipitate. Cell-free DNA was extracted from the isolated plasma using a Tiangenmicro DNA kit (Tiangen), a library preparation process was performed using an MGIEasy cell-free DNA library prep set kit, and sequencing was performed in a 100-base paired-end mode using a DNBseq G400 instrument (MGI). Thereby, it was confirmed that about 170 million reads were produced per sample.

Example 2. Extraction of Single Nucleotide Variants and Extraction of Features Including Regional Mutation Density and Mutation Frequency of Single Nucleotide Variants 2-1. Filtering for Cancer-Specific Mutation Extraction The bam file obtained by aligning NGS data obtained in Example 1 to a reference genome (hg 19) was processed using a GATK pipeline. In order to acquire a mutation profile for each sample, mutations were detected using VarScan (mutation caller).

VarScan mutation detection was based on very lenient criteria. Variant calling was carried out on a lenient basis through at least one variant read, total depth of the mutation region of 3 or more, average sequencing quality of 30 or more, removal of minimum variant allele frequency, removal of strand filter, and removal of VarScan variant P value (in which a variant allele frequency is a mutation ratio, particularly the ratio of the number of reads in which mutations were detected among all reads at mutation positions).

After detection of all mutations that could be cancer-derived mutations based on the lenient criteria, artifacts and germline mutations were removed using various criteria. Four methods were used to remove mutations at incorrect positions.

First, when mutation positions in both forward and reverse reads of a fragment were sequenced, if there was a mutation in only one side of the read, it was removed. Second, if there were two or more mutations in one position, they were removed. Third, if the variant allele frequency was 1, a mutation was removed under assumption that there was no probability of a tumor-derived mutation because it means that a mutation is present in all DNA in the blood.

Fourth, mutations in various normal mutation databases and blacklist regions were removed. Blacklist regions are regions with a high probability of misalignment upon aligning, and include regions such as repeat and centromere. Blacklist regions are described in Haley M. Amemiya et al., *Scientific Report* Vol. 9, No. 9354, 2019. Moreover, in order to remove mutations with a high probability of being normal mutations, public databases that collect normal mutations were used. As such, dbSNP, 1000 Genome, Hapmap, ExAC, and Gnomad were used.

In addition, mutations in the cfDNA WGS database of normal persons produced by Green Cross were filtered because the possibility of tumor-derived mutations was low. In the input value of the algorithm for classifying types of cancer, mutations found in the cell-free DNA WGS of 412 normal persons in Example 1 were also removed.

2-2. Calculation of Regional Mutation Density of Single Nucleotide Variants

The whole genome was binned into 1 Mb, and the regional mutation density (RMD) of single nucleotide variants in each bin was calculated. For the mutations extracted in Example 2-1, the regional mutation density of single nucleotide variants in a total of 2726 bins except for bins in which there was no mutation in 50% or more of the entire sample was used as an input value for the algorithm. The number of mutations in each bin was calculated and divided by the total number of mutations in 2726 bins and thus normalized. Finally, 2726 regional mutation density features were generated, and the feature list is shown in Table 1 below.

TABLE 1

| | | | | |
|---|---|---|---|---|
| chr1: 0-1 Mb | chr12: 52 Mb-53 Mb | chr18: 36 Mb-37 Mb | chr3: 69 Mb-70 Mb | chr6: 52 Mb-53 Mb |
| chr1: 1 Mb-2 Mb | chr12: 53 Mb-54 Mb | chr18: 37 Mb-38 Mb | chr3: 70 Mb-71 Mb | chr6: 53 Mb-54 Mb |
| chr1: 2 Mb-3 Mb | chr12: 54 Mb-55 Mb | chr18: 38 Mb-39 Mb | chr3: 71 Mb-72 Mb | chr6: 54 Mb-55 Mb |
| chr1: 3 Mb-4 Mb | chr12: 55 Mb-56 Mb | chr18: 39 Mb-40 Mb | chr3: 72 Mb-73 Mb | chr6: 55 Mb-56 Mb |
| chr1: 4 Mb-5 Mb | chr12: 56 Mb-57 Mb | chr18: 40 Mb-41 Mb | chr3: 73 Mb-74 Mb | chr6: 56 Mb-57 Mb |
| chr1: 5 Mb-6 Mb | chr12: 57 Mb-58 Mb | chr18: 41 Mb-42 Mb | chr3: 74 Mb-75 Mb | chr6: 57 Mb-58 Mb |
| chr1: 6 Mb-7 Mb | chr12: 58 Mb-59 Mb | chr18: 42 Mb-43 Mb | chr3: 75 Mb-76 Mb | chr6: 58 Mb-59 Mb |
| chr1: 7 Mb-8 Mb | chr12: 59 Mb-60 Mb | chr18: 43 Mb-44 Mb | chr3: 76 Mb-77 Mb | chr6: 61 Mb-62 Mb |
| chr1: 8 Mb-9 Mb | chr12: 60 Mb-61 Mb | chr18: 44 Mb-45 Mb | chr3: 77 Mb-78 Mb | chr6: 62 Mb-63 Mb |
| chr1: 9 Mb-10 Mb | chr12: 61 Mb-62 Mb | chr18: 45 Mb-46 Mb | chr3: 78 Mb-79 Mb | chr6: 63 Mb-64 Mb |
| chr1: 10 Mb-11 Mb | chr12: 62 Mb-63 Mb | chr18: 46 Mb-47 Mb | chr3: 79 Mb-8 Mb0 | chr6: 64 Mb-65 Mb |
| chr1: 11 Mb-12 Mb | chr12: 63 Mb-64 Mb | chr18: 47 Mb-48 Mb | chr3: 8 Mb0-81 Mb | chr6: 65 Mb-66 Mb |
| chr1: 12 Mb-13 Mb | chr12: 64 Mb-65 Mb | chr18: 48 Mb-49 Mb | chr3: 81 Mb-82 Mb | chr6: 66 Mb-67 Mb |
| chr1: 13 Mb-14 Mb | chr12: 65 Mb-66 Mb | chr18: 49 Mb-50 Mb | chr3: 82 Mb-83 Mb | chr6: 67 Mb-68 Mb |
| chr1: 14 Mb-15 Mb | chr12: 66 Mb-67 Mb | chr18: 50 Mb-51 Mb | chr3: 83 Mb-84 Mb | chr6: 68 Mb-69 Mb |
| chr1: 15 Mb-16 Mb | chr12: 67 Mb-68 Mb | chr18: 51 Mb-52 Mb | chr3: 84 Mb-85 Mb | chr6: 69 Mb-70 Mb |
| chr1: 16 Mb-17 Mb | chr12: 68 Mb-69 Mb | chr18: 52 Mb-53 Mb | chr3: 85 Mb-86 Mb | chr6: 70 Mb-71 Mb |
| chr1: 17 Mb-18 Mb | chr12: 69 Mb-70 Mb | chr18: 53 Mb-54 Mb | chr3: 86 Mb-87 Mb | chr6: 71 Mb-72 Mb |
| chr1: 18 Mb-19 Mb | chr12: 70 Mb-71 Mb | chr18: 54 Mb-55 Mb | chr3: 87 Mb-88 Mb | chr6: 72 Mb-73 Mb |
| chr1: 19 Mb-20 Mb | chr12: 71 Mb-72 Mb | chr18: 55 Mb-56 Mb | chr3: 88 Mb-89 Mb | chr6: 73 Mb-74 Mb |
| chr1: 20 Mb-21 Mb | chr12: 72 Mb-73 Mb | chr18: 56 Mb-57 Mb | chr3: 89 Mb-90 Mb | chr6: 74 Mb-75 Mb |
| chr1: 21 Mb-22 Mb | chr12: 73 Mb-74 Mb | chr18: 57 Mb-58 Mb | chr3: 90 Mb-91 Mb | chr6: 75 Mb-76 Mb |
| chr1: 22 Mb-23 Mb | chr12: 74 Mb-75 Mb | chr18: 58 Mb-59 Mb | chr3: 93 Mb-94 Mb | chr6: 76 Mb-77 Mb |
| chr1: 23 Mb-24 Mb | chr12: 75 Mb-76 Mb | chr18: 59 Mb-60 Mb | chr3: 94 Mb-95 Mb | chr6: 77 Mb-78 Mb |
| chr1: 24 Mb-25 Mb | chr12: 76 Mb-77 Mb | chr18: 60 Mb-61 Mb | chr3: 95 Mb-96 Mb | chr6: 78 Mb-79 Mb |
| chr1: 25 Mb-26 Mb | chr12: 77 Mb-78 Mb | chr18: 61 Mb-62 Mb | chr3: 96 Mb-97 Mb | chr6: 79 Mb-8 Mb0 |
| chr1: 26 Mb-27 Mb | chr12: 78 Mb-79 Mb | chr18: 62 Mb-63 Mb | chr3: 97 Mb-98 Mb | chr6: 8 Mb0-81 Mb |
| chr1: 27 Mb-28 Mb | chr12: 79 Mb-8 Mb0 | chr18: 63 Mb-64 Mb | chr3: 98 Mb-99 Mb | chr6: 81 Mb-82 Mb |
| chr1: 28 Mb-29 Mb | chr12: 8 Mb0-81 Mb | chr18: 64 Mb-65 Mb | chr3: 99 Mb-100 Mb | chr6: 82 Mb-83 Mb |
| chr1: 29 Mb-30 Mb | chr12: 81 Mb-82 Mb | chr18: 65 Mb-66 Mb | chr3: 100 Mb-101 Mb | chr6: 83 Mb-84 Mb |
| chr1: 30 Mb-31 Mb | chr12: 82 Mb-83 Mb | chr18: 66 Mb-67 Mb | chr3: 101 Mb-102 Mb | chr6: 84 Mb-85 Mb |
| chr1: 31 Mb-32 Mb | chr12: 83 Mb-84 Mb | chr18: 67 Mb-68 Mb | chr3: 102 Mb-103 Mb | chr6: 85 Mb-86 Mb |
| chr1: 32 Mb-33 Mb | chr12: 84 Mb-85 Mb | chr18: 68 Mb-69 Mb | chr3: 103 Mb-104 Mb | chr6: 86 Mb-87 Mb |
| chr1: 33 Mb-34 Mb | chr12: 85 Mb-86 Mb | chr18: 69 Mb-70 Mb | chr3: 104 Mb-105 Mb | chr6: 87 Mb-88 Mb |
| chr1: 34 Mb-35 Mb | chr12: 86 Mb-87 Mb | chr18: 70 Mb-71 Mb | chr3: 105 Mb-106 Mb | chr6: 88 Mb-89 Mb |
| chr1: 35 Mb-36 Mb | chr12: 87 Mb-88 Mb | chr18: 71 Mb-72 Mb | chr3: 106 Mb-107 Mb | chr6: 89 Mb-90 Mb |
| chr1: 36 Mb-37 Mb | chr12: 88 Mb-89 Mb | chr18: 72 Mb-73 Mb | chr3: 107 Mb-108 Mb | chr6: 90 Mb-91 Mb |

TABLE 1-continued

| | | | | |
|---|---|---|---|---|
| chr1: 37 Mb-38 Mb | chr12: 89 Mb-90 Mb | chr18: 73 Mb-74 Mb | chr3: 108 Mb-109 Mb | chr6: 91 Mb-92 Mb |
| chr1: 38 Mb-39 Mb | chr12: 90 Mb-91 Mb | chr18: 74 Mb-75 Mb | chr3: 109 Mb-110 Mb | chr6: 92 Mb-93 Mb |
| chr1: 39 Mb-40 Mb | chr12: 91 Mb-92 Mb | chr18: 75 Mb-76 Mb | chr3: 110 Mb-111 Mb | chr6: 93 Mb-94 Mb |
| chr1: 40 Mb-41 Mb | chr12: 92 Mb-93 Mb | chr18: 76 Mb-77 Mb | chr3: 111 Mb-112 Mb | chr6: 94 Mb-95 Mb |
| chr1: 41 Mb-42 Mb | chr12: 93 Mb-94 Mb | chr18: 77 Mb-78 Mb | chr3: 112 Mb-113 Mb | chr6: 95 Mb-96 Mb |
| chr1: 42 Mb-43 Mb | chr12: 94 Mb-95 Mb | chr18: 78 Mb-78077248 | chr3: 113 Mb-114 Mb | chr6: 96 Mb-97 Mb |
| chr1: 43 Mb-44 Mb | chr12: 95 Mb-96 Mb | chr19: 0-1 Mb | chr3: 114 Mb-115 Mb | chr6: 97 Mb-98 Mb |
| chr1: 44 Mb-45 Mb | chr12: 96 Mb-97 Mb | chr19: 1 Mb-2 Mb | chr3: 115 Mb-116 Mb | chr6: 98 Mb-99 Mb |
| chr1: 45 Mb-46 Mb | chr12: 97 Mb-98 Mb | chr19: 2 Mb-3 Mb | chr3: 116 Mb-117 Mb | chr6: 99 Mb-100 Mb |
| chr1: 46 Mb-47 Mb | chr12: 98 Mb-99 Mb | chr19: 3 Mb-4 Mb | chr3: 117 Mb-118 Mb | chr6: 100 Mb-101 Mb |
| chr1: 47 Mb-48 Mb | chr12: 99 Mb-100 Mb | chr19: 4 Mb-5 Mb | chr3: 118 Mb-119 Mb | chr6: 101 Mb-102 Mb |
| chr1: 48 Mb-49 Mb | chr12: 100 Mb-101 Mb | chr19: 5 Mb-6 Mb | chr3: 119 Mb-120 Mb | chr6: 102 Mb-103 Mb |
| chr1: 49 Mb-50 Mb | chr12: 101 Mb-102 Mb | chr19: 6 Mb-7 Mb | chr3: 120 Mb-121 Mb | chr6: 103 Mb-104 Mb |
| chr1: 50 Mb-51 Mb | chr12: 102 Mb-103 Mb | chr19: 7 Mb-8 Mb | chr3: 121 Mb-122 Mb | chr6: 104 Mb-105 Mb |
| chr1: 51 Mb-52 Mb | chr12: 103 Mb-104 Mb | chr19: 8 Mb-9 Mb | chr3: 122 Mb-123 Mb | chr6: 105 Mb-106 Mb |
| chr1: 52 Mb-53 Mb | chr12: 104 Mb-105 Mb | chr19: 9 Mb-10 Mb | chr3: 123 Mb-124 Mb | chr6: 106 Mb-107 Mb |
| chr1: 53 Mb-54 Mb | chr12: 105 Mb-106 Mb | chr19: 10 Mb-11 Mb | chr3: 124 Mb-125 Mb | chr6: 107 Mb-108 Mb |
| chr1: 54 Mb-55 Mb | chr12: 106 Mb-107 Mb | chr19: 11 Mb-12 Mb | chr3: 125 Mb-126 Mb | chr6: 108 Mb-109 Mb |
| chr1: 55 Mb-56 Mb | chr12: 107 Mb-108 Mb | chr19: 12 Mb-13 Mb | chr3: 126 Mb-127 Mb | chr6: 109 Mb-110 Mb |
| chr1: 56 Mb-57 Mb | chr12: 108 Mb-109 Mb | chr19: 13 Mb-14 Mb | chr3: 127 Mb-128 Mb | chr6: 110 Mb-111 Mb |
| chr1: 57 Mb-58 Mb | chr12: 109 Mb-110 Mb | chr19: 14 Mb-15 Mb | chr3: 128 Mb-129 Mb | chr6: 111 Mb-112 Mb |
| chr1: 58 Mb-59 Mb | chr12: 110 Mb-111 Mb | chr19: 15 Mb-16 Mb | chr3: 129 Mb-130 Mb | chr6: 112 Mb-113 Mb |
| chr1: 59 Mb-60 Mb | chr12: 111 Mb-112 Mb | chr19: 16 Mb-17 Mb | chr3: 130 Mb-131 Mb | chr6: 113 Mb-114 Mb |
| chr1: 60 Mb-61 Mb | chr12: 112 Mb-113 Mb | chr19: 17 Mb-18 Mb | chr3: 131 Mb-132 Mb | chr6: 114 Mb-115 Mb |
| chr1: 61 Mb-62 Mb | chr12: 113 Mb-114 Mb | chr19: 18 Mb-19 Mb | chr3: 132 Mb-133 Mb | chr6: 115 Mb-116 Mb |
| chr1: 62 Mb-63 Mb | chr12: 114 Mb-115 Mb | chr19: 19 Mb-20 Mb | chr3: 133 Mb-134 Mb | chr6: 116 Mb-117 Mb |
| chr1: 63 Mb-64 Mb | chr12: 115 Mb-116 Mb | chr19: 20 Mb-21 Mb | chr3: 134 Mb-135 Mb | chr6: 117 Mb-118 Mb |
| chr1: 64 Mb-65 Mb | chr12: 116 Mb-117 Mb | chr19: 21 Mb-22 Mb | chr3: 135 Mb-136 Mb | chr6: 118 Mb-119 Mb |
| chr1: 65 Mb-66 Mb | chr12: 117 Mb-118 Mb | chr19: 22 Mb-23 Mb | chr3: 136 Mb-137 Mb | chr6: 119 Mb-120 Mb |
| chr1: 66 Mb-67 Mb | chr12: 118 Mb-119 Mb | chr19: 23 Mb-24 Mb | chr3: 137 Mb-138 Mb | chr6: 120 Mb-121 Mb |
| chr1: 67 Mb-68 Mb | chr12: 119 Mb-120 Mb | chr19: 24 Mb-25 Mb | chr3: 138 Mb-139 Mb | chr6: 121 Mb-122 Mb |
| chr1: 68 Mb-69 Mb | chr12: 120 Mb-121 Mb | chr19: 28 Mb-29 Mb | chr3: 139 Mb-140 Mb | chr6: 122 Mb-123 Mb |
| chr1: 69 Mb-70 Mb | chr12: 121 Mb-122 Mb | chr19: 29 Mb-30 Mb | chr3: 140 Mb-141 Mb | chr6: 123 Mb-124 Mb |
| chr1: 70 Mb-71 Mb | chr12: 122 Mb-123 Mb | chr19: 30 Mb-31 Mb | chr3: 141 Mb-142 Mb | chr6: 124 Mb-125 Mb |
| chr1: 71 Mb-72 Mb | chr12: 123 Mb-124 Mb | chr19: 31 Mb-32 Mb | chr3: 142 Mb-143 Mb | chr6: 125 Mb-126 Mb |
| chr1: 72 Mb-73 Mb | chr12: 124 Mb-125 Mb | chr19: 32 Mb-33 Mb | chr3: 143 Mb-144 Mb | chr6: 126 Mb-127 Mb |
| chr1: 73 Mb-74 Mb | chr12: 125 Mb-126 Mb | chr19: 33 Mb-34 Mb | chr3: 144 Mb-145 Mb | chr6: 127 Mb-128 Mb |
| chr1: 74 Mb-75 Mb | chr12: 126 Mb-127 Mb | chr19: 34 Mb-35 Mb | chr3: 145 Mb-146 Mb | chr6: 128 Mb-129 Mb |
| chr1: 75 Mb-76 Mb | chr12: 127 Mb-128 Mb | chr19: 35 Mb-36 Mb | chr3: 146 Mb-147 Mb | chr6: 129 Mb-130 Mb |
| chr1: 76 Mb-77 Mb | chr12: 128 Mb-129 Mb | chr19: 36 Mb-37 Mb | chr3: 147 Mb-148 Mb | chr6: 130 Mb-131 Mb |
| chr1: 77 Mb-78 Mb | chr12: 129 Mb-130 Mb | chr19: 37 Mb-38 Mb | chr3: 148 Mb-149 Mb | chr6: 131 Mb-132 Mb |
| chr1: 78 Mb-79 Mb | chr12: 130 Mb-131 Mb | chr19: 38 Mb-39 Mb | chr3: 149 Mb-150 Mb | chr6: 132 Mb-133 Mb |
| chr1: 79 Mb-8 Mb0 | chr12: 131 Mb-132 Mb | chr19: 39 Mb-40 Mb | chr3: 150 Mb-151 Mb | chr6: 133 Mb-134 Mb |
| chr1: 8 Mb0-81 Mb | chr12: 132 Mb-133 Mb | chr19: 40 Mb-41 Mb | chr3: 151 Mb-152 Mb | chr6: 134 Mb-135 Mb |
| chr1: 81 Mb-82 Mb | chr12: 133 Mb-133851895 | chr19: 41 Mb-42 Mb | chr3: 152 Mb-153 Mb | chr6: 135 Mb-136 Mb |
| chr1: 82 Mb-83 Mb | chr13: 19 Mb-20 Mb | chr19: 42 Mb-43 Mb | chr3: 153 Mb-154 Mb | chr6: 136 Mb-137 Mb |
| chr1: 83 Mb-84 Mb | chr13: 20 Mb-21 Mb | chr19: 43 Mb-44 Mb | chr3: 154 Mb-155 Mb | chr6: 137 Mb-138 Mb |
| chr1: 84 Mb-85 Mb | chr13: 21 Mb-22 Mb | chr19: 44 Mb-45 Mb | chr3: 155 Mb-156 Mb | chr6: 138 Mb-139 Mb |
| chr1: 85 Mb-86 Mb | chr13: 22 Mb-23 Mb | chr19: 45 Mb-46 Mb | chr3: 156 Mb-157 Mb | chr6: 139 Mb-140 Mb |
| chr1: 86 Mb-87 Mb | chr13: 23 Mb-24 Mb | chr19: 46 Mb-47 Mb | chr3: 157 Mb-158 Mb | chr6: 140 Mb-141 Mb |
| chr1: 87 Mb-88 Mb | chr13: 24 Mb-25 Mb | chr19: 47 Mb-48 Mb | chr3: 158 Mb-159 Mb | chr6: 141 Mb-142 Mb |
| chr1: 88 Mb-89 Mb | chr13: 25 Mb-26 Mb | chr19: 48 Mb-49 Mb | chr3: 159 Mb-160 Mb | chr6: 142 Mb-143 Mb |
| chr1: 89 Mb-90 Mb | chr13: 26 Mb-27 Mb | chr19: 49 Mb-50 Mb | chr3: 160 Mb-161 Mb | chr6: 143 Mb-144 Mb |
| chr1: 90 Mb-91 Mb | chr13: 27 Mb-28 Mb | chr19: 50 Mb-51 Mb | chr3: 161 Mb-162 Mb | chr6: 144 Mb-145 Mb |
| chr1: 91 Mb-92 Mb | chr13: 28 Mb-29 Mb | chr19: 51 Mb-52 Mb | chr3: 162 Mb-163 Mb | chr6: 145 Mb-146 Mb |
| chr1: 92 Mb-93 Mb | chr13: 29 Mb-30 Mb | chr19: 52 Mb-53 Mb | chr3: 163 Mb-164 Mb | chr6: 146 Mb-147 Mb |
| chr1: 93 Mb-94 Mb | chr13: 30 Mb-31 Mb | chr19: 53 Mb-54 Mb | chr3: 164 Mb-165 Mb | chr6: 147 Mb-148 Mb |
| chr1: 94 Mb-95 Mb | chr13: 31 Mb-32 Mb | chr19: 54 Mb-55 Mb | chr3: 165 Mb-166 Mb | chr6: 148 Mb-149 Mb |
| chr1: 95 Mb-96 Mb | chr13: 32 Mb-33 Mb | chr19: 55 Mb-56 Mb | chr3: 166 Mb-167 Mb | chr6: 149 Mb-150 Mb |
| chr1: 96 Mb-97 Mb | chr13: 33 Mb-34 Mb | chr19: 56 Mb-57 Mb | chr3: 167 Mb-168 Mb | chr6: 150 Mb-151 Mb |
| chr1: 97 Mb-98 Mb | chr13: 34 Mb-35 Mb | chr19: 57 Mb-58 Mb | chr3: 168 Mb-169 Mb | chr6: 151 Mb-152 Mb |
| chr1: 98 Mb-99 Mb | chr13: 35 Mb-36 Mb | chr19: 58 Mb-59 Mb | chr3: 169 Mb-170 Mb | chr6: 152 Mb-153 Mb |
| chr1: 99 Mb-100 Mb | chr13: 36 Mb-37 Mb | chr19: 59 Mb-59128983 | chr3: 170 Mb-171 Mb | chr6: 153 Mb-154 Mb |
| chr1: 100 Mb-101 Mb | chr13: 37 Mb-38 Mb | chr2: 0-1 Mb | chr3: 171 Mb-172 Mb | chr6: 154 Mb-155 Mb |
| chr1: 101 Mb-102 Mb | chr13: 38 Mb-39 Mb | chr2: 1 Mb-2 Mb | chr3: 172 Mb-173 Mb | chr6: 155 Mb-156 Mb |
| chr1: 102 Mb-103 Mb | chr13: 39 Mb-40 Mb | chr2: 2 Mb-3 Mb | chr3: 173 Mb-174 Mb | chr6: 156 Mb-157 Mb |
| chr1: 103 Mb-104 Mb | chr13: 40 Mb-41 Mb | chr2: 3 Mb-4 Mb | chr3: 174 Mb-175 Mb | chr6: 157 Mb-158 Mb |
| chr1: 104 Mb-105 Mb | chr13: 41 Mb-42 Mb | chr2: 4 Mb-5 Mb | chr3: 175 Mb-176 Mb | chr6: 158 Mb-159 Mb |
| chr1: 105 Mb-106 Mb | chr13: 42 Mb-43 Mb | chr2: 5 Mb-6 Mb | chr3: 176 Mb-177 Mb | chr6: 159 Mb-160 Mb |
| chr1: 106 Mb-107 Mb | chr13: 43 Mb-44 Mb | chr2: 6 Mb-7 Mb | chr3: 177 Mb-178 Mb | chr6: 160 Mb-161 Mb |
| chr1: 107 Mb-108 Mb | chr13: 44 Mb-45 Mb | chr2: 7 Mb-8 Mb | chr3: 178 Mb-179 Mb | chr6: 161 Mb-162 Mb |
| chr1: 108 Mb-109 Mb | chr13: 45 Mb-46 Mb | chr2: 8 Mb-9 Mb | chr3: 179 Mb-18 Mb0 | chr6: 162 Mb-163 Mb |
| chr1: 109 Mb-110 Mb | chr13: 46 Mb-47 Mb | chr2: 9 Mb-10 Mb | chr3: 18 Mb0-181 Mb | chr6: 163 Mb-164 Mb |
| chr1: 110 Mb-111 Mb | chr13: 47 Mb-48 Mb | chr2: 10 Mb-11 Mb | chr3: 181 Mb-182 Mb | chr6: 164 Mb-165 Mb |
| chr1: 111 Mb-112 Mb | chr13: 48 Mb-49 Mb | chr2: 11 Mb-12 Mb | chr3: 182 Mb-183 Mb | chr6: 165 Mb-166 Mb |
| chr1: 112 Mb-113 Mb | chr13: 49 Mb-50 Mb | chr2: 12 Mb-13 Mb | chr3: 183 Mb-184 Mb | chr6: 166 Mb-167 Mb |
| chr1: 113 Mb-114 Mb | chr13: 50 Mb-51 Mb | chr2: 13 Mb-14 Mb | chr3: 184 Mb-185 Mb | chr6: 167 Mb-168 Mb |
| chr1: 114 Mb-115 Mb | chr13: 51 Mb-52 Mb | chr2: 14 Mb-15 Mb | chr3: 185 Mb-186 Mb | chr6: 168 Mb-169 Mb |
| chr1: 115 Mb-116 Mb | chr13: 52 Mb-53 Mb | chr2: 15 Mb-16 Mb | chr3: 186 Mb-187 Mb | chr6: 169 Mb-170 Mb |
| chr1: 116 Mb-117 Mb | chr13: 53 Mb-54 Mb | chr2: 16 Mb-17 Mb | chr3: 187 Mb-188 Mb | chr6: 170 Mb-171 Mb |

TABLE 1-continued

| | | | | |
|---|---|---|---|---|
| chr1: 117 Mb-118 Mb | chr13: 54 Mb-55 Mb | chr2: 17 Mb-18 Mb | chr3: 188 Mb-189 Mb | chr7: 0-1 Mb |
| chr1: 118 Mb-119 Mb | chr13: 55 Mb-56 Mb | chr2: 18 Mb-19 Mb | chr3: 189 Mb-190 Mb | chr7: 1 Mb-2 Mb |
| chr1: 119 Mb-120 Mb | chr13: 56 Mb-57 Mb | chr2: 19 Mb-20 Mb | chr3: 190 Mb-191 Mb | chr7: 2 Mb-3 Mb |
| chr1: 120 Mb-121 Mb | chr13: 57 Mb-58 Mb | chr2: 20 Mb-21 Mb | chr3: 191 Mb-192 Mb | chr7: 3 Mb-4 Mb |
| chr1: 121 Mb-122 Mb | chr13: 58 Mb-59 Mb | chr2: 21 Mb-22 Mb | chr3: 192 Mb-193 Mb | chr7: 4 Mb-5 Mb |
| chr1: 142 Mb-143 Mb | chr13: 59 Mb-60 Mb | chr2: 22 Mb-23 Mb | chr3: 193 Mb-194 Mb | chr7: 5 Mb-6 Mb |
| chr1: 143 Mb-144 Mb | chr13: 60 Mb-61 Mb | chr2: 23 Mb-24 Mb | chr3: 194 Mb-195 Mb | chr7: 6 Mb-7 Mb |
| chr1: 144 Mb-145 Mb | chr13: 61 Mb-62 Mb | chr2: 24 Mb-25 Mb | chr3: 195 Mb-196 Mb | chr7: 7 Mb-8 Mb |
| chr1: 145 Mb-146 Mb | chr13: 62 Mb-63 Mb | chr2: 25 Mb-26 Mb | chr3: 196 Mb-197 Mb | chr7: 8 Mb-9 Mb |
| chr1: 146 Mb-147 Mb | chr13: 63 Mb-64 Mb | chr2: 26 Mb-27 Mb | chr3: 197 Mb-198 Mb | chr7: 9 Mb-10 Mb |
| chr1: 147 Mb-148 Mb | chr13: 64 Mb-65 Mb | chr2: 27 Mb-28 Mb | chr4: 0-1 Mb | chr7: 10 Mb-11 Mb |
| chr1: 148 Mb-149 Mb | chr13: 65 Mb-66 Mb | chr2: 28 Mb-29 Mb | chr4: 1 Mb-2 Mb | chr7: 11 Mb-12 Mb |
| chr1: 149 Mb-150 Mb | chr13: 66 Mb-67 Mb | chr2: 29 Mb-30 Mb | chr4: 2 Mb-3 Mb | chr7: 12 Mb-13 Mb |
| chr1: 150 Mb-151 Mb | chr13: 67 Mb-68 Mb | chr2: 30 Mb-31 Mb | chr4: 3 Mb-4 Mb | chr7: 13 Mb-14 Mb |
| chr1: 151 Mb-152 Mb | chr13: 68 Mb-69 Mb | chr2: 31 Mb-32 Mb | chr4: 4 Mb-5 Mb | chr7: 14 Mb-15 Mb |
| chr1: 152 Mb-153 Mb | chr13: 69 Mb-70 Mb | chr2: 32 Mb-33 Mb | chr4: 5 Mb-6 Mb | chr7: 15 Mb-16 Mb |
| chr1: 153 Mb-154 Mb | chr13: 70 Mb-71 Mb | chr2: 33 Mb-34 Mb | chr4: 6 Mb-7 Mb | chr7: 16 Mb-17 Mb |
| chr1: 154 Mb-155 Mb | chr13: 71 Mb-72 Mb | chr2: 34 Mb-35 Mb | chr4: 7 Mb-8 Mb | chr7: 17 Mb-18 Mb |
| chr1: 155 Mb-156 Mb | chr13: 72 Mb-73 Mb | chr2: 35 Mb-36 Mb | chr4: 8 Mb-9 Mb | chr7: 18 Mb-19 Mb |
| chr1: 156 Mb-157 Mb | chr13: 73 Mb-74 Mb | chr2: 36 Mb-37 Mb | chr4: 9 Mb-10 Mb | chr7: 19 Mb-20 Mb |
| chr1: 157 Mb-158 Mb | chr13: 74 Mb-75 Mb | chr2: 37 Mb-38 Mb | chr4: 10 Mb-11 Mb | chr7: 20 Mb-21 Mb |
| chr1: 158 Mb-159 Mb | chr13: 75 Mb-76 Mb | chr2: 38 Mb-39 Mb | chr4: 11 Mb-12 Mb | chr7: 21 Mb-22 Mb |
| chr1: 159 Mb-160 Mb | chr13: 76 Mb-77 Mb | chr2: 39 Mb-40 Mb | chr4: 12 Mb-13 Mb | chr7: 22 Mb-23 Mb |
| chr1: 160 Mb-161 Mb | chr13: 77 Mb-78 Mb | chr2: 40 Mb-41 Mb | chr4: 13 Mb-14 Mb | chr7: 23 Mb-24 Mb |
| chr1: 161 Mb-162 Mb | chr13: 78 Mb-79 Mb | chr2: 41 Mb-42 Mb | chr4: 14 Mb-15 Mb | chr7: 24 Mb-25 Mb |
| chr1: 162 Mb-163 Mb | chr13: 79 Mb-8 Mb0 | chr2: 42 Mb-43 Mb | chr4: 15 Mb-16 Mb | chr7: 25 Mb-26 Mb |
| chr1: 163 Mb-164 Mb | chr13: 8 Mb0-81 Mb | chr2: 43 Mb-44 Mb | chr4: 16 Mb-17 Mb | chr7: 26 Mb-27 Mb |
| chr1: 164 Mb-165 Mb | chr13: 81 Mb-82 Mb | chr2: 44 Mb-45 Mb | chr4: 17 Mb-18 Mb | chr7: 27 Mb-28 Mb |
| chr1: 165 Mb-166 Mb | chr13: 82 Mb-83 Mb | chr2: 45 Mb-46 Mb | chr4: 18 Mb-19 Mb | chr7: 28 Mb-29 Mb |
| chr1: 166 Mb-167 Mb | chr13: 83 Mb-84 Mb | chr2: 46 Mb-47 Mb | chr4: 19 Mb-20 Mb | chr7: 29 Mb-30 Mb |
| chr1: 167 Mb-168 Mb | chr13: 84 Mb-85 Mb | chr2: 47 Mb-48 Mb | chr4: 20 Mb-21 Mb | chr7: 30 Mb-31 Mb |
| chr1: 168 Mb-169 Mb | chr13: 85 Mb-86 Mb | chr2: 48 Mb-49 Mb | chr4: 21 Mb-22 Mb | chr7: 31 Mb-32 Mb |
| chr1: 169 Mb-170 Mb | chr13: 86 Mb-87 Mb | chr2: 49 Mb-50 Mb | chr4: 22 Mb-23 Mb | chr7: 32 Mb-33 Mb |
| chr1: 170 Mb-171 Mb | chr13: 87 Mb-88 Mb | chr2: 50 Mb-51 Mb | chr4: 23 Mb-24 Mb | chr7: 33 Mb-34 Mb |
| chr1: 171 Mb-172 Mb | chr13: 88 Mb-89 Mb | chr2: 51 Mb-52 Mb | chr4: 24 Mb-25 Mb | chr7: 34 Mb-35 Mb |
| chr1: 172 Mb-173 Mb | chr13: 89 Mb-90 Mb | chr2: 52 Mb-53 Mb | chr4: 25 Mb-26 Mb | chr7: 35 Mb-36 Mb |
| chr1: 173 Mb-174 Mb | chr13: 90 Mb-91 Mb | chr2: 53 Mb-54 Mb | chr4: 26 Mb-27 Mb | chr7: 36 Mb-37 Mb |
| chr1: 174 Mb-175 Mb | chr13: 91 Mb-92 Mb | chr2: 54 Mb-55 Mb | chr4: 27 Mb-28 Mb | chr7: 37 Mb-38 Mb |
| chr1: 175 Mb-176 Mb | chr13: 92 Mb-93 Mb | chr2: 55 Mb-56 Mb | chr4: 28 Mb-29 Mb | chr7: 38 Mb-39 Mb |
| chr1: 176 Mb-177 Mb | chr13: 93 Mb-94 Mb | chr2: 56 Mb-57 Mb | chr4: 29 Mb-30 Mb | chr7: 39 Mb-40 Mb |
| chr1: 177 Mb-178 Mb | chr13: 94 Mb-95 Mb | chr2: 57 Mb-58 Mb | chr4: 30 Mb-31 Mb | chr7: 40 Mb-41 Mb |
| chr1: 178 Mb-179 Mb | chr13: 95 Mb-96 Mb | chr2: 58 Mb-59 Mb | chr4: 31 Mb-32 Mb | chr7: 41 Mb-42 Mb |
| chr1: 179 Mb-18 Mb0 | chr13: 96 Mb-97 Mb | chr2: 59 Mb-60 Mb | chr4: 32 Mb-33 Mb | chr7: 42 Mb-43 Mb |
| chr1: 18 Mb0-181 Mb | chr13: 97 Mb-98 Mb | chr2: 60 Mb-61 Mb | chr4: 33 Mb-34 Mb | chr7: 43 Mb-44 Mb |
| chr1: 181 Mb-182 Mb | chr13: 98 Mb-99 Mb | chr2: 61 Mb-62 Mb | chr4: 34 Mb-35 Mb | chr7: 44 Mb-45 Mb |
| chr1: 182 Mb-183 Mb | chr13: 99 Mb-100 Mb | chr2: 62 Mb-63 Mb | chr4: 35 Mb-36 Mb | chr7: 45 Mb-46 Mb |
| chr1: 183 Mb-184 Mb | chr13: 100 Mb-101 Mb | chr2: 63 Mb-64 Mb | chr4: 36 Mb-37 Mb | chr7: 46 Mb-47 Mb |
| chr1: 184 Mb-185 Mb | chr13: 101 Mb-102 Mb | chr2: 64 Mb-65 Mb | chr4: 37 Mb-38 Mb | chr7: 47 Mb-48 Mb |
| chr1: 185 Mb-186 Mb | chr13: 102 Mb-103 Mb | chr2: 65 Mb-66 Mb | chr4: 38 Mb-39 Mb | chr7: 48 Mb-49 Mb |
| chr1: 186 Mb-187 Mb | chr13: 103 Mb-104 Mb | chr2: 66 Mb-67 Mb | chr4: 39 Mb-40 Mb | chr7: 49 Mb-50 Mb |
| chr1: 187 Mb-188 Mb | chr13: 104 Mb-105 Mb | chr2: 67 Mb-68 Mb | chr4: 40 Mb-41 Mb | chr7: 50 Mb-51 Mb |
| chr1: 188 Mb-189 Mb | chr13: 105 Mb-106 Mb | chr2: 68 Mb-69 Mb | chr4: 41 Mb-42 Mb | chr7: 51 Mb-52 Mb |
| chr1: 189 Mb-190 Mb | chr13: 106 Mb-107 Mb | chr2: 69 Mb-70 Mb | chr4: 42 Mb-43 Mb | chr7: 52 Mb-53 Mb |
| chr1: 190 Mb-191 Mb | chr13: 107 Mb-108 Mb | chr2: 70 Mb-71 Mb | chr4: 43 Mb-44 Mb | chr7: 53 Mb-54 Mb |
| chr1: 191 Mb-192 Mb | chr13: 108 Mb-109 Mb | chr2: 71 Mb-72 Mb | chr4: 44 Mb-45 Mb | chr7: 54 Mb-55 Mb |
| chr1: 192 Mb-193 Mb | chr13: 109 Mb-110 Mb | chr2: 72 Mb-73 Mb | chr4: 45 Mb-46 Mb | chr7: 55 Mb-56 Mb |
| chr1: 193 Mb-194 Mb | chr13: 110 Mb-111 Mb | chr2: 73 Mb-74 Mb | chr4: 46 Mb-47 Mb | chr7: 56 Mb-57 Mb |
| chr1: 194 Mb-195 Mb | chr13: 111 Mb-112 Mb | chr2: 74 Mb-75 Mb | chr4: 47 Mb-48 Mb | chr7: 57 Mb-58 Mb |
| chr1: 195 Mb-196 Mb | chr13: 112 Mb-113 Mb | chr2: 75 Mb-76 Mb | chr4: 48 Mb-49 Mb | chr7: 62 Mb-63 Mb |
| chr1: 196 Mb-197 Mb | chr13: 113 Mb-114 Mb | chr2: 76 Mb-77 Mb | chr4: 49 Mb-50 Mb | chr7: 63 Mb-64 Mb |
| chr1: 197 Mb-198 Mb | chr13: 114 Mb-115 Mb | chr2: 77 Mb-78 Mb | chr4: 52 Mb-53 Mb | chr7: 64 Mb-65 Mb |
| chr1: 198 Mb-199 Mb | chr13: 115 Mb-115169878 | chr2: 78 Mb-79 Mb | chr4: 53 Mb-54 Mb | chr7: 65 Mb-66 Mb |
| chr1: 199 Mb-20 Mb | chr14: 19 Mb-20 Mb | chr2: 79 Mb-8 Mb0 | chr4: 54 Mb-55 Mb | chr7: 66 Mb-67 Mb |
| chr1: 20 Mb0-201 Mb | chr14: 20 Mb-21 Mb | chr2: 8 Mb0-81 Mb | chr4: 55 Mb-56 Mb | chr7: 67 Mb-68 Mb |
| chr1: 201 Mb-202 Mb | chr14: 21 Mb-22 Mb | chr2: 81 Mb-82 Mb | chr4: 56 Mb-57 Mb | chr7: 68 Mb-69 Mb |
| chr1: 202 Mb-203 Mb | chr14: 22 Mb-23 Mb | chr2: 82 Mb-83 Mb | chr4: 57 Mb-58 Mb | chr7: 69 Mb-70 Mb |
| chr1: 203 Mb-204 Mb | chr14: 23 Mb-24 Mb | chr2: 83 Mb-84 Mb | chr4: 58 Mb-59 Mb | chr7: 70 Mb-71 Mb |
| chr1: 204 Mb-205 Mb | chr14: 24 Mb-25 Mb | chr2: 84 Mb-85 Mb | chr4: 59 Mb-60 Mb | chr7: 71 Mb-72 Mb |
| chr1: 205 Mb-206 Mb | chr14: 25 Mb-26 Mb | chr2: 85 Mb-86 Mb | chr4: 60 Mb-61 Mb | chr7: 72 Mb-73 Mb |
| chr1: 206 Mb-207 Mb | chr14: 26 Mb-27 Mb | chr2: 86 Mb-87 Mb | chr4: 61 Mb-62 Mb | chr7: 73 Mb-74 Mb |
| chr1: 207 Mb-208 Mb | chr14: 27 Mb-28 Mb | chr2: 87 Mb-88 Mb | chr4: 62 Mb-63 Mb | chr7: 74 Mb-75 Mb |
| chr1: 208 Mb-209 Mb | chr14: 28 Mb-29 Mb | chr2: 88 Mb-89 Mb | chr4: 63 Mb-64 Mb | chr7: 75 Mb-76 Mb |
| chr1: 209 Mb-210 Mb | chr14: 29 Mb-30 Mb | chr2: 89 Mb-90 Mb | chr4: 64 Mb-65 Mb | chr7: 76 Mb-77 Mb |
| chr1: 210 Mb-211 Mb | chr14: 30 Mb-31 Mb | chr2: 90 Mb-91 Mb | chr4: 65 Mb-66 Mb | chr7: 77 Mb-78 Mb |
| chr1: 211 Mb-212 Mb | chr14: 31 Mb-32 Mb | chr2: 91 Mb-92 Mb | chr4: 66 Mb-67 Mb | chr7: 78 Mb-79 Mb |
| chr1: 212 Mb-213 Mb | chr14: 32 Mb-33 Mb | chr2: 92 Mb-93 Mb | chr4: 67 Mb-68 Mb | chr7: 79 Mb-8 Mb0 |
| chr1: 213 Mb-214 Mb | chr14: 33 Mb-34 Mb | chr2: 95 Mb-96 Mb | chr4: 68 Mb-69 Mb | chr7: 8 Mb0-81 Mb |
| chr1: 214 Mb-215 Mb | chr14: 34 Mb-35 Mb | chr2: 96 Mb-97 Mb | chr4: 69 Mb-70 Mb | chr7: 81 Mb-82 Mb |
| chr1: 215 Mb-216 Mb | chr14: 35 Mb-36 Mb | chr2: 97 Mb-98 Mb | chr4: 70 Mb-71 Mb | chr7: 82 Mb-83 Mb |
| chr1: 216 Mb-217 Mb | chr14: 36 Mb-37 Mb | chr2: 98 Mb-99 Mb | chr4: 71 Mb-72 Mb | chr7: 83 Mb-84 Mb |

TABLE 1-continued

| | | | | |
|---|---|---|---|---|
| chr1: 217 Mb-218 Mb | chr14: 37 Mb-38 Mb | chr2: 99 Mb-100 Mb | chr4: 72 Mb-73 Mb | chr7: 84 Mb-85 Mb |
| chr1: 218 Mb-219 Mb | chr14: 38 Mb-39 Mb | chr2: 100 Mb-101 Mb | chr4: 73 Mb-74 Mb | chr7: 85 Mb-86 Mb |
| chr1: 219 Mb-220 Mb | chr14: 39 Mb-40 Mb | chr2: 101 Mb-102 Mb | chr4: 74 Mb-75 Mb | chr7: 86 Mb-87 Mb |
| chr1: 220 Mb-221 Mb | chr14: 40 Mb-41 Mb | chr2: 102 Mb-103 Mb | chr4: 75 Mb-76 Mb | chr7: 87 Mb-88 Mb |
| chr1: 221 Mb-222 Mb | chr14: 41 Mb-42 Mb | chr2: 103 Mb-104 Mb | chr4: 76 Mb-77 Mb | chr7: 88 Mb-89 Mb |
| chr1: 222 Mb-223 Mb | chr14: 42 Mb-43 Mb | chr2: 104 Mb-105 Mb | chr4: 77 Mb-78 Mb | chr7: 89 Mb-90 Mb |
| chr1: 223 Mb-224 Mb | chr14: 43 Mb-44 Mb | chr2: 105 Mb-106 Mb | chr4: 78 Mb-79 Mb | chr7: 90 Mb-91 Mb |
| chr1: 224 Mb-225 Mb | chr14: 44 Mb-45 Mb | chr2: 106 Mb-107 Mb | chr4: 79 Mb-8 Mb0 | chr7: 91 Mb-92 Mb |
| chr1: 225 Mb-226 Mb | chr14: 45 Mb-46 Mb | chr2: 107 Mb-108 Mb | chr4: 8 Mb0-81 Mb | chr7: 92 Mb-93 Mb |
| chr1: 226 Mb-227 Mb | chr14: 46 Mb-47 Mb | chr2: 108 Mb-109 Mb | chr4: 81 Mb-82 Mb | chr7: 93 Mb-94 Mb |
| chr1: 227 Mb-228 Mb | chr14: 47 Mb-48 Mb | chr2: 109 Mb-110 Mb | chr4: 82 Mb-83 Mb | chr7: 94 Mb-95 Mb |
| chr1: 228 Mb-229 Mb | chr14: 48 Mb-49 Mb | chr2: 110 Mb-111 Mb | chr4: 83 Mb-84 Mb | chr7: 95 Mb-96 Mb |
| chr1: 229 Mb-230 Mb | chr14: 49 Mb-50 Mb | chr2: 111 Mb-112 Mb | chr4: 84 Mb-85 Mb | chr7: 96 Mb-97 Mb |
| chr1: 230 Mb-231 Mb | chr14: 50 Mb-51 Mb | chr2: 112 Mb-113 Mb | chr4: 85 Mb-86 Mb | chr7: 97 Mb-98 Mb |
| chr1: 231 Mb-232 Mb | chr14: 51 Mb-52 Mb | chr2: 113 Mb-114 Mb | chr4: 86 Mb-87 Mb | chr7: 98 Mb-99 Mb |
| chr1: 232 Mb-233 Mb | chr14: 52 Mb-53 Mb | chr2: 114 Mb-115 Mb | chr4: 87 Mb-88 Mb | chr7: 99 Mb-100 Mb |
| chr1: 233 Mb-234 Mb | chr14: 53 Mb-54 Mb | chr2: 115 Mb-116 Mb | chr4: 88 Mb-89 Mb | chr7: 100 Mb-101 Mb |
| chr1: 234 Mb-235 Mb | chr14: 54 Mb-55 Mb | chr2: 116 Mb-117 Mb | chr4: 89 Mb-90 Mb | chr7: 101 Mb-102 Mb |
| chr1: 235 Mb-236 Mb | chr14: 55 Mb-56 Mb | chr2: 117 Mb-118 Mb | chr4: 90 Mb-91 Mb | chr7: 102 Mb-103 Mb |
| chr1: 236 Mb-237 Mb | chr14: 56 Mb-57 Mb | chr2: 118 Mb-119 Mb | chr4: 91 Mb-92 Mb | chr7: 103 Mb-104 Mb |
| chr1: 237 Mb-238 Mb | chr14: 57 Mb-58 Mb | chr2: 119 Mb-120 Mb | chr4: 92 Mb-93 Mb | chr7: 104 Mb-105 Mb |
| chr1: 238 Mb-239 Mb | chr14: 58 Mb-59 Mb | chr2: 120 Mb-121 Mb | chr4: 93 Mb-94 Mb | chr7: 105 Mb-106 Mb |
| chr1: 239 Mb-240 Mb | chr14: 59 Mb-60 Mb | chr2: 121 Mb-122 Mb | chr4: 94 Mb-95 Mb | chr7: 106 Mb-107 Mb |
| chr1: 240 Mb-241 Mb | chr14: 60 Mb-61 Mb | chr2: 122 Mb-123 Mb | chr4: 95 Mb-96 Mb | chr7: 107 Mb-108 Mb |
| chr1: 241 Mb-242 Mb | chr14: 61 Mb-62 Mb | chr2: 123 Mb-124 Mb | chr4: 96 Mb-97 Mb | chr7: 108 Mb-109 Mb |
| chr1: 242 Mb-243 Mb | chr14: 62 Mb-63 Mb | chr2: 124 Mb-125 Mb | chr4: 97 Mb-98 Mb | chr7: 109 Mb-110 Mb |
| chr1: 243 Mb-244 Mb | chr14: 63 Mb-64 Mb | chr2: 125 Mb-126 Mb | chr4: 98 Mb-99 Mb | chr7: 110 Mb-111 Mb |
| chr1: 244 Mb-245 Mb | chr14: 64 Mb-65 Mb | chr2: 126 Mb-127 Mb | chr4: 99 Mb-100 Mb | chr7: 111 Mb-112 Mb |
| chr1: 245 Mb-246 Mb | chr14: 65 Mb-66 Mb | chr2: 127 Mb-128 Mb | chr4: 100 Mb-101 Mb | chr7: 112 Mb-113 Mb |
| chr1: 246 Mb-247 Mb | chr14: 66 Mb-67 Mb | chr2: 128 Mb-129 Mb | chr4: 101 Mb-102 Mb | chr7: 113 Mb-114 Mb |
| chr1: 247 Mb-248 Mb | chr14: 67 Mb-68 Mb | chr2: 129 Mb-130 Mb | chr4: 102 Mb-103 Mb | chr7: 114 Mb-115 Mb |
| chr1: 248 Mb-249 Mb | chr14: 68 Mb-69 Mb | chr2: 130 Mb-131 Mb | chr4: 103 Mb-104 Mb | chr7: 115 Mb-116 Mb |
| chr1: 249 Mb-249250621 | chr14: 69 Mb-70 Mb | chr2: 131 Mb-132 Mb | chr4: 104 Mb-105 Mb | chr7: 116 Mb-117 Mb |
| chr10: 0-1 Mb | chr14: 70 Mb-71 Mb | chr2: 132 Mb-133 Mb | chr4: 105 Mb-106 Mb | chr7: 117 Mb-118 Mb |
| chr10: 1 Mb-2 Mb | chr14: 71 Mb-72 Mb | chr2: 133 Mb-134 Mb | chr4: 106 Mb-107 Mb | chr7: 118 Mb-119 Mb |
| chr10: 2 Mb-3 Mb | chr14: 72 Mb-73 Mb | chr2: 134 Mb-135 Mb | chr4: 107 Mb-108 Mb | chr7: 119 Mb-120 Mb |
| chr10: 3 Mb-4 Mb | chr14: 73 Mb-74 Mb | chr2: 135 Mb-136 Mb | chr4: 108 Mb-109 Mb | chr7: 120 Mb-121 Mb |
| chr10: 4 Mb-5 Mb | chr14: 74 Mb-75 Mb | chr2: 136 Mb-137 Mb | chr4: 109 Mb-110 Mb | chr7: 121 Mb-122 Mb |
| chr10: 5 Mb-6 Mb | chr14: 75 Mb-76 Mb | chr2: 137 Mb-138 Mb | chr4: 110 Mb-111 Mb | chr7: 122 Mb-123 Mb |
| chr10: 6 Mb-7 Mb | chr14: 76 Mb-77 Mb | chr2: 138 Mb-139 Mb | chr4: 111 Mb-112 Mb | chr7: 123 Mb-124 Mb |
| chr10: 7 Mb-8 Mb | chr14: 77 Mb-78 Mb | chr2: 139 Mb-140 Mb | chr4: 112 Mb-113 Mb | chr7: 124 Mb-125 Mb |
| chr10: 8 Mb-9 Mb | chr14: 78 Mb-79 Mb | chr2: 140 Mb-141 Mb | chr4: 113 Mb-114 Mb | chr7: 125 Mb-126 Mb |
| chr10: 9 Mb-10 Mb | chr14: 79 Mb-8 Mb0 | chr2: 141 Mb-142 Mb | chr4: 114 Mb-115 Mb | chr7: 126 Mb-127 Mb |
| chr10: 10 Mb-11 Mb | chr14: 8 Mb0-81 Mb | chr2: 142 Mb-143 Mb | chr4: 115 Mb-116 Mb | chr7: 127 Mb-128 Mb |
| chr10: 11 Mb-12 Mb | chr14: 81 Mb-82 Mb | chr2: 143 Mb-144 Mb | chr4: 116 Mb-117 Mb | chr7: 128 Mb-129 Mb |
| chr10: 12 Mb-13 Mb | chr14: 82 Mb-83 Mb | chr2: 144 Mb-145 Mb | chr4: 117 Mb-118 Mb | chr7: 129 Mb-130 Mb |
| chr10: 13 Mb-14 Mb | chr14: 83 Mb-84 Mb | chr2: 145 Mb-146 Mb | chr4: 118 Mb-119 Mb | chr7: 130 Mb-131 Mb |
| chr10: 14 Mb-15 Mb | chr14: 84 Mb-85 Mb | chr2: 146 Mb-147 Mb | chr4: 119 Mb-120 Mb | chr7: 131 Mb-132 Mb |
| chr10: 15 Mb-16 Mb | chr14: 85 Mb-86 Mb | chr2: 147 Mb-148 Mb | chr4: 120 Mb-121 Mb | chr7: 132 Mb-133 Mb |
| chr10: 16 Mb-17 Mb | chr14: 86 Mb-87 Mb | chr2: 148 Mb-149 Mb | chr4: 121 Mb-122 Mb | chr7: 133 Mb-134 Mb |
| chr10: 17 Mb-18 Mb | chr14: 87 Mb-88 Mb | chr2: 149 Mb-150 Mb | chr4: 122 Mb-123 Mb | chr7: 134 Mb-135 Mb |
| chr10: 18 Mb-19 Mb | chr14: 88 Mb-89 Mb | chr2: 150 Mb-151 Mb | chr4: 123 Mb-124 Mb | chr7: 135 Mb-136 Mb |
| chr10: 19 Mb-20 Mb | chr14: 89 Mb-90 Mb | chr2: 151 Mb-152 Mb | chr4: 124 Mb-125 Mb | chr7: 136 Mb-137 Mb |
| chr10: 20 Mb-21 Mb | chr14: 90 Mb-91 Mb | chr2: 152 Mb-153 Mb | chr4: 125 Mb-126 Mb | chr7: 137 Mb-138 Mb |
| chr10: 21 Mb-22 Mb | chr14: 91 Mb-92 Mb | chr2: 153 Mb-154 Mb | chr4: 126 Mb-127 Mb | chr7: 138 Mb-139 Mb |
| chr10: 22 Mb-23 Mb | chr14: 92 Mb-93 Mb | chr2: 154 Mb-155 Mb | chr4: 127 Mb-128 Mb | chr7: 139 Mb-140 Mb |
| chr10: 23 Mb-24 Mb | chr14: 93 Mb-94 Mb | chr2: 155 Mb-156 Mb | chr4: 128 Mb-129 Mb | chr7: 140 Mb-141 Mb |
| chr10: 24 Mb-25 Mb | chr14: 94 Mb-95 Mb | chr2: 156 Mb-157 Mb | chr4: 129 Mb-130 Mb | chr7: 141 Mb-142 Mb |
| chr10: 25 Mb-26 Mb | chr14: 95 Mb-96 Mb | chr2: 157 Mb-158 Mb | chr4: 130 Mb-131 Mb | chr7: 142 Mb-143 Mb |
| chr10: 26 Mb-27 Mb | chr14: 96 Mb-97 Mb | chr2: 158 Mb-159 Mb | chr4: 131 Mb-132 Mb | chr7: 143 Mb-144 Mb |
| chr10: 27 Mb-28 Mb | chr14: 97 Mb-98 Mb | chr2: 159 Mb-160 Mb | chr4: 132 Mb-133 Mb | chr7: 144 Mb-145 Mb |
| chr10: 28 Mb-29 Mb | chr14: 98 Mb-99 Mb | chr2: 160 Mb-161 Mb | chr4: 133 Mb-134 Mb | chr7: 145 Mb-146 Mb |
| chr10: 29 Mb-30 Mb | chr14: 99 Mb-100 Mb | chr2: 161 Mb-162 Mb | chr4: 134 Mb-135 Mb | chr7: 146 Mb-147 Mb |
| chr10: 30 Mb-31 Mb | chr14: 100 Mb-101 Mb | chr2: 162 Mb-163 Mb | chr4: 135 Mb-136 Mb | chr7: 147 Mb-148 Mb |
| chr10: 31 Mb-32 Mb | chr14: 101 Mb-102 Mb | chr2: 163 Mb-164 Mb | chr4: 136 Mb-137 Mb | chr7: 148 Mb-149 Mb |
| chr10: 32 Mb-33 Mb | chr14: 102 Mb-103 Mb | chr2: 164 Mb-165 Mb | chr4: 137 Mb-138 Mb | chr7: 149 Mb-150 Mb |
| chr10: 33 Mb-34 Mb | chr14: 103 Mb-104 Mb | chr2: 165 Mb-166 Mb | chr4: 138 Mb-139 Mb | chr7: 150 Mb-151 Mb |
| chr10: 34 Mb-35 Mb | chr14: 104 Mb-105 Mb | chr2: 166 Mb-167 Mb | chr4: 139 Mb-140 Mb | chr7: 151 Mb-152 Mb |
| chr10: 35 Mb-36 Mb | chr14: 105 Mb-106 Mb | chr2: 167 Mb-168 Mb | chr4: 140 Mb-141 Mb | chr7: 152 Mb-153 Mb |
| chr10: 36 Mb-37 Mb | chr14: 106 Mb-107 Mb | chr2: 168 Mb-169 Mb | chr4: 141 Mb-142 Mb | chr7: 153 Mb-154 Mb |
| chr10: 37 Mb-38 Mb | chr14: 107 Mb-107349540 | chr2: 169 Mb-170 Mb | chr4: 142 Mb-143 Mb | chr7: 154 Mb-155 Mb |
| chr10: 38 Mb-39 Mb | chr15: 20 Mb-21 Mb | chr2: 170 Mb-171 Mb | chr4: 143 Mb-144 Mb | chr7: 155 Mb-156 Mb |
| chr10: 39 Mb-40 Mb | chr15: 21 Mb-22 Mb | chr2: 171 Mb-172 Mb | chr4: 144 Mb-145 Mb | chr7: 156 Mb-157 Mb |
| chr10: 42 Mb-43 Mb | chr15: 22 Mb-23 Mb | chr2: 172 Mb-173 Mb | chr4: 145 Mb-146 Mb | chr7: 157 Mb-158 Mb |
| chr10: 43 Mb-44 Mb | chr15: 23 Mb-24 Mb | chr2: 173 Mb-174 Mb | chr4: 146 Mb-147 Mb | chr7: 158 Mb-159 Mb |
| chr10: 44 Mb-45 Mb | chr15: 24 Mb-25 Mb | chr2: 174 Mb-175 Mb | chr4: 147 Mb-148 Mb | chr7: 159 Mb-159138663 |
| chr10: 45 Mb-46 Mb | chr15: 25 Mb-26 Mb | chr2: 175 Mb-176 Mb | chr4: 148 Mb-149 Mb | chr8: 0-1 Mb |
| chr10: 46 Mb-47 Mb | chr15: 26 Mb-27 Mb | chr2: 176 Mb-177 Mb | chr4: 149 Mb-150 Mb | chr8: 1 Mb-2 Mb |
| chr10: 47 Mb-48 Mb | chr15: 27 Mb-28 Mb | chr2: 177 Mb-178 Mb | chr4: 150 Mb-151 Mb | chr8: 2 Mb-3 Mb |
| chr10: 48 Mb-49 Mb | chr15: 28 Mb-29 Mb | chr2: 178 Mb-179 Mb | chr4: 151 Mb-152 Mb | chr8: 3 Mb-4 Mb |

TABLE 1-continued

| | | | | |
|---|---|---|---|---|
| chr10: 49 Mb-50 Mb | chr15: 29 Mb-30 Mb | chr2: 179 Mb-18 Mb0 | chr4: 152 Mb-153 Mb | chr8: 4 Mb-5 Mb |
| chr10: 50 Mb-51 Mb | chr15: 30 Mb-31 Mb | chr2: 18 Mb0-181 Mb | chr4: 153 Mb-154 Mb | chr8: 5 Mb-6 Mb |
| chr10: 51 Mb-52 Mb | chr15: 31 Mb-32 Mb | chr2: 181 Mb-182 Mb | chr4: 154 Mb-155 Mb | chr8: 6 Mb-7 Mb |
| chr10: 52 Mb-53 Mb | chr15: 32 Mb-33 Mb | chr2: 182 Mb-183 Mb | chr4: 155 Mb-156 Mb | chr8: 7 Mb-8 Mb |
| chr10: 53 Mb-54 Mb | chr15: 33 Mb-34 Mb | chr2: 183 Mb-184 Mb | chr4: 156 Mb-157 Mb | chr8: 8 Mb-9 Mb |
| chr10: 54 Mb-55 Mb | chr15: 34 Mb-35 Mb | chr2: 184 Mb-185 Mb | chr4: 157 Mb-158 Mb | chr8: 9 Mb-10 Mb |
| chr10: 55 Mb-56 Mb | chr15: 35 Mb-36 Mb | chr2: 185 Mb-186 Mb | chr4: 158 Mb-159 Mb | chr8: 10 Mb-11 Mb |
| chr10: 56 Mb-57 Mb | chr15: 36 Mb-37 Mb | chr2: 186 Mb-187 Mb | chr4: 159 Mb-160 Mb | chr8: 11 Mb-12 Mb |
| chr10: 57 Mb-58 Mb | chr15: 37 Mb-38 Mb | chr2: 187 Mb-188 Mb | chr4: 160 Mb-161 Mb | chr8: 12 Mb-13 Mb |
| chr10: 58 Mb-59 Mb | chr15: 38 Mb-39 Mb | chr2: 188 Mb-189 Mb | chr4: 161 Mb-162 Mb | chr8: 13 Mb-14 Mb |
| chr10: 59 Mb-60 Mb | chr15: 39 Mb-40 Mb | chr2: 189 Mb-190 Mb | chr4: 162 Mb-163 Mb | chr8: 14 Mb-15 Mb |
| chr10: 60 Mb-61 Mb | chr15: 40 Mb-41 Mb | chr2: 190 Mb-191 Mb | chr4: 163 Mb-164 Mb | chr8: 15 Mb-16 Mb |
| chr10: 61 Mb-62 Mb | chr15: 41 Mb-42 Mb | chr2: 191 Mb-192 Mb | chr4: 164 Mb-165 Mb | chr8: 16 Mb-17 Mb |
| chr10: 62 Mb-63 Mb | chr15: 42 Mb-43 Mb | chr2: 192 Mb-193 Mb | chr4: 165 Mb-166 Mb | chr8: 17 Mb-18 Mb |
| chr10: 63 Mb-64 Mb | chr15: 43 Mb-44 Mb | chr2: 193 Mb-194 Mb | chr4: 166 Mb-167 Mb | chr8: 18 Mb-19 Mb |
| chr10: 64 Mb-65 Mb | chr15: 44 Mb-45 Mb | chr2: 194 Mb-195 Mb | chr4: 167 Mb-168 Mb | chr8: 19 Mb-20 Mb |
| chr10: 65 Mb-66 Mb | chr15: 45 Mb-46 Mb | chr2: 195 Mb-196 Mb | chr4: 168 Mb-169 Mb | chr8: 20 Mb-21 Mb |
| chr10: 66 Mb-67 Mb | chr15: 46 Mb-47 Mb | chr2: 196 Mb-197 Mb | chr4: 169 Mb-170 Mb | chr8: 21 Mb-22 Mb |
| chr10: 67 Mb-68 Mb | chr15: 47 Mb-48 Mb | chr2: 197 Mb-198 Mb | chr4: 170 Mb-171 Mb | chr8: 22 Mb-23 Mb |
| chr10: 68 Mb-69 Mb | chr15: 48 Mb-49 Mb | chr2: 198 Mb-199 Mb | chr4: 171 Mb-172 Mb | chr8: 23 Mb-24 Mb |
| chr10: 69 Mb-70 Mb | chr15: 49 Mb-50 Mb | chr2: 199 Mb-20 Mb0 | chr4: 172 Mb-173 Mb | chr8: 24 Mb-25 Mb |
| chr10: 70 Mb-71 Mb | chr15: 50 Mb-51 Mb | chr2: 20 Mb0-201 Mb | chr4: 173 Mb-174 Mb | chr8: 25 Mb-26 Mb |
| chr10: 71 Mb-72 Mb | chr15: 51 Mb-52 Mb | chr2: 201 Mb-202 Mb | chr4: 174 Mb-175 Mb | chr8: 26 Mb-27 Mb |
| chr10: 72 Mb-73 Mb | chr15: 52 Mb-53 Mb | chr2: 202 Mb-203 Mb | chr4: 175 Mb-176 Mb | chr8: 27 Mb-28 Mb |
| chr10: 73 Mb-74 Mb | chr15: 53 Mb-54 Mb | chr2: 203 Mb-204 Mb | chr4: 176 Mb-177 Mb | chr8: 28 Mb-29 Mb |
| chr10: 74 Mb-75 Mb | chr15: 54 Mb-55 Mb | chr2: 204 Mb-205 Mb | chr4: 177 Mb-178 Mb | chr8: 29 Mb-30 Mb |
| chr10: 75 Mb-76 Mb | chr15: 55 Mb-56 Mb | chr2: 205 Mb-206 Mb | chr4: 178 Mb-179 Mb | chr8: 30 Mb-31 Mb |
| chr10: 76 Mb-77 Mb | chr15: 56 Mb-57 Mb | chr2: 206 Mb-207 Mb | chr4: 179 Mb-18 Mb0 | chr8: 31 Mb-32 Mb |
| chr10: 77 Mb-78 Mb | chr15: 57 Mb-58 Mb | chr2: 207 Mb-208 Mb | chr4: 18 Mb0-181 Mb | chr8: 32 Mb-33 Mb |
| chr10: 78 Mb-79 Mb | chr15: 58 Mb-59 Mb | chr2: 208 Mb-209 Mb | chr4: 181 Mb-182 Mb | chr8: 33 Mb-34 Mb |
| chr10: 79 Mb-8 Mb0 | chr15: 59 Mb-60 Mb | chr2: 209 Mb-210 Mb | chr4: 182 Mb-183 Mb | chr8: 34 Mb-35 Mb |
| chr10: 8 Mb0-81 Mb | chr15: 60 Mb-61 Mb | chr2: 210 Mb-211 Mb | chr4: 183 Mb-184 Mb | chr8: 35 Mb-36 Mb |
| chr10: 81 Mb-82 Mb | chr15: 61 Mb-62 Mb | chr2: 211 Mb-212 Mb | chr4: 184 Mb-185 Mb | chr8: 36 Mb-37 Mb |
| chr10: 82 Mb-83 Mb | chr15: 62 Mb-63 Mb | chr2: 212 Mb-213 Mb | chr4: 185 Mb-186 Mb | chr8: 37 Mb-38 Mb |
| chr10: 83 Mb-84 Mb | chr15: 63 Mb-64 Mb | chr2: 213 Mb-214 Mb | chr4: 186 Mb-187 Mb | chr8: 38 Mb-39 Mb |
| chr10: 84 Mb-85 Mb | chr15: 64 Mb-65 Mb | chr2: 214 Mb-215 Mb | chr4: 187 Mb-188 Mb | chr8: 39 Mb-40 Mb |
| chr10: 85 Mb-86 Mb | chr15: 65 Mb-66 Mb | chr2: 215 Mb-216 Mb | chr4: 188 Mb-189 Mb | chr8: 40 Mb-41 Mb |
| chr10: 86 Mb-87 Mb | chr15: 66 Mb-67 Mb | chr2: 216 Mb-217 Mb | chr4: 189 Mb-190 Mb | chr8: 41 Mb-42 Mb |
| chr10: 87 Mb-88 Mb | chr15: 67 Mb-68 Mb | chr2: 217 Mb-218 Mb | chr4: 190 Mb-191 Mb | chr8: 42 Mb-43 Mb |
| chr10: 88 Mb-89 Mb | chr15: 68 Mb-69 Mb | chr2: 218 Mb-219 Mb | chr4: 191 Mb-191154276 | chr8: 43 Mb-44 Mb |
| chr10: 89 Mb-90 Mb | chr15: 69 Mb-70 Mb | chr2: 219 Mb-220 Mb | chr5: 0-1 Mb | chr8: 47 Mb-48 Mb |
| chr10: 90 Mb-91 Mb | chr15: 70 Mb-71 Mb | chr2: 220 Mb-221 Mb | chr5: 1 Mb-2 Mb | chr8: 48 Mb-49 Mb |
| chr10: 91 Mb-92 Mb | chr15: 71 Mb-72 Mb | chr2: 221 Mb-222 Mb | chr5: 2 Mb-3 Mb | chr8: 49 Mb-50 Mb |
| chr10: 92 Mb-93 Mb | chr15: 72 Mb-73 Mb | chr2: 222 Mb-223 Mb | chr5: 3 Mb-4 Mb | chr8: 50 Mb-51 Mb |
| chr10: 93 Mb-94 Mb | chr15: 73 Mb-74 Mb | chr2: 223 Mb-224 Mb | chr5: 4 Mb-5 Mb | chr8: 51 Mb-52 Mb |
| chr10: 94 Mb-95 Mb | chr15: 74 Mb-75 Mb | chr2: 224 Mb-225 Mb | chr5: 5 Mb-6 Mb | chr8: 52 Mb-53 Mb |
| chr10: 95 Mb-96 Mb | chr15: 75 Mb-76 Mb | chr2: 225 Mb-226 Mb | chr5: 6 Mb-7 Mb | chr8: 53 Mb-54 Mb |
| chr10: 96 Mb-97 Mb | chr15: 76 Mb-77 Mb | chr2: 226 Mb-227 Mb | chr5: 7 Mb-8 Mb | chr8: 54 Mb-55 Mb |
| chr10: 97 Mb-98 Mb | chr15: 77 Mb-78 Mb | chr2: 227 Mb-228 Mb | chr5: 8 Mb-9 Mb | chr8: 55 Mb-56 Mb |
| chr10: 98 Mb-99 Mb | chr15: 78 Mb-79 Mb | chr2: 228 Mb-229 Mb | chr5: 9 Mb-10 Mb | chr8: 56 Mb-57 Mb |
| chr10: 99 Mb-100 Mb | chr15: 79 Mb-8 Mb0 | chr2: 229 Mb-230 Mb | chr5: 10 Mb-11 Mb | chr8: 57 Mb-58 Mb |
| chr10: 100 Mb-101 Mb | chr15: 8 Mb0-81 Mb | chr2: 230 Mb-231 Mb | chr5: 11 Mb-12 Mb | chr8: 58 Mb-59 Mb |
| chr10: 101 Mb-102 Mb | chr15: 81 Mb-82 Mb | chr2: 231 Mb-232 Mb | chr5: 12 Mb-13 Mb | chr8: 59 Mb-60 Mb |
| chr10: 102 Mb-103 Mb | chr15: 82 Mb-83 Mb | chr2: 232 Mb-233 Mb | chr5: 13 Mb-14 Mb | chr8: 60 Mb-61 Mb |
| chr10: 103 Mb-104 Mb | chr15: 83 Mb-84 Mb | chr2: 233 Mb-234 Mb | chr5: 14 Mb-15 Mb | chr8: 61 Mb-62 Mb |
| chr10: 104 Mb-105 Mb | chr15: 84 Mb-85 Mb | chr2: 234 Mb-235 Mb | chr5: 15 Mb-16 Mb | chr8: 62 Mb-63 Mb |
| chr10: 105 Mb-106 Mb | chr15: 85 Mb-86 Mb | chr2: 235 Mb-236 Mb | chr5: 16 Mb-17 Mb | chr8: 63 Mb-64 Mb |
| chr10: 106 Mb-107 Mb | chr15: 86 Mb-87 Mb | chr2: 236 Mb-237 Mb | chr5: 17 Mb-18 Mb | chr8: 64 Mb-65 Mb |
| chr10: 107 Mb-108 Mb | chr15: 87 Mb-88 Mb | chr2: 237 Mb-238 Mb | chr5: 18 Mb-19 Mb | chr8: 65 Mb-66 Mb |
| chr10: 108 Mb-109 Mb | chr15: 88 Mb-89 Mb | chr2: 238 Mb-239 Mb | chr5: 19 Mb-20 Mb | chr8: 66 Mb-67 Mb |
| chr10: 109 Mb-110 Mb | chr15: 89 Mb-90 Mb | chr2: 239 Mb-240 Mb | chr5: 20 Mb-21 Mb | chr8: 67 Mb-68 Mb |
| chr10: 110 Mb-111 Mb | chr15: 90 Mb-91 Mb | chr2: 240 Mb-241 Mb | chr5: 21 Mb-22 Mb | chr8: 68 Mb-69 Mb |
| chr10: 111 Mb-112 Mb | chr15: 91 Mb-92 Mb | chr2: 241 Mb-242 Mb | chr5: 22 Mb-23 Mb | chr8: 69 Mb-70 Mb |
| chr10: 112 Mb-113 Mb | chr15: 92 Mb-93 Mb | chr2: 242 Mb-243 Mb | chr5: 23 Mb-24 Mb | chr8: 70 Mb-71 Mb |
| chr10: 113 Mb-114 Mb | chr15: 93 Mb-94 Mb | chr2: 243 Mb-243199373 | chr5: 24 Mb-25 Mb | chr8: 71 Mb-72 Mb |
| chr10: 114 Mb-115 Mb | chr15: 94 Mb-95 Mb | chr20: 0-1 Mb | chr5: 25 Mb-26 Mb | chr8: 72 Mb-73 Mb |
| chr10: 115 Mb-116 Mb | chr15: 95 Mb-96 Mb | chr20: 1 Mb-2 Mb | chr5: 26 Mb-27 Mb | chr8: 73 Mb-74 Mb |
| chr10: 116 Mb-117 Mb | chr15: 96 Mb-97 Mb | chr20: 2 Mb-3 Mb | chr5: 27 Mb-28 Mb | chr8: 74 Mb-75 Mb |
| chr10: 117 Mb-118 Mb | chr15: 97 Mb-98 Mb | chr20: 3 Mb-4 Mb | chr5: 28 Mb-29 Mb | chr8: 75 Mb-76 Mb |
| chr10: 118 Mb-119 Mb | chr15: 98 Mb-99 Mb | chr20: 4 Mb-5 Mb | chr5: 29 Mb-30 Mb | chr8: 76 Mb-77 Mb |
| chr10: 119 Mb-120 Mb | chr15: 99 Mb-100 Mb | chr20: 5 Mb-6 Mb | chr5: 30 Mb-31 Mb | chr8: 77 Mb-78 Mb |
| chr10: 120 Mb-121 Mb | chr15: 100 Mb-101 Mb | chr20: 6 Mb-7 Mb | chr5: 31 Mb-32 Mb | chr8: 78 Mb-79 Mb |
| chr10: 121 Mb-122 Mb | chr15: 101 Mb-102 Mb | chr20: 7 Mb-8 Mb | chr5: 32 Mb-33 Mb | chr8: 79 Mb-8 Mb0 |
| chr10: 122 Mb-123 Mb | chr15: 102 Mb-102531392 | chr20: 8 Mb-9 Mb | chr5: 33 Mb-34 Mb | chr8: 8 Mb0-81 Mb |
| chr10: 123 Mb-124 Mb | chr16: 0-1 Mb | chr20: 9 Mb-10 Mb | chr5: 34 Mb-35 Mb | chr8: 81 Mb-82 Mb |
| chr10: 124 Mb-125 Mb | chr16: 1 Mb-2 Mb | chr20: 10 Mb-11 Mb | chr5: 35 Mb-36 Mb | chr8: 82 Mb-83 Mb |
| chr10: 125 Mb-126 Mb | chr16: 2 Mb-3 Mb | chr20: 11 Mb-12 Mb | chr5: 36 Mb-37 Mb | chr8: 83 Mb-84 Mb |
| chr10: 126 Mb-127 Mb | chr16: 3 Mb-4 Mb | chr20: 12 Mb-13 Mb | chr5: 37 Mb-38 Mb | chr8: 84 Mb-85 Mb |
| chr10: 127 Mb-128 Mb | chr16: 4 Mb-5 Mb | chr20: 13 Mb-14 Mb | chr5: 38 Mb-39 Mb | chr8: 85 Mb-86 Mb |
| chr10: 128 Mb-129 Mb | chr16: 5 Mb-6 Mb | chr20: 14 Mb-15 Mb | chr5: 39 Mb-40 Mb | chr8: 86 Mb-87 Mb |

TABLE 1-continued

| | | | | |
|---|---|---|---|---|
| chr10: 129 Mb-130 Mb | chr16: 6 Mb-7 Mb | chr20: 15 Mb-16 Mb | chr5: 40 Mb-41 Mb | chr8: 87 Mb-88 Mb |
| chr10: 130 Mb-131 Mb | chr16: 7 Mb-8 Mb | chr20: 16 Mb-17 Mb | chr5: 41 Mb-42 Mb | chr8: 88 Mb-89 Mb |
| chr10: 131 Mb-132 Mb | chr16: 8 Mb-9 Mb | chr20: 17 Mb-18 Mb | chr5: 42 Mb-43 Mb | chr8: 89 Mb-90 Mb |
| chr10: 132 Mb-133 Mb | chr16: 9 Mb-10 Mb | chr20: 18 Mb-19 Mb | chr5: 43 Mb-44 Mb | chr8: 90 Mb-91 Mb |
| chr10: 133 Mb-134 Mb | chr16: 10 Mb-11 Mb | chr20: 19 Mb-20 Mb | chr5: 44 Mb-45 Mb | chr8: 91 Mb-92 Mb |
| chr10: 134 Mb-135 Mb | chr16: 11 Mb-12 Mb | chr20: 20 Mb-21 Mb | chr5: 45 Mb-46 Mb | chr8: 92 Mb-93 Mb |
| chr10: 135 Mb-135534747 | chr16: 12 Mb-13 Mb | chr20: 21 Mb-22 Mb | chr5: 49 Mb-50 Mb | chr8: 93 Mb-94 Mb |
| chr11: 0-1 Mb | chr16: 13 Mb-14 Mb | chr20: 22 Mb-23 Mb | chr5: 50 Mb-51 Mb | chr8: 94 Mb-95 Mb |
| chr11: 1 Mb-2 Mb | chr16: 14 Mb-15 Mb | chr20: 23 Mb-24 Mb | chr5: 51 Mb-52 Mb | chr8: 95 Mb-96 Mb |
| chr11: 2 Mb-3 Mb | chr16: 15 Mb-16 Mb | chr20: 24 Mb-25 Mb | chr5: 52 Mb-53 Mb | chr8: 96 Mb-97 Mb |
| chr11: 3 Mb-4 Mb | chr16: 16 Mb-17 Mb | chr20: 25 Mb-26 Mb | chr5: 53 Mb-54 Mb | chr8: 97 Mb-98 Mb |
| chr11: 4 Mb-5 Mb | chr16: 17 Mb-18 Mb | chr20: 26 Mb-27 Mb | chr5: 54 Mb-55 Mb | chr8: 98 Mb-99 Mb |
| chr11: 5 Mb-6 Mb | chr16: 18 Mb-19 Mb | chr20: 29 Mb-30 Mb | chr5: 55 Mb-56 Mb | chr8: 99 Mb-100 Mb |
| chr11: 6 Mb-7 Mb | chr16: 19 Mb-20 Mb | chr20: 30 Mb-31 Mb | chr5: 56 Mb-57 Mb | chr8: 100 Mb-101 Mb |
| chr11: 7 Mb-8 Mb | chr16: 20 Mb-21 Mb | chr20: 31 Mb-32 Mb | chr5: 57 Mb-58 Mb | chr8: 101 Mb-102 Mb |
| chr11: 8 Mb-9 Mb | chr16: 21 Mb-22 Mb | chr20: 32 Mb-33 Mb | chr5: 58 Mb-59 Mb | chr8: 102 Mb-103 Mb |
| chr11: 9 Mb-10 Mb | chr16: 22 Mb-23 Mb | chr20: 33 Mb-34 Mb | chr5: 59 Mb-60 Mb | chr8: 103 Mb-104 Mb |
| chr11: 10 Mb-11 Mb | chr16: 23 Mb-24 Mb | chr20: 34 Mb-35 Mb | chr5: 60 Mb-61 Mb | chr8: 104 Mb-105 Mb |
| chr11: 11 Mb-12 Mb | chr16: 24 Mb-25 Mb | chr20: 35 Mb-36 Mb | chr5: 61 Mb-62 Mb | chr8: 105 Mb-106 Mb |
| chr11: 12 Mb-13 Mb | chr16: 25 Mb-26 Mb | chr20: 36 Mb-37 Mb | chr5: 62 Mb-63 Mb | chr8: 106 Mb-107 Mb |
| chr11: 13 Mb-14 Mb | chr16: 26 Mb-27 Mb | chr20: 37 Mb-38 Mb | chr5: 63 Mb-64 Mb | chr8: 107 Mb-108 Mb |
| chr11: 14 Mb-15 Mb | chr16: 27 Mb-28 Mb | chr20: 38 Mb-39 Mb | chr5: 64 Mb-65 Mb | chr8: 108 Mb-109 Mb |
| chr11: 15 Mb-16 Mb | chr16: 28 Mb-29 Mb | chr20: 39 Mb-40 Mb | chr5: 65 Mb-66 Mb | chr8: 109 Mb-110 Mb |
| chr11: 16 Mb-17 Mb | chr16: 29 Mb-30 Mb | chr20: 40 Mb-41 Mb | chr5: 66 Mb-67 Mb | chr8: 110 Mb-111 Mb |
| chr11: 17 Mb-18 Mb | chr16: 30 Mb-31 Mb | chr20: 41 Mb-42 Mb | chr5: 67 Mb-68 Mb | chr8: 111 Mb-112 Mb |
| chr11: 18 Mb-19 Mb | chr16: 31 Mb-32 Mb | chr20: 42 Mb-43 Mb | chr5: 68 Mb-69 Mb | chr8: 112 Mb-113 Mb |
| chr11: 19 Mb-20 Mb | chr16: 32 Mb-33 Mb | chr20: 43 Mb-44 Mb | chr5: 69 Mb-70 Mb | chr8: 113 Mb-114 Mb |
| chr11: 20 Mb-21 Mb | chr16: 33 Mb-34 Mb | chr20: 44 Mb-45 Mb | chr5: 70 Mb-71 Mb | chr8: 114 Mb-115 Mb |
| chr11: 21 Mb-22 Mb | chr16: 34 Mb-35 Mb | chr20: 45 Mb-46 Mb | chr5: 71 Mb-72 Mb | chr8: 115 Mb-116 Mb |
| chr11: 22 Mb-23 Mb | chr16: 35 Mb-36 Mb | chr20: 46 Mb-47 Mb | chr5: 72 Mb-73 Mb | chr8: 116 Mb-117 Mb |
| chr11: 23 Mb-24 Mb | chr16: 46 Mb-47 Mb | chr20: 47 Mb-48 Mb | chr5: 73 Mb-74 Mb | chr8: 117 Mb-118 Mb |
| chr11: 24 Mb-25 Mb | chr16: 47 Mb-48 Mb | chr20: 48 Mb-49 Mb | chr5: 74 Mb-75 Mb | chr8: 118 Mb-119 Mb |
| chr11: 25 Mb-26 Mb | chr16: 48 Mb-49 Mb | chr20: 49 Mb-50 Mb | chr5: 75 Mb-76 Mb | chr8: 119 Mb-120 Mb |
| chr11: 26 Mb-27 Mb | chr16: 49 Mb-50 Mb | chr20: 50 Mb-51 Mb | chr5: 76 Mb-77 Mb | chr8: 120 Mb-121 Mb |
| chr11: 27 Mb-28 Mb | chr16: 50 Mb-51 Mb | chr20: 51 Mb-52 Mb | chr5: 77 Mb-78 Mb | chr8: 121 Mb-122 Mb |
| chr11: 28 Mb-29 Mb | chr16: 51 Mb-52 Mb | chr20: 52 Mb-53 Mb | chr5: 78 Mb-79 Mb | chr8: 122 Mb-123 Mb |
| chr11: 29 Mb-30 Mb | chr16: 52 Mb-53 Mb | chr20: 53 Mb-54 Mb | chr5: 79 Mb-8 Mb0 | chr8: 123 Mb-124 Mb |
| chr11: 30 Mb-31 Mb | chr16: 53 Mb-54 Mb | chr20: 54 Mb-55 Mb | chr5: 8 Mb0-81 Mb | chr8: 124 Mb-125 Mb |
| chr11: 31 Mb-32 Mb | chr16: 54 Mb-55 Mb | chr20: 55 Mb-56 Mb | chr5: 81 Mb-82 Mb | chr8: 125 Mb-126 Mb |
| chr11: 32 Mb-33 Mb | chr16: 55 Mb-56 Mb | chr20: 56 Mb-57 Mb | chr5: 82 Mb-83 Mb | chr8: 126 Mb-127 Mb |
| chr11: 33 Mb-34 Mb | chr16: 56 Mb-57 Mb | chr20: 57 Mb-58 Mb | chr5: 83 Mb-84 Mb | chr8: 127 Mb-128 Mb |
| chr11: 34 Mb-35 Mb | chr16: 57 Mb-58 Mb | chr20: 58 Mb-59 Mb | chr5: 84 Mb-85 Mb | chr8: 128 Mb-129 Mb |
| chr11: 35 Mb-36 Mb | chr16: 58 Mb-59 Mb | chr20: 59 Mb-60 Mb | chr5: 85 Mb-86 Mb | chr8: 129 Mb-130 Mb |
| chr11: 36 Mb-37 Mb | chr16: 59 Mb-60 Mb | chr20: 60 Mb-61 Mb | chr5: 86 Mb-87 Mb | chr8: 130 Mb-131 Mb |
| chr11: 37 Mb-38 Mb | chr16: 60 Mb-61 Mb | chr20: 61 Mb-62 Mb | chr5: 87 Mb-88 Mb | chr8: 131 Mb-132 Mb |
| chr11: 38 Mb-39 Mb | chr16: 61 Mb-62 Mb | chr20: 62 Mb-63 Mb | chr5: 88 Mb-89 Mb | chr8: 132 Mb-133 Mb |
| chr11: 39 Mb-40 Mb | chr16: 62 Mb-63 Mb | chr21: 9 Mb-10 Mb | chr5: 89 Mb-90 Mb | chr8: 133 Mb-134 Mb |
| chr11: 40 Mb-41 Mb | chr16: 63 Mb-64 Mb | chr21: 10 Mb-11 Mb | chr5: 90 Mb-91 Mb | chr8: 134 Mb-135 Mb |
| chr11: 41 Mb-42 Mb | chr16: 64 Mb-65 Mb | chr21: 11 Mb-12 Mb | chr5: 91 Mb-92 Mb | chr8: 135 Mb-136 Mb |
| chr11: 42 Mb-43 Mb | chr16: 65 Mb-66 Mb | chr21: 14 Mb-15 Mb | chr5: 92 Mb-93 Mb | chr8: 136 Mb-137 Mb |
| chr11: 43 Mb-44 Mb | chr16: 66 Mb-67 Mb | chr21: 15 Mb-16 Mb | chr5: 93 Mb-94 Mb | chr8: 137 Mb-138 Mb |
| chr11: 44 Mb-45 Mb | chr16: 67 Mb-68 Mb | chr21: 16 Mb-17 Mb | chr5: 94 Mb-95 Mb | chr8: 138 Mb-139 Mb |
| chr11: 45 Mb-46 Mb | chr16: 68 Mb-69 Mb | chr21: 17 Mb-18 Mb | chr5: 95 Mb-96 Mb | chr8: 139 Mb-140 Mb |
| chr11: 46 Mb-47 Mb | chr16: 69 Mb-70 Mb | chr21: 18 Mb-19 Mb | chr5: 96 Mb-97 Mb | chr8: 140 Mb-141 Mb |
| chr11: 47 Mb-48 Mb | chr16: 70 Mb-71 Mb | chr21: 19 Mb-20 Mb | chr5: 97 Mb-98 Mb | chr8: 141 Mb-142 Mb |
| chr11: 48 Mb-49 Mb | chr16: 71 Mb-72 Mb | chr21: 20 Mb-21 Mb | chr5: 98 Mb-99 Mb | chr8: 142 Mb-143 Mb |
| chr11: 49 Mb-50 Mb | chr16: 72 Mb-73 Mb | chr21: 21 Mb-22 Mb | chr5: 99 Mb-100 Mb | chr8: 143 Mb-144 Mb |
| chr11: 50 Mb-51 Mb | chr16: 73 Mb-74 Mb | chr21: 22 Mb-23 Mb | chr5: 100 Mb-101 Mb | chr8: 144 Mb-145 Mb |
| chr11: 51 Mb-52 Mb | chr16: 74 Mb-75 Mb | chr21: 23 Mb-24 Mb | chr5: 101 Mb-102 Mb | chr8: 145 Mb-146 Mb |
| chr11: 55 Mb-56 Mb | chr16: 75 Mb-76 Mb | chr21: 24 Mb-25 Mb | chr5: 102 Mb-103 Mb | chr8: 146 Mb-146364022 |
| chr11: 56 Mb-57 Mb | chr16: 76 Mb-77 Mb | chr21: 25 Mb-26 Mb | chr5: 103 Mb-104 Mb | chr9: 0-1 Mb |
| chr11: 57 Mb-58 Mb | chr16: 77 Mb-78 Mb | chr21: 26 Mb-27 Mb | chr5: 104 Mb-105 Mb | chr9: 1 Mb-2 Mb |
| chr11: 58 Mb-59 Mb | chr16: 78 Mb-79 Mb | chr21: 27 Mb-28 Mb | chr5: 105 Mb-106 Mb | chr9: 2 Mb-3 Mb |
| chr11: 59 Mb-60 Mb | chr16: 79 Mb-8 Mb0 | chr21: 28 Mb-29 Mb | chr5: 106 Mb-107 Mb | chr9: 3 Mb-4 Mb |
| chr11: 60 Mb-61 Mb | chr16: 8 Mb0-81 Mb | chr21: 29 Mb-30 Mb | chr5: 107 Mb-108 Mb | chr9: 4 Mb-5 Mb |
| chr11: 61 Mb-62 Mb | chr16: 81 Mb-82 Mb | chr21: 30 Mb-31 Mb | chr5: 108 Mb-109 Mb | chr9: 5 Mb-6 Mb |
| chr11: 62 Mb-63 Mb | chr16: 82 Mb-83 Mb | chr21: 31 Mb-32 Mb | chr5: 109 Mb-110 Mb | chr9: 6 Mb-7 Mb |
| chr11: 63 Mb-64 Mb | chr16: 83 Mb-84 Mb | chr21: 32 Mb-33 Mb | chr5: 110 Mb-111 Mb | chr9: 7 Mb-8 Mb |
| chr11: 64 Mb-65 Mb | chr16: 84 Mb-85 Mb | chr21: 33 Mb-34 Mb | chr5: 111 Mb-112 Mb | chr9: 8 Mb-9 Mb |
| chr11: 65 Mb-66 Mb | chr16: 85 Mb-86 Mb | chr21: 34 Mb-35 Mb | chr5: 112 Mb-113 Mb | chr9: 9 Mb-10 Mb |
| chr11: 66 Mb-67 Mb | chr16: 86 Mb-87 Mb | chr21: 35 Mb-36 Mb | chr5: 113 Mb-114 Mb | chr9: 10 Mb-11 Mb |
| chr11: 67 Mb-68 Mb | chr16: 87 Mb-88 Mb | chr21: 36 Mb-37 Mb | chr5: 114 Mb-115 Mb | chr9: 11 Mb-12 Mb |
| chr11: 68 Mb-69 Mb | chr16: 88 Mb-89 Mb | chr21: 37 Mb-38 Mb | chr5: 115 Mb-116 Mb | chr9: 12 Mb-13 Mb |
| chr11: 69 Mb-70 Mb | chr16: 89 Mb-90 Mb | chr21: 38 Mb-39 Mb | chr5: 116 Mb-117 Mb | chr9: 13 Mb-14 Mb |
| chr11: 70 Mb-71 Mb | chr16: 90 Mb-90354753 | chr21: 39 Mb-40 Mb | chr5: 117 Mb-118 Mb | chr9: 14 Mb-15 Mb |
| chr11: 71 Mb-72 Mb | chr17: 0-1 Mb | chr21: 40 Mb-41 Mb | chr5: 118 Mb-119 Mb | chr9: 15 Mb-16 Mb |
| chr11: 72 Mb-73 Mb | chr17: 1 Mb-2 Mb | chr21: 41 Mb-42 Mb | chr5: 119 Mb-120 Mb | chr9: 16 Mb-17 Mb |
| chr11: 73 Mb-74 Mb | chr17: 2 Mb-3 Mb | chr21: 42 Mb-43 Mb | chr5: 120 Mb-121 Mb | chr9: 17 Mb-18 Mb |
| chr11: 74 Mb-75 Mb | chr17: 3 Mb-4 Mb | chr21: 43 Mb-44 Mb | chr5: 121 Mb-122 Mb | chr9: 18 Mb-19 Mb |
| chr11: 75 Mb-76 Mb | chr17: 4 Mb-5 Mb | chr21: 44 Mb-45 Mb | chr5: 122 Mb-123 Mb | chr9: 19 Mb-20 Mb |

TABLE 1-continued

| | | | | |
|---|---|---|---|---|
| chr11: 76 Mb-77 Mb | chr17: 5 Mb-6 Mb | chr21: 45 Mb-46 Mb | chr5: 123 Mb-124 Mb | chr9: 20 Mb-21 Mb |
| chr11: 77 Mb-78 Mb | chr17: 6 Mb-7 Mb | chr21: 46 Mb-47 Mb | chr5: 124 Mb-125 Mb | chr9: 21 Mb-22 Mb |
| chr11: 78 Mb-79 Mb | chr17: 7 Mb-8 Mb | chr21: 47 Mb-48 Mb | chr5: 125 Mb-126 Mb | chr9: 22 Mb-23 Mb |
| chr11: 79 Mb-8 Mb0 | chr17: 8 Mb-9 Mb | chr21: 48 Mb-48129895 | chr5: 126 Mb-127 Mb | chr9: 23 Mb-24 Mb |
| chr11: 8 Mb0-81 Mb | chr17: 9 Mb-10 Mb | chr22: 16 Mb-17 Mb | chr5: 127 Mb-128 Mb | chr9: 24 Mb-25 Mb |
| chr11: 81 Mb-82 Mb | chr17: 10 Mb-11 Mb | chr22: 17 Mb-18 Mb | chr5: 128 Mb-129 Mb | chr9: 25 Mb-26 Mb |
| chr11: 82 Mb-83 Mb | chr17: 11 Mb-12 Mb | chr22: 18 Mb-19 Mb | chr5: 129 Mb-130 Mb | chr9: 26 Mb-27 Mb |
| chr11: 83 Mb-84 Mb | chr17: 12 Mb-13 Mb | chr22: 19 Mb-20 Mb | chr5: 130 Mb-131 Mb | chr9: 27 Mb-28 Mb |
| chr11: 84 Mb-85 Mb | chr17: 13 Mb-14 Mb | chr22: 20 Mb-21 Mb | chr5: 131 Mb-132 Mb | chr9: 28 Mb-29 Mb |
| chr11: 85 Mb-86 Mb | chr17: 14 Mb-15 Mb | chr22: 21 Mb-22 Mb | chr5: 132 Mb-133 Mb | chr9: 29 Mb-30 Mb |
| chr11: 86 Mb-87 Mb | chr17: 15 Mb-16 Mb | chr22: 22 Mb-23 Mb | chr5: 133 Mb-134 Mb | chr9: 30 Mb-31 Mb |
| chr11: 87 Mb-88 Mb | chr17: 16 Mb-17 Mb | chr22: 23 Mb-24 Mb | chr5: 134 Mb-135 Mb | chr9: 31 Mb-32 Mb |
| chr11: 88 Mb-89 Mb | chr17: 17 Mb-18 Mb | chr22: 24 Mb-25 Mb | chr5: 135 Mb-136 Mb | chr9: 32 Mb-33 Mb |
| chr11: 89 Mb-90 Mb | chr17: 18 Mb-19 Mb | chr22: 25 Mb-26 Mb | chr5: 136 Mb-137 Mb | chr9: 33 Mb-34 Mb |
| chr11: 90 Mb-91 Mb | chr17: 19 Mb-20 Mb | chr22: 26 Mb-27 Mb | chr5: 137 Mb-138 Mb | chr9: 34 Mb-35 Mb |
| chr11: 91 Mb-92 Mb | chr17: 20 Mb-21 Mb | chr22: 27 Mb-28 Mb | chr5: 138 Mb-139 Mb | chr9: 35 Mb-36 Mb |
| chr11: 92 Mb-93 Mb | chr17: 21 Mb-22 Mb | chr22: 28 Mb-29 Mb | chr5: 139 Mb-140 Mb | chr9: 36 Mb-37 Mb |
| chr11: 93 Mb-94 Mb | chr17: 22 Mb-23 Mb | chr22: 29 Mb-30 Mb | chr5: 140 Mb-141 Mb | chr9: 37 Mb-38 Mb |
| chr11: 94 Mb-95 Mb | chr17: 25 Mb-26 Mb | chr22: 30 Mb-31 Mb | chr5: 141 Mb-142 Mb | chr9: 38 Mb-39 Mb |
| chr11: 95 Mb-96 Mb | chr17: 26 Mb-27 Mb | chr22: 31 Mb-32 Mb | chr5: 142 Mb-143 Mb | chr9: 39 Mb-40 Mb |
| chr11: 96 Mb-97 Mb | chr17: 27 Mb-28 Mb | chr22: 32 Mb-33 Mb | chr5: 143 Mb-144 Mb | chr9: 40 Mb-41 Mb |
| chr11: 97 Mb-98 Mb | chr17: 28 Mb-29 Mb | chr22: 33 Mb-34 Mb | chr5: 144 Mb-145 Mb | chr9: 41 Mb-42 Mb |
| chr11: 98 Mb-99 Mb | chr17: 29 Mb-30 Mb | chr22: 34 Mb-35 Mb | chr5: 145 Mb-146 Mb | chr9: 42 Mb-43 Mb |
| chr11: 99 Mb-100 Mb | chr17: 30 Mb-31 Mb | chr22: 35 Mb-36 Mb | chr5: 146 Mb-147 Mb | chr9: 43 Mb-44 Mb |
| chr11: 100 Mb-101 Mb | chr17: 31 Mb-32 Mb | chr22: 36 Mb-37 Mb | chr5: 147 Mb-148 Mb | chr9: 44 Mb-45 Mb |
| chr11: 101 Mb-102 Mb | chr17: 32 Mb-33 Mb | chr22: 37 Mb-38 Mb | chr5: 148 Mb-149 Mb | chr9: 45 Mb-46 Mb |
| chr11: 102 Mb-103 Mb | chr17: 33 Mb-34 Mb | chr22: 38 Mb-39 Mb | chr5: 149 Mb-150 Mb | chr9: 46 Mb-47 Mb |
| chr11: 103 Mb-104 Mb | chr17: 34 Mb-35 Mb | chr22: 39 Mb-40 Mb | chr5: 150 Mb-151 Mb | chr9: 47 Mb-48 Mb |
| chr11: 104 Mb-105 Mb | chr17: 35 Mb-36 Mb | chr22: 40 Mb-41 Mb | chr5: 151 Mb-152 Mb | chr9: 65 Mb-66 Mb |
| chr11: 105 Mb-106 Mb | chr17: 36 Mb-37 Mb | chr22: 41 Mb-42 Mb | chr5: 152 Mb-153 Mb | chr9: 66 Mb-67 Mb |
| chr11: 106 Mb-107 Mb | chr17: 37 Mb-38 Mb | chr22: 42 Mb-43 Mb | chr5: 153 Mb-154 Mb | chr9: 67 Mb-68 Mb |
| chr11: 107 Mb-108 Mb | chr17: 38 Mb-39 Mb | chr22: 43 Mb-44 Mb | chr5: 154 Mb-155 Mb | chr9: 68 Mb-69 Mb |
| chr11: 108 Mb-109 Mb | chr17: 39 Mb-40 Mb | chr22: 44 Mb-45 Mb | chr5: 155 Mb-156 Mb | chr9: 69 Mb-70 Mb |
| chr11: 109 Mb-110 Mb | chr17: 40 Mb-41 Mb | chr22: 45 Mb-46 Mb | chr5: 156 Mb-157 Mb | chr9: 70 Mb-71 Mb |
| chr11: 110 Mb-111 Mb | chr17: 41 Mb-42 Mb | chr22: 46 Mb-47 Mb | chr5: 157 Mb-158 Mb | chr9: 71 Mb-72 Mb |
| chr11: 111 Mb-112 Mb | chr17: 42 Mb-43 Mb | chr22: 47 Mb-48 Mb | chr5: 158 Mb-159 Mb | chr9: 72 Mb-73 Mb |
| chr11: 112 Mb-113 Mb | chr17: 43 Mb-44 Mb | chr22: 48 Mb-49 Mb | chr5: 159 Mb-160 Mb | chr9: 73 Mb-74 Mb |
| chr11: 113 Mb-114 Mb | chr17: 44 Mb-45 Mb | chr22: 49 Mb-50 Mb | chr5: 160 Mb-161 Mb | chr9: 74 Mb-75 Mb |
| chr11: 114 Mb-115 Mb | chr17: 45 Mb-46 Mb | chr22: 50 Mb-51 Mb | chr5: 161 Mb-162 Mb | chr9: 75 Mb-76 Mb |
| chr11: 115 Mb-116 Mb | chr17: 46 Mb-47 Mb | chr22: 51 Mb-51304566 | chr5: 162 Mb-163 Mb | chr9: 76 Mb-77 Mb |
| chr11: 116 Mb-117 Mb | chr17: 47 Mb-48 Mb | chr3: 0-1 Mb | chr5: 163 Mb-164 Mb | chr9: 77 Mb-78 Mb |
| chr11: 117 Mb-118 Mb | chr17: 48 Mb-49 Mb | chr3: 1 Mb-2 Mb | chr5: 164 Mb-165 Mb | chr9: 78 Mb-79 Mb |
| chr11: 118 Mb-119 Mb | chr17: 49 Mb-50 Mb | chr3: 2 Mb-3 Mb | chr5: 165 Mb-166 Mb | chr9: 79 Mb-8 Mb0 |
| chr11: 119 Mb-120 Mb | chr17: 50 Mb-51 Mb | chr3: 3 Mb-4 Mb | chr5: 166 Mb-167 Mb | chr9: 8 Mb0-81 Mb |
| chr11: 120 Mb-121 Mb | chr17: 51 Mb-52 Mb | chr3: 4 Mb-5 Mb | chr5: 167 Mb-168 Mb | chr9: 81 Mb-82 Mb |
| chr11: 121 Mb-122 Mb | chr17: 52 Mb-53 Mb | chr3: 5 Mb-6 Mb | chr5: 168 Mb-169 Mb | chr9: 82 Mb-83 Mb |
| chr11: 122 Mb-123 Mb | chr17: 53 Mb-54 Mb | chr3: 6 Mb-7 Mb | chr5: 169 Mb-170 Mb | chr9: 83 Mb-84 Mb |
| chr11: 123 Mb-124 Mb | chr17: 54 Mb-55 Mb | chr3: 7 Mb-8 Mb | chr5: 170 Mb-171 Mb | chr9: 84 Mb-85 Mb |
| chr11: 124 Mb-125 Mb | chr17: 55 Mb-56 Mb | chr3: 8 Mb-9 Mb | chr5: 171 Mb-172 Mb | chr9: 85 Mb-86 Mb |
| chr11: 125 Mb-126 Mb | chr17: 56 Mb-57 Mb | chr3: 9 Mb-10 Mb | chr5: 172 Mb-173 Mb | chr9: 86 Mb-87 Mb |
| chr11: 126 Mb-127 Mb | chr17: 57 Mb-58 Mb | chr3: 10 Mb-11 Mb | chr5: 173 Mb-174 Mb | chr9: 87 Mb-88 Mb |
| chr11: 127 Mb-128 Mb | chr17: 58 Mb-59 Mb | chr3: 11 Mb-12 Mb | chr5: 174 Mb-175 Mb | chr9: 88 Mb-89 Mb |
| chr11: 128 Mb-129 Mb | chr17: 59 Mb-60 Mb | chr3: 12 Mb-13 Mb | chr5: 175 Mb-176 Mb | chr9: 89 Mb-90 Mb |
| chr11: 129 Mb-130 Mb | chr17: 60 Mb-61 Mb | chr3: 13 Mb-14 Mb | chr5: 176 Mb-177 Mb | chr9: 90 Mb-91 Mb |
| chr11: 130 Mb-131 Mb | chr17: 61 Mb-62 Mb | chr3: 14 Mb-15 Mb | chr5: 177 Mb-178 Mb | chr9: 91 Mb-92 Mb |
| chr11: 131 Mb-132 Mb | chr17: 62 Mb-63 Mb | chr3: 15 Mb-16 Mb | chr5: 178 Mb-179 Mb | chr9: 92 Mb-93 Mb |
| chr11: 132 Mb-133 Mb | chr17: 63 Mb-64 Mb | chr3: 16 Mb-17 Mb | chr5: 179 Mb-18 Mb0 | chr9: 93 Mb-94 Mb |
| chr11: 133 Mb-134 Mb | chr17: 64 Mb-65 Mb | chr3: 17 Mb-18 Mb | chr5: 18 Mb0-180915260 | chr9: 94 Mb-95 Mb |
| chr11: 134 Mb-135 Mb | chr17: 65 Mb-66 Mb | chr3: 18 Mb-19 Mb | chr6: 0-1 Mb | chr9: 95 Mb-96 Mb |
| chr12: 0-1 Mb | chr17: 66 Mb-67 Mb | chr3: 19 Mb-20 Mb | chr6: 1 Mb-2 Mb | chr9: 96 Mb-97 Mb |
| chr12: 1 Mb-2 Mb | chr17: 67 Mb-68 Mb | chr3: 20 Mb-21 Mb | chr6: 2 Mb-3 Mb | chr9: 97 Mb-98 Mb |
| chr12: 2 Mb-3 Mb | chr17: 68 Mb-69 Mb | chr3: 21 Mb-22 Mb | chr6: 3 Mb-4 Mb | chr9: 98 Mb-99 Mb |
| chr12: 3 Mb-4 Mb | chr17: 69 Mb-70 Mb | chr3: 22 Mb-23 Mb | chr6: 4 Mb-5 Mb | chr9: 99 Mb-100 Mb |
| chr12: 4 Mb-5 Mb | chr17: 70 Mb-71 Mb | chr3: 23 Mb-24 Mb | chr6: 5 Mb-6 Mb | chr9: 100 Mb-101 Mb |
| chr12: 5 Mb-6 Mb | chr17: 71 Mb-72 Mb | chr3: 24 Mb-25 Mb | chr6: 6 Mb-7 Mb | chr9: 101 Mb-102 Mb |
| chr12: 6 Mb-7 Mb | chr17: 72 Mb-73 Mb | chr3: 25 Mb-26 Mb | chr6: 7 Mb-8 Mb | chr9: 102 Mb-103 Mb |
| chr12: 7 Mb-8 Mb | chr17: 73 Mb-74 Mb | chr3: 26 Mb-27 Mb | chr6: 8 Mb-9 Mb | chr9: 103 Mb-104 Mb |
| chr12: 8 Mb-9 Mb | chr17: 74 Mb-75 Mb | chr3: 27 Mb-28 Mb | chr6: 9 Mb-10 Mb | chr9: 104 Mb-105 Mb |
| chr12: 9 Mb-10 Mb | chr17: 75 Mb-76 Mb | chr3: 28 Mb-29 Mb | chr6: 10 Mb-11 Mb | chr9: 105 Mb-106 Mb |
| chr12: 10 Mb-11 Mb | chr17: 76 Mb-77 Mb | chr3: 29 Mb-30 Mb | chr6: 11 Mb-12 Mb | chr9: 106 Mb-107 Mb |
| chr12: 11 Mb-12 Mb | chr17: 77 Mb-78 Mb | chr3: 30 Mb-31 Mb | chr6: 12 Mb-13 Mb | chr9: 107 Mb-108 Mb |
| chr12: 12 Mb-13 Mb | chr17: 78 Mb-79 Mb | chr3: 31 Mb-32 Mb | chr6: 13 Mb-14 Mb | chr9: 108 Mb-109 Mb |
| chr12: 13 Mb-14 Mb | chr17: 79 Mb-8 Mb0 | chr3: 32 Mb-33 Mb | chr6: 14 Mb-15 Mb | chr9: 109 Mb-110 Mb |
| chr12: 14 Mb-15 Mb | chr17: 8 Mb0-81 Mb | chr3: 33 Mb-34 Mb | chr6: 15 Mb-16 Mb | chr9: 110 Mb-111 Mb |
| chr12: 15 Mb-16 Mb | chr17: 81 Mb-81195210 | chr3: 34 Mb-35 Mb | chr6: 16 Mb-17 Mb | chr9: 111 Mb-112 Mb |
| chr12: 16 Mb-17 Mb | chr18: 0-1 Mb | chr3: 35 Mb-36 Mb | chr6: 17 Mb-18 Mb | chr9: 112 Mb-113 Mb |
| chr12: 17 Mb-18 Mb | chr18: 1 Mb-2 Mb | chr3: 36 Mb-37 Mb | chr6: 18 Mb-19 Mb | chr9: 113 Mb-114 Mb |
| chr12: 18 Mb-19 Mb | chr18: 2 Mb-3 Mb | chr3: 37 Mb-38 Mb | chr6: 19 Mb-20 Mb | chr9: 114 Mb-115 Mb |
| chr12: 19 Mb-20 Mb | chr18: 3 Mb-4 Mb | chr3: 38 Mb-39 Mb | chr6: 20 Mb-21 Mb | chr9: 115 Mb-116 Mb |
| chr12: 20 Mb-21 Mb | chr18: 4 Mb-5 Mb | chr3: 39 Mb-40 Mb | chr6: 21 Mb-22 Mb | chr9: 116 Mb-117 Mb |

TABLE 1-continued

| | | | | |
|---|---|---|---|---|
| chr12: 21 Mb-22 Mb | chr18: 5 Mb-6 Mb | chr3: 40 Mb-41 Mb | chr6: 22 Mb-23 Mb | chr9: 117 Mb-118 Mb |
| chr12: 22 Mb-23 Mb | chr18: 6 Mb-7 Mb | chr3: 41 Mb-42 Mb | chr6: 23 Mb-24 Mb | chr9: 118 Mb-119 Mb |
| chr12: 23 Mb-24 Mb | chr18: 7 Mb-8 Mb | chr3: 42 Mb-43 Mb | chr6: 24 Mb-25 Mb | chr9: 119 Mb-120 Mb |
| chr12: 24 Mb-25 Mb | chr18: 8 Mb-9 Mb | chr3: 43 Mb-44 Mb | chr6: 25 Mb-26 Mb | chr9: 120 Mb-121 Mb |
| chr12: 25 Mb-26 Mb | chr18: 9 Mb-10 Mb | chr3: 44 Mb-45 Mb | chr6: 26 Mb-27 Mb | chr9: 121 Mb-122 Mb |
| chr12: 26 Mb-27 Mb | chr18: 10 Mb-11 Mb | chr3: 45 Mb-46 Mb | chr6: 27 Mb-28 Mb | chr9: 122 Mb-123 Mb |
| chr12: 27 Mb-28 Mb | chr18: 11 Mb-12 Mb | chr3: 46 Mb-47 Mb | chr6: 28 Mb-29 Mb | chr9: 123 Mb-124 Mb |
| chr12: 28 Mb-29 Mb | chr18: 12 Mb-13 Mb | chr3: 47 Mb-48 Mb | chr6: 29 Mb-30 Mb | chr9: 124 Mb-125 Mb |
| chr12: 29 Mb-30 Mb | chr18: 13 Mb-14 Mb | chr3: 48 Mb-49 Mb | chr6: 31 Mb-32 Mb | chr9: 125 Mb-126 Mb |
| chr12: 30 Mb-31 Mb | chr18: 14 Mb-15 Mb | chr3: 49 Mb-50 Mb | chr6: 32 Mb-33 Mb | chr9: 126 Mb-127 Mb |
| chr12: 31 Mb-32 Mb | chr18: 15 Mb-16 Mb | chr3: 50 Mb-51 Mb | chr6: 33 Mb-34 Mb | chr9: 127 Mb-128 Mb |
| chr12: 32 Mb-33 Mb | chr18: 18 Mb-19 Mb | chr3: 51 Mb-52 Mb | chr6: 34 Mb-35 Mb | chr9: 128 Mb-129 Mb |
| chr12: 33 Mb-34 Mb | chr18: 19 Mb-20 Mb | chr3: 52 Mb-53 Mb | chr6: 35 Mb-36 Mb | chr9: 129 Mb-130 Mb |
| chr12: 34 Mb-35 Mb | chr18: 20 Mb-21 Mb | chr3: 53 Mb-54 Mb | chr6: 36 Mb-37 Mb | chr9: 130 Mb-131 Mb |
| chr12: 37 Mb-38 Mb | chr18: 21 Mb-22 Mb | chr3: 54 Mb-55 Mb | chr6: 37 Mb-38 Mb | chr9: 131 Mb-132 Mb |
| chr12: 38 Mb-39 Mb | chr18: 22 Mb-23 Mb | chr3: 55 Mb-56 Mb | chr6: 38 Mb-39 Mb | chr9: 132 Mb-133 Mb |
| chr12: 39 Mb-40 Mb | chr18: 23 Mb-24 Mb | chr3: 56 Mb-57 Mb | chr6: 39 Mb-40 Mb | chr9: 133 Mb-134 Mb |
| chr12: 40 Mb-41 Mb | chr18: 24 Mb-25 Mb | chr3: 57 Mb-58 Mb | chr6: 40 Mb-41 Mb | chr9: 134 Mb-135 Mb |
| chr12: 41 Mb-42 Mb | chr18: 25 Mb-26 Mb | chr3: 58 Mb-59 Mb | chr6: 41 Mb-42 Mb | chr9: 135 Mb-136 Mb |
| chr12: 42 Mb-43 Mb | chr18: 26 Mb-27 Mb | chr3: 59 Mb-60 Mb | chr6: 42 Mb-43 Mb | chr9: 136 Mb-137 Mb |
| chr12: 43 Mb-44 Mb | chr18: 27 Mb-28 Mb | chr3: 60 Mb-61 Mb | chr6: 43 Mb-44 Mb | chr9: 137 Mb-138 Mb |
| chr12: 44 Mb-45 Mb | chr18: 28 Mb-29 Mb | chr3: 61 Mb-62 Mb | chr6: 44 Mb-45 Mb | chr9: 138 Mb-139 Mb |
| chr12: 45 Mb-46 Mb | chr18: 29 Mb-30 Mb | chr3: 62 Mb-63 Mb | chr6: 45 Mb-46 Mb | chr9: 139 Mb-140 Mb |
| chr12: 46 Mb-47 Mb | chr18: 30 Mb-31 Mb | chr3: 63 Mb-64 Mb | chr6: 46 Mb-47 Mb | chr9: 140 Mb-141 Mb |
| chr12: 47 Mb-48 Mb | chr18: 31 Mb-32 Mb | chr3: 64 Mb-65 Mb | chr6: 47 Mb-48 Mb | chr9: 141 Mb-141213431 |
| chr12: 48 Mb-49 Mb | chr18: 32 Mb-33 Mb | chr3: 65 Mb-66 Mb | | |
| chr12: 49 Mb-50 Mb | chr18: 33 Mb-34 Mb | chr3: 66 Mb-67 Mb | | |
| chr12: 50 Mb-51 Mb | chr18: 34 Mb-35 Mb | chr3: 67 Mb-68 Mb | | |
| chr12: 51 Mb-52 Mb | chr18: 35 Mb-36 Mb | chr3: 68 Mb-69 Mb | | |

2-3. Calculation of Frequency of Mutation Signature of Single Nucleotide Variants The frequency of mutation signature of single nucleotide variants in the whole genome was calculated. The criteria for classifying mutation signatures were defined as four.

First, when mutation signatures were divided depending on the types of reference bases and changed bases, a total of six basic mutation signatures were defined (C>A, C>G, C>T, T>A, T>C, and T>G). Second, further considering a base in a 5' direction in the basic mutation signatures, 24 (4×6) mutation signatures were defined. Third, further considering a base in a 3' direction in the basic mutation signatures, 24 (6×4) mutation signatures were defined. Fourth, further considering a base in each of 5' and 3' directions in the basic mutation signatures, 96 (4×6×4) mutation signatures mainly used in mutation signature analysis were determined.

The frequency of a total of 150 mutation signatures thus divided was calculated. Thereafter, the sum of the number of mutations through each of the four mutation classification methods was calculated and divided by the total number of all mutations occurring in all bases and thus normalized.

The mutation signatures thus defined are shown in Table 2 below.

TABLE 2

| | | | | | | | | | |
|---|---|---|---|---|---|---|---|---|---|
| sig-one | C>A | sig-rev | 3CA:C>A | sig-tri | TCG:C>A | sig-tri | TCA:C>T | sig-tri | ATG:T>C |
| sig-one | C>G | sig-rev | 3CT:C>A | sig-tri | TCC:C>A | sig-tri | TCT:C>T | sig-tri | ATC:T>C |
| sig-one | C>T | sig-rev | 3CG:C>A | sig-tri | GCA:C>A | sig-tri | TCG:C>T | sig-tri | TTA:T>C |
| sig-one | T>A | sig-rev | 3CC:C>A | sig-tri | GCT:C>A | sig-tri | TCC:C>T | sig-tri | TTT:T>C |
| sig-one | T>C | sig-rev | 3CA:C>G | sig-tri | GCG:C>A | sig-tri | GCA:C>T | sig-tri | TTG:T>C |
| sig-one | T>G | sig-rev | 3CT:C>G | sig-tri | GCC:C>A | sig-tri | GCT:C>T | sig-tri | TTC:T>C |
| sig-for | 5AC:C>A | sig-rev | 3CG:C>G | sig-tri | CCA:C>A | sig-tri | GCG:C>T | sig-tri | GTA:T>C |
| sig-for | 5TC:C>A | sig-rev | 3CC:C>G | sig-tri | CCT:C>A | sig-tri | GCC:C>T | sig-tri | GTT:T>C |
| sig-for | 5GC:C>A | sig-rev | 3CA:C>T | sig-tri | CCG:C>A | sig-tri | CCA:C>T | sig-tri | GTG:T>C |
| sig-for | 5CC:C>A | sig-rev | 3CT:C>T | sig-tri | CCC:C>A | sig-tri | CCT:C>T | sig-tri | GTC:T>C |
| sig-for | 5AC:C>G | sig-rev | 3CG:C>T | sig-tri | ACA:C>G | sig-tri | CCG:C>T | sig-tri | CTA:T>C |
| sig-for | 5TC:C>G | sig-rev | 3CC:C>T | sig-tri | ACT:C>G | sig-tri | CCC:C>T | sig-tri | CTT:T>C |
| sig-for | 5GC:C>G | sig-rev | 3TA:T>A | sig-tri | ACG:C>G | sig-tri | ATA:T>A | sig-tri | CTG:T>C |
| sig-for | 5CC:C>G | sig-rev | 3TT:T>A | sig-tri | ACC:C>G | sig-tri | ATT:T>A | sig-tri | CTC:T>C |

TABLE 2-continued

| | | | | | | | | | |
|---|---|---|---|---|---|---|---|---|---|
| sig-for | 5AC:C>T | sig-rev | 3TG:T>A | sig-tri | TCA:C>G | sig-tri | ATG:T>A | sig-tri | ATA:T>G |
| sig-for | 5TC:C>T | sig-rev | 3TC:T>A | sig-tri | TCT:C>G | sig-tri | ATC:T>A | sig-tri | ATT:T>G |
| sig-for | 5GC:C>T | sig-rev | 3TA:T>C | sig-tri | TCG:C>G | sig-tri | TTA:T>A | sig-tri | ATG:T>G |
| sig-for | 5CC:C>T | sig-rev | 3TT:T>C | sig-tri | TCC:C>G | sig-tri | TTT:T>A | sig-tri | ATC:T>G |
| sig-for | 5AT:T>A | sig-rev | 3TG:T>C | sig-tri | GCA:C>G | sig-tri | TTG:T>A | sig-tri | TTA:T>G |
| sig-for | 5TT:T>A | sig-rev | 3TC:T>C | sig-tri | GCT:C>G | sig-tri | TTC:T>A | sig-tri | TTT:T>G |
| sig-for | 5GT:T>A | sig-rev | 3TA:T>G | sig-tri | GCG:C>G | sig-tri | GTA:T>A | sig-tri | TTG:T>G |
| sig-for | 5CT:T>A | sig-rev | 3TT:T>G | sig-tri | GCC:C>G | sig-tri | GTT:T>A | sig-tri | TTC:T>G |
| sig-for | 5AT:T>C | sig-rev | 3TG:T>G | sig-tri | CCA:C>G | sig-tri | GTG:T>A | sig-tri | GTA:T>G |
| sig-for | 5TT:T>C | sig-rev | 3TC:T>G | sig-tri | CCT:C>G | sig-tri | GTC:T>A | sig-tri | GTT:T>G |
| sig-for | 5GT:T>C | sig-tri | ACA:C>A | sig-tri | CCG:C>G | sig-tri | CTA:T>A | sig-tri | GTG:T>G |
| sig-for | 5CT:T>C | sig-tri | ACT:C>A | sig-tri | CCC:C>G | sig-tri | CTT:T>A | sig-tri | GTC:T>G |
| sig-for | 5AT:T>G | sig-tri | ACG:C>A | sig-tri | ACA:C>T | sig-tri | CTG:T>A | sig-tri | CTA:T>G |
| sig-for | 5TT:T>G | sig-tri | ACC:C>A | sig-tri | ACT:C>T | sig-tri | CTC:T>A | sig-tri | CTT:T>G |
| sig-for | 5GT:T>G | sig-tri | TCA:C>A | sig-tri | ACG:C>T | sig-tri | ATA:T>C | sig-tri | CTG:T>G |
| sig-for | 5CT:T>G | sig-tri | TCT:C>A | sig-tri | ACC:C>T | sig-tri | ATT:T>C | sig-tri | CTC:T>G |

Finally, 2876 features, resulting from combining 2726 regional mutation density features with 150 mutation signature features, were used as input values for the algorithm.

Example 3. Construction and Training of DNN Model

In order to develop an algorithm for diagnosing cancer and classifying types of cancer in cfDNA, a total of 2876 features for regional mutation density and mutation signature obtained through the above analysis were used. A total of two artificial intelligence algorithms were developed.

First, a binary classification model for diagnosing whether a subject is a normal person or a cancer patient was constructed. Second, a multiple classification model to classify types of cancer was constructed. As a loss function for algorithm training, binary cross-entropy was used for the binary classification model and categorical cross-entropy was used for the multiple classification model. A Deep Neural Network artificial intelligence model was used for algorithm training.

The entire dataset was divided into training, validation, and test datasets, and the model was trained through hyperparameter tuning using a method called Bayesian optimization. The entire dataset was divided into 5 training, validation, and test sets, and training was carried out five times to create five algorithm models. Then, prediction was performed on each of 5 test datasets using five algorithm models, allowing each dataset to serve once as the test dataset. Thereby, model performance was evaluated using a prediction probability when the entire sample was the test dataset.

Example 4. Construction of Deep Learning Model for Cancer Diagnosis and Cancer-Type Classification and Confirmation of Performance Thereof In order to test the performance of the deep learning model constructed using the reads obtained in Example 1, methods of conventionally known artificial intelligence models (Cristiano S. et al., Nature, Vol. 570 (7761), pp. 385-389. 2019) used for cancer diagnosis and cancer-type determination were applied and the dataset of Example 1 suitable for cfDNA was used, and as such, a cancer diagnosis and cancer-type determination comparison model based on fragmentation pattern and copy number variation (CNV) was constructed.

More specifically, in the fragment pattern method, the whole genome was binned into 5 Mb after GC correction, and the ratio of the number of short fragments to the total number of fragments in bins was used as an input value through z-score normalization. Here, the short fragment indicates a fragment having a length of 100 bp to 150 bp. The CNV method includes dividing the whole genome into non-overlapping 50 kb regions, calculating the depth of each region after GC correction, and converting the same into a log 2 value, which is then used as an input value. Also, xgboost was used to train the fragment pattern and CNV model.

In order to compare the performance of cancer diagnosis models, sensitivity was measured at prediction probability thresholds when specificities were 95%, 98%, and 99%.

Figure 2A:
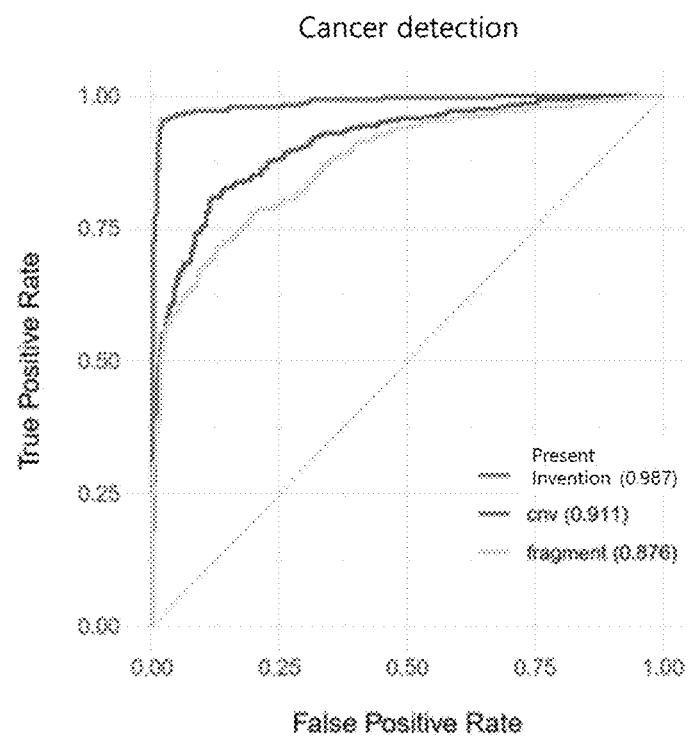
FIGS. 2A and 2B show results confirming cancer diagnosis performance of a DNN model constructed in an embodiment of the present invention by comparing the same with other models, FIG. 2A showing accuracy of cancer diagnosis performance, and FIG. 2B showing cancer-type determination performance.
Figure 2B:
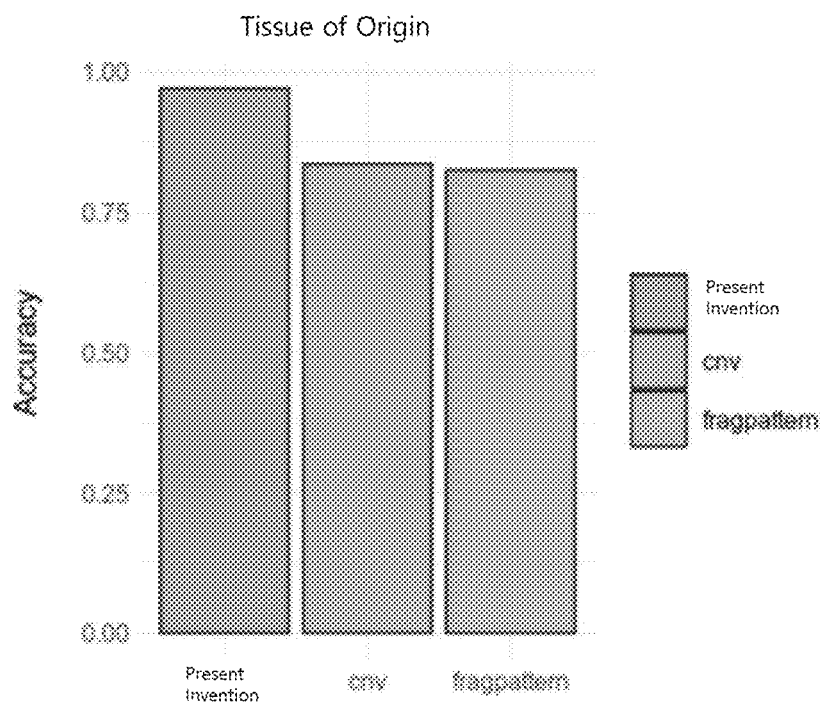
Figure 3:
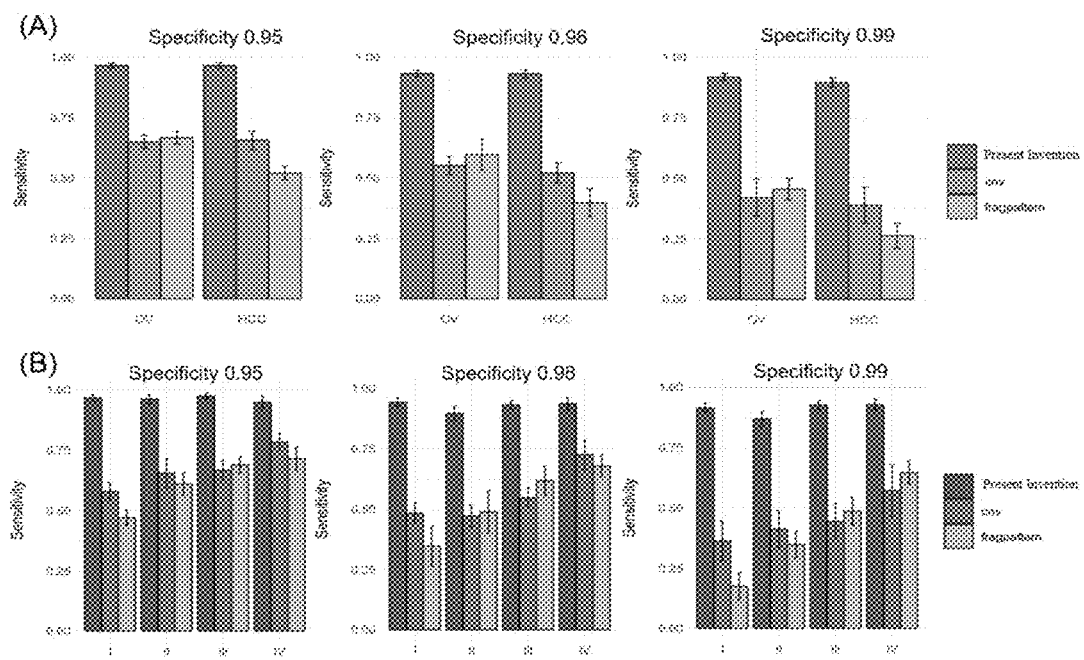
FIG. 3A shows results of comparing the cancer diagnosis performance of the DNN model constructed in an embodiment of the present invention with conventional techniques depending on the type of cancer.
FIG. 3B shows results of performance comparison at different stages of cancer progression.
Figure 4:
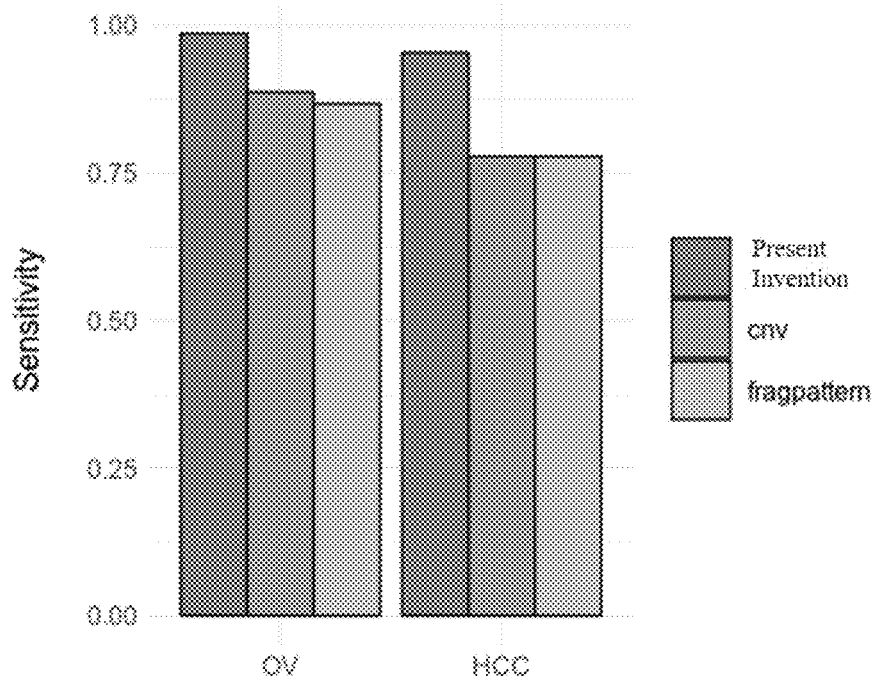
FIG. 4A shows results of comparing the cancer-type determination performance of the DNN model constructed in an embodiment of the present invention with conventional techniques depending on the type of cancer.
FIG. 4B shows results of performance comparison at different stages of cancer progression.
Figure 4:
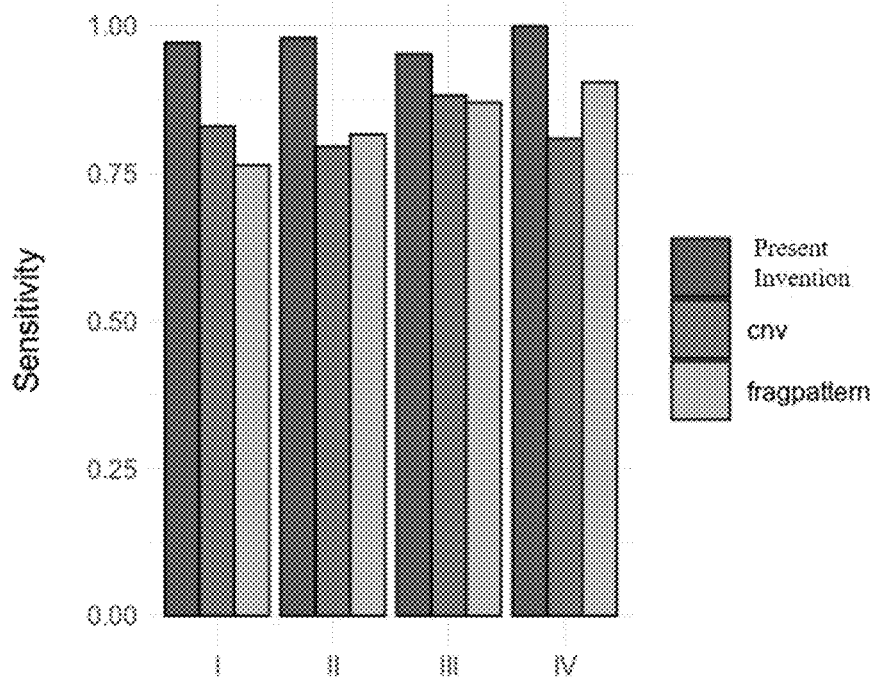

Consequently, as shown in FIGS. 2A and 2B, it was confirmed that the performance of the cancer diagnosis model constructed in the present invention was superior compared to the conventional methods. As shown in FIGS. 3A and 3B, with regard to accuracy, the cancer diagnosis model constructed in the present invention exhibited excellent performance in cancer diagnosis, and as shown in FIG. 3B, it was confirmed that the conventional methods have poor performance in early cancer diagnosis (stage I) but that the cancer diagnosis model constructed in the present invention has excellent performance even in early cancer diagnosis.

Also, based on the results of comparison of performance of the cancer-type determination model, as shown in FIGS.

4A and 4B, it was confirmed that the cancer-type determination model constructed in the present invention was superior in cancer-type determination performance at all stages compared to the conventional methods.

Example 5. Confirmation of Effect of Filtering Conditions

5-1. Confirmation of Effect of Filtering Criteria

The present inventors detected all mutations that could be cancer-derived mutations based on the lenient criteria, and then removed artifacts and germline mutations using various criteria. The present inventors performed a performance comparison when mutations were detected through a strict method, a less strict method, and a lenient method. In the strict method, mutations were detected when variant reads were present in both forward and reverse reads, and in the less strict method, mutations were detected even when there were two or more mutations in the variant reads. The lenient method was the same as the method described in Example 2-1. After mutation detection, model training using the same filtering and training processes and then performance comparison were performed.

Figure 5:
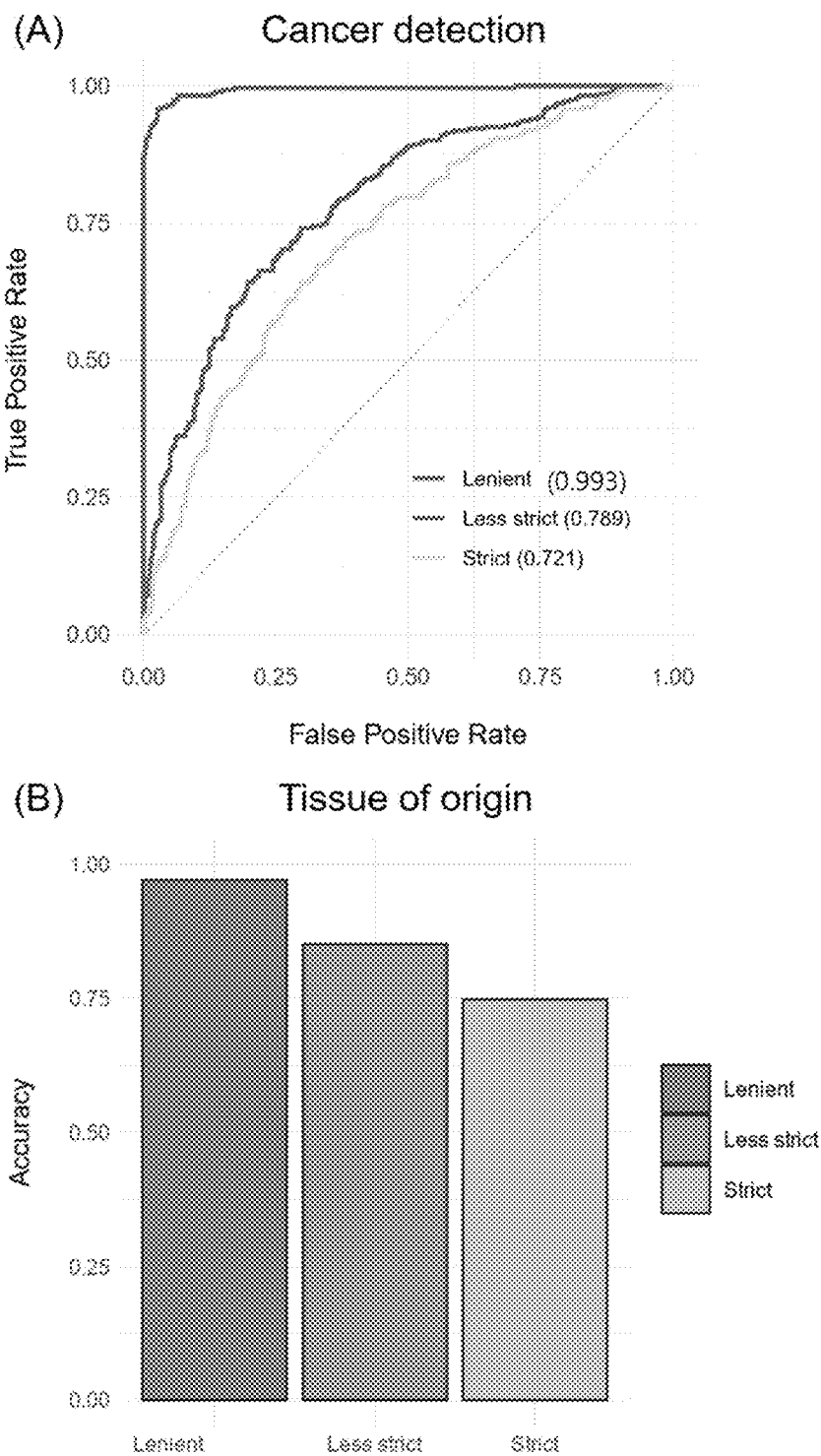
FIG. 5A shows results confirming the performance of the constructed cancer diagnosis model based on different mutation detection criteria according to an embodiment of the present invention.
FIG. 5B shows results confirming the cancer-type determination performance.

Consequently, it was confirmed that the best performance was obtained upon filtering after detection of all mutations that could be cancer-derived mutations on the lenient basis as shown in FIGS. 5A and 5B.

5-2. Confirmation of Effect of Filtering Database

In the present invention, a method of filtering mutations in cfDNA and tissues of normal persons was used along with lenient mutation detection. By applying mutations detected in large-scale normal cfDNA/tissue WGS to mutation filtering, it was expected that detection of artifacts and germline mutations that could occur in cfDNA could be effectively removed.

Since the public database included no large-scale normal cfDNA mutation database, cfDNA WGS of 20,000 normal persons produced by Green Cross was used.

Figure 6:
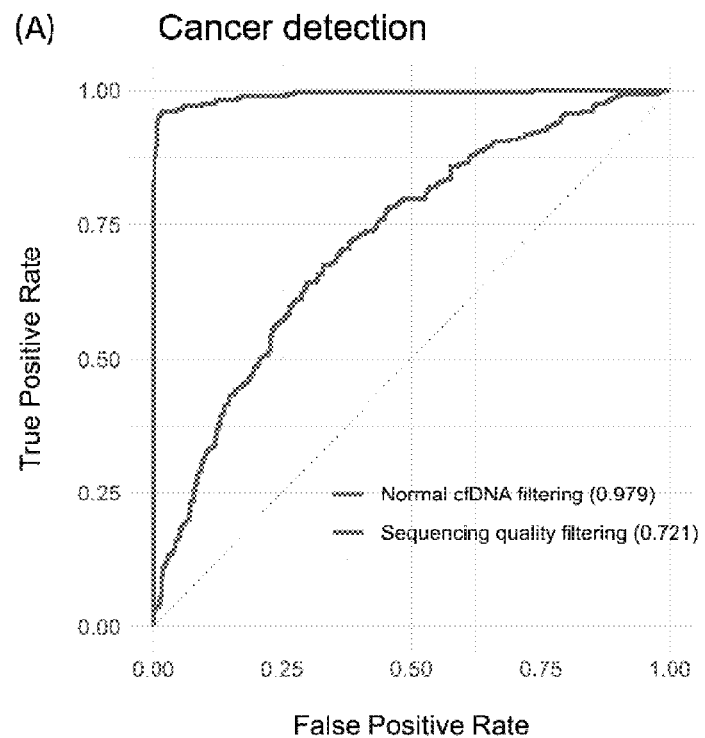
FIG. 6A shows results confirming the cancer diagnosis model performance in a filtering process using a normal cfDNA WGS database and a filtering process using technical characteristics of cfDNA according to an embodiment of the present invention.
FIG. 6B shows results confirming the cancer-type determination performance.
Figure 6:
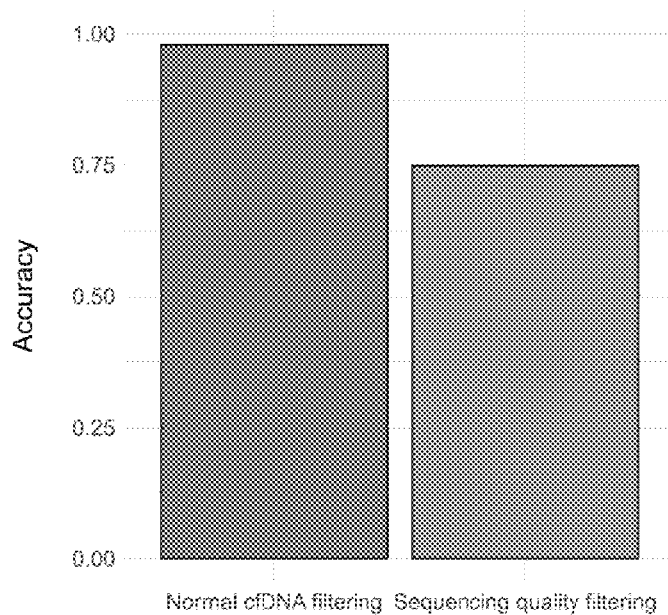

Consequently, as shown in FIGS. 6A and 6B, it was confirmed that, when normal cfDNA and tissue mutations were used, performance was improved. Therefore, in the prediction model of the present invention, both public databases for normal cfDNA mutations and normal tissue mutations were used.

Example 6. RMD Distribution of cfDNA Mutation in Cancer-Specific Mutation Region When cfDNA mutations were detected through the cfDNA mutation detection method developed in the present invention and the RMD value thereof was calculated, it was attempted to confirm that actual characteristics and distribution of the corresponding cancer were well reflected.

In PCAWG, which is a large-scale oncogenome cohort, tumor mutations were detected for each sample using tumor tissue WGS of ovarian cancer and liver cancer, and the RMD values thereof were calculated per 1 Mbp bin, after which a cancer-specific mutation-enriched region and a cancer-specific mutation-depleted region were found for each cancer type using edgeR. Indeed, it was confirmed whether the cancer-specific mutation-enriched region had a high RMD value in cfDNA and whether the cfDNA RMD value was low in the cancer-specific mutation-depleted region.

Figure 7:
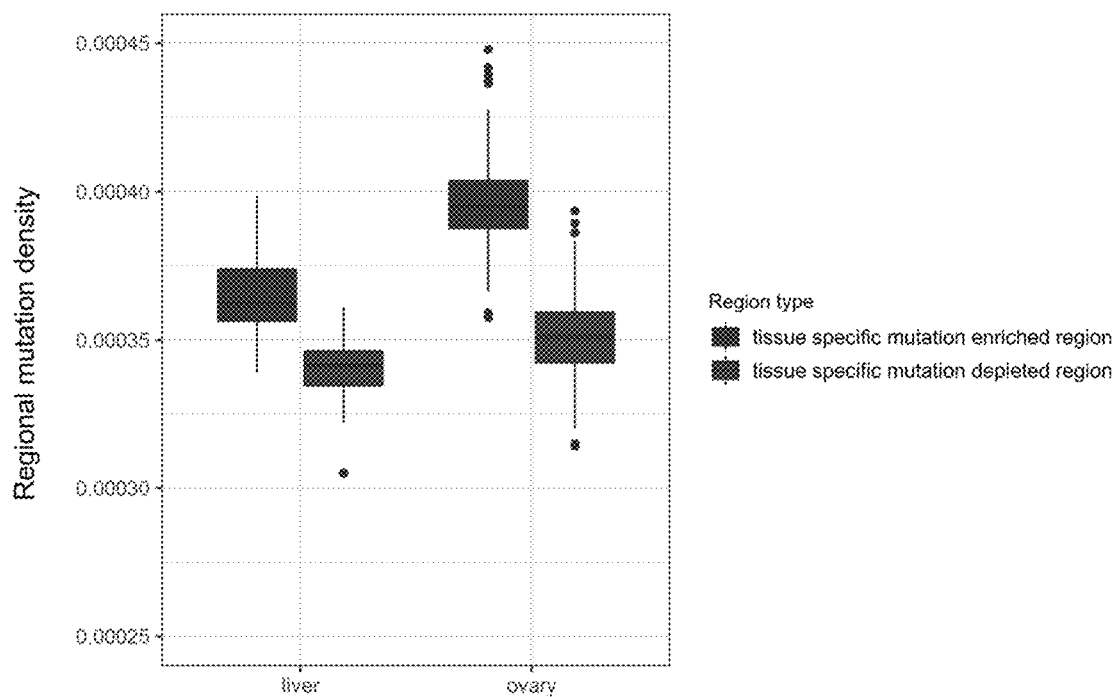
FIG. 7 shows results confirming whether the cancer-specific RMD value of cfDNA calculated in the manner constructed according to an embodiment of the present invention well reflects the cancer-specific RMD value in a tissue sample.

Consequently, as shown in FIG. 7, it was confirmed that both ovarian cancer and liver cancer reflected the RMD characteristics of the corresponding cancer in cfDNA as in the tissue sample. In the drawing, the liver and ovary on the X axis represent the types of cancer of actual cfDNA samples. Also, region type means a cancer-specific mutation-enriched/depleted region as defined using PCAWG data.

Although specific embodiments of the present invention have been disclosed in detail above, it will be obvious to those skilled in the art that the description is merely of preferable exemplary embodiments, and is not to be construed as limiting the scope of the present invention. Therefore, the substantial scope of the present invention will be defined by the appended claims and equivalents thereto.

INDUSTRIAL APPLICABILITY

As is apparent from the above description, a method of diagnosing cancer and predicting the type of cancer based on a single nucleotide variant in a cell-free nucleic acid according to the present invention is capable of exhibiting high sensitivity and accuracy compared to other methods of diagnosing cancer and predicting the type of cancer using genetic information of cell-free nucleic acids, and of ensuring the same level of sensitivity and accuracy as cancer-tissue-cell-based methods, and can be usefully applied to other analyses using single nucleotide variants in cell-free nucleic acids.

What is claimed is:

1. A method for measuring regional mutation density (RMD) and a frequency of mutation signature, the method comprising:
   (a) extracting nucleic acids from a biological sample to obtain sequence read information, the sequence read information comprising reads of 5 to 5,000 bp, and comprising at least 5,000 reads, the extracted nucleic acids comprising cell free DNA (cfDNA);
   (b) aligning the obtained sequence read information to a reference genome from a reference genome database to generate aligned sequence read information;
   (c) extracting cancer-specific single nucleotide variants, wherein the extracting is performed by detecting single nucleotide variants in the aligned sequence read information and performing filtering based on the aligned sequence read information, the filtering comprising removing artifacts and germline mutations generated during the sequencing process;
   (d) dividing the reference genome into predetermined chromosomal bins and calculating a RMD of extracted cancer-specific single nucleotide variants from step (c) in each bin;
   (e) calculating a frequency of 150 mutation signatures of the extracted cancer-specific single nucleotide variants from step (c), the 150 mutation signature features comprising:
      (i) 6 basic mutation signatures (C>A, C>G, C>T, T>A, T>C, and T>G);
      (ii.) 24 (4×6) mutation signatures for a base mutation in a 5' direction;
      (iii.) 24 (6×4) mutation signatures for a base mutation in a 3' direction;
      (iv.) 96 (4×6×4) mutation signatures for a base mutation in a 5' direction and a base mutation in a 3' direction;

(f) combining the RMD of extracted cancer-specific single nucleotide variants calculated in step (d) and the frequency of mutation signature of extracted cancer-specific single nucleotide variants calculated in step (e);
(g) inputting the combined RMD and frequency of mutation signature of step (f) into an artificial intelligence model trained to perform cancer diagnosis;
(h) determining an output value using the artificial intelligence model, wherein the artificial intelligence model transforms the combined RMD and frequency of mutation signature of step (f) into an output value, that is a probability value between 0 and 1; and
(i) determining whether cancer is present or not by comparing the output value with a reference value, that is a value between 0 and 1 capable of determining the presence of cancer when compared to the output value;
determining the presence of cancer when the output value exceeds the reference value,
training the artificial intelligence model for cancer diagnosis using a binary cross-entropy loss function represented by Equation 1:

$$BCE = -\frac{1}{N}\sum_{i=0}^{N} y_i \cdot \log(\hat{y}_i) + (1 - y_i) \cdot \log(1 - \hat{y}_i),\quad \text{Equation 1}$$

where N is a total number of samples, $\hat{y}_i$ is a probability value predicted by the model that an $i^{th}$ input value is close to class 1, and $y_i$ is an actual class of the $i^{th}$ input value;
wherein the training comprises:
hyper-parameter tuning using Bayesian optimization;
inputting regional mutation density and mutation signature data divided into training, validation, and test datasets into the artificial intelligence model;
performing cancer detection on each of the test datasets using the artificial intelligence model, allowing each dataset to serve once as the test dataset; and
evaluating model performance using a prediction probability when the entire sample was the test dataset.

2. The method according to claim 1, wherein step (a) is performed through a method comprising:

(a-i) obtaining nucleic acids from a biological sample;
(a-ii) obtaining purified nucleic acids by removing proteins, fats, and other residues from the collected nucleic acids using a salting-out method, a column chromatography method, or a bead method;
(a-iii) constructing a single-end sequencing library or a pair-end sequencing library for the purified nucleic acids or nucleic acids randomly fragmented through an enzymatic digestion, pulverization, or HydroShear method;
(a-iv) allowing the constructed library to react in a next-generation sequencer; and
(a-v) acquiring sequence read information of nucleic acids in the next-generation sequencer.

3. The method according to claim 1, wherein the filtering in step (c) comprises extracting single nucleotide variants in which a read depth of a mutation region with detected single nucleotide variants is 3 or more and an average sequencing quality is 30 or more.

4. The method according to claim 1 wherein the removing the artifacts and germline mutations comprises removing at least one mutation selected from the group consisting of:
i) a mutation detected in only one of a read pair;
ii) a mutation detected in two or more types at one position;
iii) a mutation in which a normal base is not detected at each position; and
iv) a mutation detected in a population database.

5. The method according to claim 1, wherein the bin in step (d) is 100 kb to 10 Mb.

6. The method according to claim 1, wherein the calculating the RMD of the extracted cancer-specific single nucleotide variants in step (d) is performed through a method comprising:
(d-i) calculating a number of extracted cancer-specific single nucleotide variants in bins, excluding bins in which extracted cancer-specific single nucleotide variants are not present in 40-60% or more of the entire sample; and
(d-ii) normalizing the calculated number by dividing the calculated number by a total number of mutations in bins.

7. The method according to claim 6, wherein the bin is at least one selected from among bins shown in Table 1 below

TABLE 1

| | | | | |
|---|---|---|---|---|
| chr1: 0-1 Mb | chr12: 52 Mb-53 Mb | chr18: 36 Mb-37 Mb | chr3: 69 Mb-70 Mb | chr6: 52 Mb-53 Mb |
| chr1: 1 Mb-2 Mb | chr12: 53 Mb-54 Mb | chr18: 37 Mb-38 Mb | chr3: 70 Mb-71 Mb | chr6: 53 Mb-54 Mb |
| chr1: 2 Mb-3 Mb | chr12: 54 Mb-55 Mb | chr18: 38 Mb-39 Mb | chr3: 71 Mb-72 Mb | chr6: 54 Mb-55 Mb |
| chr1: 3 Mb-4 Mb | chr12: 55 Mb-56 Mb | chr18: 39 Mb-40 Mb | chr3: 72 Mb-73 Mb | chr6: 55 Mb-56 Mb |
| chr1: 4 Mb-5 Mb | chr12: 56 Mb-57 Mb | chr18: 40 Mb-41 Mb | chr3: 73 Mb-74 Mb | chr6: 56 Mb-57 Mb |
| chr1: 5 Mb-6 Mb | chr12: 57 Mb-58 Mb | chr18: 41 Mb-42 Mb | chr3: 74 Mb-75 Mb | chr6: 57 Mb-58 Mb |
| chr1: 6 Mb-7 Mb | chr12: 58 Mb-59 Mb | chr18: 42 Mb-43 Mb | chr3: 75 Mb-76 Mb | chr6: 58 Mb-59 Mb |
| chr1: 7 Mb-8 Mb | chr12: 59 Mb-60 Mb | chr18: 43 Mb-44 Mb | chr3: 76 Mb-77 Mb | chr6: 61 Mb-62 Mb |
| chr1: 8 Mb-9 Mb | chr12: 60 Mb-61 Mb | chr18: 44 Mb-45 Mb | chr3: 77 Mb-78 Mb | chr6: 62 Mb-63 Mb |
| chr1: 9 Mb-10 Mb | chr12: 61 Mb-62 Mb | chr18: 45 Mb-46 Mb | chr3: 78 Mb-79 Mb | chr6: 63 Mb-64 Mb |
| chr1: 10 Mb-11 Mb | chr12: 62 Mb-63 Mb | chr18: 46 Mb-47 Mb | chr3: 79 Mb-8 Mb0 | chr6: 64 Mb-65 Mb |
| chr1: 11 Mb-12 Mb | chr12: 63 Mb-64 Mb | chr18: 47 Mb-48 Mb | chr3: 8 Mb0-81 Mb | chr6: 65 Mb-66 Mb |
| chr1: 12 Mb-13 Mb | chr12: 64 Mb-65 Mb | chr18: 48 Mb-49 Mb | chr3: 81 Mb-82 Mb | chr6: 66 Mb-67 Mb |
| chr1: 13 Mb-14 Mb | chr12: 65 Mb-66 Mb | chr18: 49 Mb-50 Mb | chr3: 82 Mb-83 Mb | chr6: 67 Mb-68 Mb |
| chr1: 14 Mb-15 Mb | chr12: 66 Mb-67 Mb | chr18: 50 Mb-51 Mb | chr3: 83 Mb-84 Mb | chr6: 68 Mb-69 Mb |
| chr1: 15 Mb-16 Mb | chr12: 67 Mb-68 Mb | chr18: 51 Mb-52 Mb | chr3: 84 Mb-85 Mb | chr6: 69 Mb-70 Mb |
| chr1: 16 Mb-17 Mb | chr12: 68 Mb-69 Mb | chr18: 52 Mb-53 Mb | chr3: 85 Mb-86 Mb | chr6: 70 Mb-71 Mb |
| chr1: 17 Mb-18 Mb | chr12: 69 Mb-70 Mb | chr18: 53 Mb-54 Mb | chr3: 86 Mb-87 Mb | chr6: 71 Mb-72 Mb |
| chr1: 18 Mb-19 Mb | chr12: 70 Mb-71 Mb | chr18: 54 Mb-55 Mb | chr3: 87 Mb-88 Mb | chr6: 72 Mb-73 Mb |
| chr1: 19 Mb-20 Mb | chr12: 71 Mb-72 Mb | chr18: 55 Mb-56 Mb | chr3: 88 Mb-89 Mb | chr6: 73 Mb-74 Mb |
| chr1: 20 Mb-21 Mb | chr12: 72 Mb-73 Mb | chr18: 56 Mb-57 Mb | chr3: 89 Mb-90 Mb | chr6: 74 Mb-75 Mb |
| chr1: 21 Mb-22 Mb | chr12: 73 Mb-74 Mb | chr18: 57 Mb-58 Mb | chr3: 90 Mb-91 Mb | chr6: 75 Mb-76 Mb |
| chr1: 22 Mb-23 Mb | chr12: 74 Mb-75 Mb | chr18: 58 Mb-59 Mb | chr3: 93 Mb-94 Mb | chr6: 76 Mb-77 Mb |
| chr1: 23 Mb-24 Mb | chr12: 75 Mb-76 Mb | chr18: 59 Mb-60 Mb | chr3: 94 Mb-95 Mb | chr6: 77 Mb-78 Mb |
| chr1: 24 Mb-25 Mb | chr12: 76 Mb-77 Mb | chr18: 60 Mb-61 Mb | chr3: 95 Mb-96 Mb | chr6: 78 Mb-79 Mb |

TABLE 1-continued

| | | | | |
|---|---|---|---|---|
| chr1: 25 Mb-26 Mb | chr12: 77 Mb-78 Mb | chr18: 61 Mb-62 Mb | chr3: 96 Mb-97 Mb | chr6: 79 Mb-8 Mb0 |
| chr1: 26 Mb-27 Mb | chr12: 78 Mb-79 Mb | chr18: 62 Mb-63 Mb | chr3: 97 Mb-98 Mb | chr6: 8 Mb0-81 Mb |
| chr1: 27 Mb-28 Mb | chr12: 79 Mb-8 Mb0 | chr18: 63 Mb-64 Mb | chr3: 98 Mb-99 Mb | chr6: 81 Mb-82 Mb |
| chr1: 28 Mb-29 Mb | chr12: 8 Mb0-81 Mb | chr18: 64 Mb-65 Mb | chr3: 99 Mb-100 Mb | chr6: 82 Mb-83 Mb |
| chr1: 29 Mb-30 Mb | chr12: 81 Mb-82 Mb | chr18: 65 Mb-66 Mb | chr3: 100 Mb-101 Mb | chr6: 83 Mb-84 Mb |
| chr1: 30 Mb-31 Mb | chr12: 82 Mb-83 Mb | chr18: 66 Mb-67 Mb | chr3: 101 Mb-102 Mb | chr6: 84 Mb-85 Mb |
| chr1: 31 Mb-32 Mb | chr12: 83 Mb-84 Mb | chr18: 67 Mb-68 Mb | chr3: 102 Mb-103 Mb | chr6: 85 Mb-86 Mb |
| chr1: 32 Mb-33 Mb | chr12: 84 Mb-85 Mb | chr18: 68 Mb-69 Mb | chr3: 103 Mb-104 Mb | chr6: 86 Mb-87 Mb |
| chr1: 33 Mb-34 Mb | chr12: 85 Mb-86 Mb | chr18: 69 Mb-70 Mb | chr3: 104 Mb-105 Mb | chr6: 87 Mb-88 Mb |
| chr1: 34 Mb-35 Mb | chr12: 86 Mb-87 Mb | chr18: 70 Mb-71 Mb | chr3: 105 Mb-106 Mb | chr6: 88 Mb-89 Mb |
| chr1: 35 Mb-36 Mb | chr12: 87 Mb-88 Mb | chr18: 71 Mb-72 Mb | chr3: 106 Mb-107 Mb | chr6: 89 Mb-90 Mb |
| chr1: 36 Mb-37 Mb | chr12: 88 Mb-89 Mb | chr18: 72 Mb-73 Mb | chr3: 107 Mb-108 Mb | chr6: 90 Mb-91 Mb |
| chr1: 37 Mb-38 Mb | chr12: 89 Mb-90 Mb | chr18: 73 Mb-74 Mb | chr3: 108 Mb-109 Mb | chr6: 91 Mb-92 Mb |
| chr1: 38 Mb-39 Mb | chr12: 90 Mb-91 Mb | chr18: 74 Mb-75 Mb | chr3: 109 Mb-110 Mb | chr6: 92 Mb-93 Mb |
| chr1: 39 Mb-40 Mb | chr12: 91 Mb-92 Mb | chr18: 75 Mb-76 Mb | chr3: 110 Mb-111 Mb | chr6: 93 Mb-94 Mb |
| chr1: 40 Mb-41 Mb | chr12: 92 Mb-93 Mb | chr18: 76 Mb-77 Mb | chr3: 111 Mb-112 Mb | chr6: 94 Mb-95 Mb |
| chr1: 41 Mb-42 Mb | chr12: 93 Mb-94 Mb | chr18: 77 Mb-78 Mb | chr3: 112 Mb-113 Mb | chr6: 95 Mb-96 Mb |
| chr1: 42 Mb-43 Mb | chr12: 94 Mb-95 Mb | chr18: 78 Mb-78077248 | chr3: 113 Mb-114 Mb | chr6: 96 Mb-97 Mb |
| chr1: 43 Mb-44 Mb | chr12: 95 Mb-96 Mb | chr19: 0-1 Mb | chr3: 114 Mb-115 Mb | chr6: 97 Mb-98 Mb |
| chr1: 44 Mb-45 Mb | chr12: 96 Mb-97 Mb | chr19: 1 Mb-2 Mb | chr3: 115 Mb-116 Mb | chr6: 98 Mb-99 Mb |
| chr1: 45 Mb-46 Mb | chr12: 97 Mb-98 Mb | chr19: 2 Mb-3 Mb | chr3: 116 Mb-117 Mb | chr6: 99 Mb-100 Mb |
| chr1: 46 Mb-47 Mb | chr12: 98 Mb-99 Mb | chr19: 3 Mb-4 Mb | chr3: 117 Mb-118 Mb | chr6: 100 Mb-101 Mb |
| chr1: 47 Mb-48 Mb | chr12: 99 Mb-100 Mb | chr19: 4 Mb-5 Mb | chr3: 118 Mb-119 Mb | chr6: 101 Mb-102 Mb |
| chr1: 48 Mb-49 Mb | chr12: 100 Mb-101 Mb | chr19: 5 Mb-6 Mb | chr3: 119 Mb-120 Mb | chr6: 102 Mb-103 Mb |
| chr1: 49 Mb-50 Mb | chr12: 101 Mb-102 Mb | chr19: 6 Mb-7 Mb | chr3: 120 Mb-121 Mb | chr6: 103 Mb-104 Mb |
| chr1: 50 Mb-51 Mb | chr12: 102 Mb-103 Mb | chr19: 7 Mb-8 Mb | chr3: 121 Mb-122 Mb | chr6: 104 Mb-105 Mb |
| chr1: 51 Mb-52 Mb | chr12: 103 Mb-104 Mb | chr19: 8 Mb-9 Mb | chr3: 122 Mb-123 Mb | chr6: 105 Mb-106 Mb |
| chr1: 52 Mb-53 Mb | chr12: 104 Mb-105 Mb | chr19: 9 Mb-10 Mb | chr3: 123 Mb-124 Mb | chr6: 106 Mb-107 Mb |
| chr1: 53 Mb-54 Mb | chr12: 105 Mb-106 Mb | chr19: 10 Mb-11 Mb | chr3: 124 Mb-125 Mb | chr6: 107 Mb-108 Mb |
| chr1: 54 Mb-55 Mb | chr12: 106 Mb-107 Mb | chr19: 11 Mb-12 Mb | chr3: 125 Mb-126 Mb | chr6: 108 Mb-109 Mb |
| chr1: 55 Mb-56 Mb | chr12: 107 Mb-108 Mb | chr19: 12 Mb-13 Mb | chr3: 126 Mb-127 Mb | chr6: 109 Mb-110 Mb |
| chr1: 56 Mb-57 Mb | chr12: 108 Mb-109 Mb | chr19: 13 Mb-14 Mb | chr3: 127 Mb-128 Mb | chr6: 110 Mb-111 Mb |
| chr1: 57 Mb-58 Mb | chr12: 109 Mb-110 Mb | chr19: 14 Mb-15 Mb | chr3: 128 Mb-129 Mb | chr6: 111 Mb-112 Mb |
| chr1: 58 Mb-59 Mb | chr12: 110 Mb-111 Mb | chr19: 15 Mb-16 Mb | chr3: 129 Mb-130 Mb | chr6: 112 Mb-113 Mb |
| chr1: 59 Mb-60 Mb | chr12: 111 Mb-112 Mb | chr19: 16 Mb-17 Mb | chr3: 130 Mb-131 Mb | chr6: 113 Mb-114 Mb |
| chr1: 60 Mb-61 Mb | chr12: 112 Mb-113 Mb | chr19: 17 Mb-18 Mb | chr3: 131 Mb-132 Mb | chr6: 114 Mb-115 Mb |
| chr1: 61 Mb-62 Mb | chr12: 113 Mb-114 Mb | chr19: 18 Mb-19 Mb | chr3: 132 Mb-133 Mb | chr6: 115 Mb-116 Mb |
| chr1: 62 Mb-63 Mb | chr12: 114 Mb-115 Mb | chr19: 19 Mb-20 Mb | chr3: 133 Mb-134 Mb | chr6: 116 Mb-117 Mb |
| chr1: 63 Mb-64 Mb | chr12: 115 Mb-116 Mb | chr19: 20 Mb-21 Mb | chr3: 134 Mb-135 Mb | chr6: 117 Mb-118 Mb |
| chr1: 64 Mb-65 Mb | chr12: 116 Mb-117 Mb | chr19: 21 Mb-22 Mb | chr3: 135 Mb-136 Mb | chr6: 118 Mb-119 Mb |
| chr1: 65 Mb-66 Mb | chr12: 117 Mb-118 Mb | chr19: 22 Mb-23 Mb | chr3: 136 Mb-137 Mb | chr6: 119 Mb-120 Mb |
| chr1: 66 Mb-67 Mb | chr12: 118 Mb-119 Mb | chr19: 23 Mb-24 Mb | chr3: 137 Mb-138 Mb | chr6: 120 Mb-121 Mb |
| chr1: 67 Mb-68 Mb | chr12: 119 Mb-120 Mb | chr19: 24 Mb-25 Mb | chr3: 138 Mb-139 Mb | chr6: 121 Mb-122 Mb |
| chr1: 68 Mb-69 Mb | chr12: 120 Mb-121 Mb | chr19: 28 Mb-29 Mb | chr3: 139 Mb-140 Mb | chr6: 122 Mb-123 Mb |
| chr1: 69 Mb-70 Mb | chr12: 121 Mb-122 Mb | chr19: 29 Mb-30 Mb | chr3: 140 Mb-141 Mb | chr6: 123 Mb-124 Mb |
| chr1: 70 Mb-71 Mb | chr12: 122 Mb-123 Mb | chr19: 30 Mb-31 Mb | chr3: 141 Mb-142 Mb | chr6: 124 Mb-125 Mb |
| chr1: 71 Mb-72 Mb | chr12: 123 Mb-124 Mb | chr19: 31 Mb-32 Mb | chr3: 142 Mb-143 Mb | chr6: 125 Mb-126 Mb |
| chr1: 72 Mb-73 Mb | chr12: 124 Mb-125 Mb | chr19: 32 Mb-33 Mb | chr3: 143 Mb-144 Mb | chr6: 126 Mb-127 Mb |
| chr1: 73 Mb-74 Mb | chr12: 125 Mb-126 Mb | chr19: 33 Mb-34 Mb | chr3: 144 Mb-145 Mb | chr6: 127 Mb-128 Mb |
| chr1: 74 Mb-75 Mb | chr12: 126 Mb-127 Mb | chr19: 34 Mb-35 Mb | chr3: 145 Mb-146 Mb | chr6: 128 Mb-129 Mb |
| chr1: 75 Mb-76 Mb | chr12: 127 Mb-128 Mb | chr19: 35 Mb-36 Mb | chr3: 146 Mb-147 Mb | chr6: 129 Mb-130 Mb |
| chr1: 76 Mb-77 Mb | chr12: 128 Mb-129 Mb | chr19: 36 Mb-37 Mb | chr3: 147 Mb-148 Mb | chr6: 130 Mb-131 Mb |
| chr1: 77 Mb-78 Mb | chr12: 129 Mb-130 Mb | chr19: 37 Mb-38 Mb | chr3: 148 Mb-149 Mb | chr6: 131 Mb-132 Mb |
| chr1: 78 Mb-79 Mb | chr12: 130 Mb-131 Mb | chr19: 38 Mb-39 Mb | chr3: 149 Mb-150 Mb | chr6: 132 Mb-133 Mb |
| chr1: 79 Mb-8 Mb0 | chr12: 131 Mb-132 Mb | chr19: 39 Mb-40 Mb | chr3: 150 Mb-151 Mb | chr6: 133 Mb-134 Mb |
| chr1: 8 Mb0-81 Mb | chr12: 132 Mb-133 Mb | chr19: 40 Mb-41 Mb | chr3: 151 Mb-152 Mb | chr6: 134 Mb-135 Mb |
| chr1: 81 Mb-82 Mb | chr12: 133 Mb-133851895 | chr19: 41 Mb-42 Mb | chr3: 152 Mb-153 Mb | chr6: 135 Mb-136 Mb |
| chr1: 82 Mb-83 Mb | chr13: 19 Mb-20 Mb | chr19: 42 Mb-43 Mb | chr3: 153 Mb-154 Mb | chr6: 136 Mb-137 Mb |
| chr1: 83 Mb-84 Mb | chr13: 20 Mb-21 Mb | chr19: 43 Mb-44 Mb | chr3: 154 Mb-155 Mb | chr6: 137 Mb-138 Mb |
| chr1: 84 Mb-85 Mb | chr13: 21 Mb-22 Mb | chr19: 44 Mb-45 Mb | chr3: 155 Mb-156 Mb | chr6: 138 Mb-139 Mb |
| chr1: 85 Mb-86 Mb | chr13: 22 Mb-23 Mb | chr19: 45 Mb-46 Mb | chr3: 156 Mb-157 Mb | chr6: 139 Mb-140 Mb |
| chr1: 86 Mb-87 Mb | chr13: 23 Mb-24 Mb | chr19: 46 Mb-47 Mb | chr3: 157 Mb-158 Mb | chr6: 140 Mb-141 Mb |
| chr1: 87 Mb-88 Mb | chr13: 24 Mb-25 Mb | chr19: 47 Mb-48 Mb | chr3: 158 Mb-159 Mb | chr6: 141 Mb-142 Mb |
| chr1: 88 Mb-89 Mb | chr13: 25 Mb-26 Mb | chr19: 48 Mb-49 Mb | chr3: 159 Mb-160 Mb | chr6: 142 Mb-143 Mb |
| chr1: 89 Mb-90 Mb | chr13: 26 Mb-27 Mb | chr19: 49 Mb-50 Mb | chr3: 160 Mb-161 Mb | chr6: 143 Mb-144 Mb |
| chr1: 90 Mb-91 Mb | chr13: 27 Mb-28 Mb | chr19: 50 Mb-51 Mb | chr3: 161 Mb-162 Mb | chr6: 144 Mb-145 Mb |
| chr1: 91 Mb-92 Mb | chr13: 28 Mb-29 Mb | chr19: 51 Mb-52 Mb | chr3: 162 Mb-163 Mb | chr6: 145 Mb-146 Mb |
| chr1: 92 Mb-93 Mb | chr13: 29 Mb-30 Mb | chr19: 52 Mb-53 Mb | chr3: 163 Mb-164 Mb | chr6: 146 Mb-147 Mb |
| chr1: 93 Mb-94 Mb | chr13: 30 Mb-31 Mb | chr19: 53 Mb-54 Mb | chr3: 164 Mb-165 Mb | chr6: 147 Mb-148 Mb |
| chr1: 94 Mb-95 Mb | chr13: 31 Mb-32 Mb | chr19: 54 Mb-55 Mb | chr3: 165 Mb-166 Mb | chr6: 148 Mb-149 Mb |
| chr1: 95 Mb-96 Mb | chr13: 32 Mb-33 Mb | chr19: 55 Mb-56 Mb | chr3: 166 Mb-167 Mb | chr6: 149 Mb-150 Mb |
| chr1: 96 Mb-97 Mb | chr13: 33 Mb-34 Mb | chr19: 56 Mb-57 Mb | chr3: 167 Mb-168 Mb | chr6: 150 Mb-151 Mb |
| chr1: 97 Mb-98 Mb | chr13: 34 Mb-35 Mb | chr19: 57 Mb-58 Mb | chr3: 168 Mb-169 Mb | chr6: 151 Mb-152 Mb |
| chr1: 98 Mb-99 Mb | chr13: 35 Mb-36 Mb | chr19: 58 Mb-59 Mb | chr3: 169 Mb-170 Mb | chr6: 152 Mb-153 Mb |
| chr1: 99 Mb-100 Mb | chr13: 36 Mb-37 Mb | chr19: 59 Mb-59128983 | chr3: 170 Mb-171 Mb | chr6: 153 Mb-154 Mb |
| chr1: 100 Mb-101 Mb | chr13: 37 Mb-38 Mb | chr2: 0-1 Mb | chr3: 171 Mb-172 Mb | chr6: 154 Mb-155 Mb |
| chr1: 101 Mb-102 Mb | chr13: 38 Mb-39 Mb | chr2: 1 Mb-2 Mb | chr3: 172 Mb-173 Mb | chr6: 155 Mb-156 Mb |
| chr1: 102 Mb-103 Mb | chr13: 39 Mb-40 Mb | chr2: 2 Mb-3 Mb | chr3: 173 Mb-174 Mb | chr6: 156 Mb-157 Mb |
| chr1: 103 Mb-104 Mb | chr13: 40 Mb-41 Mb | chr2: 3 Mb-4 Mb | chr3: 174 Mb-175 Mb | chr6: 157 Mb-158 Mb |
| chr1: 104 Mb-105 Mb | chr13: 41 Mb-42 Mb | chr2: 4 Mb-5 Mb | chr3: 175 Mb-176 Mb | chr6: 158 Mb-159 Mb |

TABLE 1-continued

| | | | | |
|---|---|---|---|---|
| chr1: 105 Mb-106 Mb | chr13: 42 Mb-43 Mb | chr2: 5 Mb-6 Mb | chr3: 176 Mb-177 Mb | chr6: 159 Mb-160 Mb |
| chr1: 106 Mb-107 Mb | chr13: 43 Mb-44 Mb | chr2: 6 Mb-7 Mb | chr3: 177 Mb-178 Mb | chr6: 160 Mb-161 Mb |
| chr1: 107 Mb-108 Mb | chr13: 44 Mb-45 Mb | chr2: 7 Mb-8 Mb | chr3: 178 Mb-179 Mb | chr6: 161 Mb-162 Mb |
| chr1: 108 Mb-109 Mb | chr13: 45 Mb-46 Mb | chr2: 8 Mb-9 Mb | chr3: 179 Mb-18 Mb0 | chr6: 162 Mb-163 Mb |
| chr1: 109 Mb-110 Mb | chr13: 46 Mb-47 Mb | chr2: 9 Mb-10 Mb | chr3: 18 Mb0-181 Mb | chr6: 163 Mb-164 Mb |
| chr1: 110 Mb-111 Mb | chr13: 47 Mb-48 Mb | chr2: 10 Mb-11 Mb | chr3: 181 Mb-182 Mb | chr6: 164 Mb-165 Mb |
| chr1: 111 Mb-112 Mb | chr13: 48 Mb-49 Mb | chr2: 11 Mb-12 Mb | chr3: 182 Mb-183 Mb | chr6: 165 Mb-166 Mb |
| chr1: 112 Mb-113 Mb | chr13: 49 Mb-50 Mb | chr2: 12 Mb-13 Mb | chr3: 183 Mb-184 Mb | chr6: 166 Mb-167 Mb |
| chr1: 113 Mb-114 Mb | chr13: 50 Mb-51 Mb | chr2: 13 Mb-14 Mb | chr3: 184 Mb-185 Mb | chr6: 167 Mb-168 Mb |
| chr1: 114 Mb-115 Mb | chr13: 51 Mb-52 Mb | chr2: 14 Mb-15 Mb | chr3: 185 Mb-186 Mb | chr6: 168 Mb-169 Mb |
| chr1: 115 Mb-116 Mb | chr13: 52 Mb-53 Mb | chr2: 15 Mb-16 Mb | chr3: 186 Mb-187 Mb | chr6: 169 Mb-170 Mb |
| chr1: 116 Mb-117 Mb | chr13: 53 Mb-54 Mb | chr2: 16 Mb-17 Mb | chr3: 187 Mb-188 Mb | chr6: 170 Mb-171 Mb |
| chr1: 117 Mb-118 Mb | chr13: 54 Mb-55 Mb | chr2: 17 Mb-18 Mb | chr3: 188 Mb-189 Mb | chr7: 0-1 Mb |
| chr1: 118 Mb-119 Mb | chr13: 55 Mb-56 Mb | chr2: 18 Mb-19 Mb | chr3: 189 Mb-190 Mb | chr7: 1 Mb-2 Mb |
| chr1: 119 Mb-120 Mb | chr13: 56 Mb-57 Mb | chr2: 19 Mb-20 Mb | chr3: 190 Mb-191 Mb | chr7: 2 Mb-3 Mb |
| chr1: 120 Mb-121 Mb | chr13: 57 Mb-58 Mb | chr2: 20 Mb-21 Mb | chr3: 191 Mb-192 Mb | chr7: 3 Mb-4 Mb |
| chr1: 121 Mb-122 Mb | chr13: 58 Mb-59 Mb | chr2: 21 Mb-22 Mb | chr3: 192 Mb-193 Mb | chr7: 4 Mb-5 Mb |
| chr1: 142 Mb-143 Mb | chr13: 59 Mb-60 Mb | chr2: 22 Mb-23 Mb | chr3: 193 Mb-194 Mb | chr7: 5 Mb-6 Mb |
| chr1: 143 Mb-144 Mb | chr13: 60 Mb-61 Mb | chr2: 23 Mb-24 Mb | chr3: 194 Mb-195 Mb | chr7: 6 Mb-7 Mb |
| chr1: 144 Mb-145 Mb | chr13: 61 Mb-62 Mb | chr2: 24 Mb-25 Mb | chr3: 195 Mb-196 Mb | chr7: 7 Mb-8 Mb |
| chr1: 145 Mb-146 Mb | chr13: 62 Mb-63 Mb | chr2: 25 Mb-26 Mb | chr3: 196 Mb-197 Mb | chr7: 8 Mb-9 Mb |
| chr1: 146 Mb-147 Mb | chr13: 63 Mb-64 Mb | chr2: 26 Mb-27 Mb | chr3: 197 Mb-198 Mb | chr7: 9 Mb-10 Mb |
| chr1: 147 Mb-148 Mb | chr13: 64 Mb-65 Mb | chr2: 27 Mb-28 Mb | chr4: 0-1 Mb | chr7: 10 Mb-11 Mb |
| chr1: 148 Mb-149 Mb | chr13: 65 Mb-66 Mb | chr2: 28 Mb-29 Mb | chr4: 1 Mb-2 Mb | chr7: 11 Mb-12 Mb |
| chr1: 149 Mb-150 Mb | chr13: 66 Mb-67 Mb | chr2: 29 Mb-30 Mb | chr4: 2 Mb-3 Mb | chr7: 12 Mb-13 Mb |
| chr1: 150 Mb-151 Mb | chr13: 67 Mb-68 Mb | chr2: 30 Mb-31 Mb | chr4: 3 Mb-4 Mb | chr7: 13 Mb-14 Mb |
| chr1: 151 Mb-152 Mb | chr13: 68 Mb-69 Mb | chr2: 31 Mb-32 Mb | chr4: 4 Mb-5 Mb | chr7: 14 Mb-15 Mb |
| chr1: 152 Mb-153 Mb | chr13: 69 Mb-70 Mb | chr2: 32 Mb-33 Mb | chr4: 5 Mb-6 Mb | chr7: 15 Mb-16 Mb |
| chr1: 153 Mb-154 Mb | chr13: 70 Mb-71 Mb | chr2: 33 Mb-34 Mb | chr4: 6 Mb-7 Mb | chr7: 16 Mb-17 Mb |
| chr1: 154 Mb-155 Mb | chr13: 71 Mb-72 Mb | chr2: 34 Mb-35 Mb | chr4: 7 Mb-8 Mb | chr7: 17 Mb-18 Mb |
| chr1: 155 Mb-156 Mb | chr13: 72 Mb-73 Mb | chr2: 35 Mb-36 Mb | chr4: 8 Mb-9 Mb | chr7: 18 Mb-19 Mb |
| chr1: 156 Mb-157 Mb | chr13: 73 Mb-74 Mb | chr2: 36 Mb-37 Mb | chr4: 9 Mb-10 Mb | chr7: 19 Mb-20 Mb |
| chr1: 157 Mb-158 Mb | chr13: 74 Mb-75 Mb | chr2: 37 Mb-38 Mb | chr4: 10 Mb-11 Mb | chr7: 20 Mb-21 Mb |
| chr1: 158 Mb-159 Mb | chr13: 75 Mb-76 Mb | chr2: 38 Mb-39 Mb | chr4: 11 Mb-12 Mb | chr7: 21 Mb-22 Mb |
| chr1: 159 Mb-160 Mb | chr13: 76 Mb-77 Mb | chr2: 39 Mb-40 Mb | chr4: 12 Mb-13 Mb | chr7: 22 Mb-23 Mb |
| chr1: 160 Mb-161 Mb | chr13: 77 Mb-78 Mb | chr2: 40 Mb-41 Mb | chr4: 13 Mb-14 Mb | chr7: 23 Mb-24 Mb |
| chr1: 161 Mb-162 Mb | chr13: 78 Mb-79 Mb | chr2: 41 Mb-42 Mb | chr4: 14 Mb-15 Mb | chr7: 24 Mb-25 Mb |
| chr1: 162 Mb-163 Mb | chr13: 79 Mb-8 Mb0 | chr2: 42 Mb-43 Mb | chr4: 15 Mb-16 Mb | chr7: 25 Mb-26 Mb |
| chr1: 163 Mb-164 Mb | chr13: 8 Mb0-81 Mb | chr2: 43 Mb-44 Mb | chr4: 16 Mb-17 Mb | chr7: 26 Mb-27 Mb |
| chr1: 164 Mb-165 Mb | chr13: 81 Mb-82 Mb | chr2: 44 Mb-45 Mb | chr4: 17 Mb-18 Mb | chr7: 27 Mb-28 Mb |
| chr1: 165 Mb-166 Mb | chr13: 82 Mb-83 Mb | chr2: 45 Mb-46 Mb | chr4: 18 Mb-19 Mb | chr7: 28 Mb-29 Mb |
| chr1: 166 Mb-167 Mb | chr13: 83 Mb-84 Mb | chr2: 46 Mb-47 Mb | chr4: 19 Mb-20 Mb | chr7: 29 Mb-30 Mb |
| chr1: 167 Mb-168 Mb | chr13: 84 Mb-85 Mb | chr2: 47 Mb-48 Mb | chr4: 20 Mb-21 Mb | chr7: 30 Mb-31 Mb |
| chr1: 168 Mb-169 Mb | chr13: 85 Mb-86 Mb | chr2: 48 Mb-49 Mb | chr4: 21 Mb-22 Mb | chr7: 31 Mb-32 Mb |
| chr1: 169 Mb-170 Mb | chr13: 86 Mb-87 Mb | chr2: 49 Mb-50 Mb | chr4: 22 Mb-23 Mb | chr7: 32 Mb-33 Mb |
| chr1: 170 Mb-171 Mb | chr13: 87 Mb-88 Mb | chr2: 50 Mb-51 Mb | chr4: 23 Mb-24 Mb | chr7: 33 Mb-34 Mb |
| chr1: 171 Mb-172 Mb | chr13: 88 Mb-89 Mb | chr2: 51 Mb-52 Mb | chr4: 24 Mb-25 Mb | chr7: 34 Mb-35 Mb |
| chr1: 172 Mb-173 Mb | chr13: 89 Mb-90 Mb | chr2: 52 Mb-53 Mb | chr4: 25 Mb-26 Mb | chr7: 35 Mb-36 Mb |
| chr1: 173 Mb-174 Mb | chr13: 90 Mb-91 Mb | chr2: 53 Mb-54 Mb | chr4: 26 Mb-27 Mb | chr7: 36 Mb-37 Mb |
| chr1: 174 Mb-175 Mb | chr13: 91 Mb-92 Mb | chr2: 54 Mb-55 Mb | chr4: 27 Mb-28 Mb | chr7: 37 Mb-38 Mb |
| chr1: 175 Mb-176 Mb | chr13: 92 Mb-93 Mb | chr2: 55 Mb-56 Mb | chr4: 28 Mb-29 Mb | chr7: 38 Mb-39 Mb |
| chr1: 176 Mb-177 Mb | chr13: 93 Mb-94 Mb | chr2: 56 Mb-57 Mb | chr4: 29 Mb-30 Mb | chr7: 39 Mb-40 Mb |
| chr1: 177 Mb-178 Mb | chr13: 94 Mb-95 Mb | chr2: 57 Mb-58 Mb | chr4: 30 Mb-31 Mb | chr7: 40 Mb-41 Mb |
| chr1: 178 Mb-179 Mb | chr13: 95 Mb-96 Mb | chr2: 58 Mb-59 Mb | chr4: 31 Mb-32 Mb | chr7: 41 Mb-42 Mb |
| chr1: 179 Mb-18 Mb0 | chr13: 96 Mb-97 Mb | chr2: 59 Mb-60 Mb | chr4: 32 Mb-33 Mb | chr7: 42 Mb-43 Mb |
| chr1: 18 Mb0-181 Mb | chr13: 97 Mb-98 Mb | chr2: 60 Mb-61 Mb | chr4: 33 Mb-34 Mb | chr7: 43 Mb-44 Mb |
| chr1: 181 Mb-182 Mb | chr13: 98 Mb-99 Mb | chr2: 61 Mb-62 Mb | chr4: 34 Mb-35 Mb | chr7: 44 Mb-45 Mb |
| chr1: 182 Mb-183 Mb | chr13: 99 Mb-100 Mb | chr2: 62 Mb-63 Mb | chr4: 35 Mb-36 Mb | chr7: 45 Mb-46 Mb |
| chr1: 183 Mb-184 Mb | chr13: 100 Mb-101 Mb | chr2: 63 Mb-64 Mb | chr4: 36 Mb-37 Mb | chr7: 46 Mb-47 Mb |
| chr1: 184 Mb-185 Mb | chr13: 101 Mb-102 Mb | chr2: 64 Mb-65 Mb | chr4: 37 Mb-38 Mb | chr7: 47 Mb-48 Mb |
| chr1: 185 Mb-186 Mb | chr13: 102 Mb-103 Mb | chr2: 65 Mb-66 Mb | chr4: 38 Mb-39 Mb | chr7: 48 Mb-49 Mb |
| chr1: 186 Mb-187 Mb | chr13: 103 Mb-104 Mb | chr2: 66 Mb-67 Mb | chr4: 39 Mb-40 Mb | chr7: 49 Mb-50 Mb |
| chr1: 187 Mb-188 Mb | chr13: 104 Mb-105 Mb | chr2: 67 Mb-68 Mb | chr4: 40 Mb-41 Mb | chr7: 50 Mb-51 Mb |
| chr1: 188 Mb-189 Mb | chr13: 105 Mb-106 Mb | chr2: 68 Mb-69 Mb | chr4: 41 Mb-42 Mb | chr7: 51 Mb-52 Mb |
| chr1: 189 Mb-190 Mb | chr13: 106 Mb-107 Mb | chr2: 69 Mb-70 Mb | chr4: 42 Mb-43 Mb | chr7: 52 Mb-53 Mb |
| chr1: 190 Mb-191 Mb | chr13: 107 Mb-108 Mb | chr2: 70 Mb-71 Mb | chr4: 43 Mb-44 Mb | chr7: 53 Mb-54 Mb |
| chr1: 191 Mb-192 Mb | chr13: 108 Mb-109 Mb | chr2: 71 Mb-72 Mb | chr4: 44 Mb-45 Mb | chr7: 54 Mb-55 Mb |
| chr1: 192 Mb-193 Mb | chr13: 109 Mb-110 Mb | chr2: 72 Mb-73 Mb | chr4: 45 Mb-46 Mb | chr7: 55 Mb-56 Mb |
| chr1: 193 Mb-194 Mb | chr13: 110 Mb-111 Mb | chr2: 73 Mb-74 Mb | chr4: 46 Mb-47 Mb | chr7: 56 Mb-57 Mb |
| chr1: 194 Mb-195 Mb | chr13: 111 Mb-112 Mb | chr2: 74 Mb-75 Mb | chr4: 47 Mb-48 Mb | chr7: 57 Mb-58 Mb |
| chr1: 195 Mb-196 Mb | chr13: 112 Mb-113 Mb | chr2: 75 Mb-76 Mb | chr4: 48 Mb-49 Mb | chr7: 62 Mb-63 Mb |
| chr1: 196 Mb-197 Mb | chr13: 113 Mb-114 Mb | chr2: 76 Mb-77 Mb | chr4: 49 Mb-50 Mb | chr7: 63 Mb-64 Mb |
| chr1: 197 Mb-198 Mb | chr13: 114 Mb-115 Mb | chr2: 77 Mb-78 Mb | chr4: 52 Mb-53 Mb | chr7: 64 Mb-65 Mb |
| chr1: 198 Mb-199 Mb | chr13: 115 Mb-115169878 | chr2: 78 Mb-79 Mb | chr4: 53 Mb-54 Mb | chr7: 65 Mb-66 Mb |
| chr1: 199 Mb-20 Mb0 | chr14: 19 Mb-20 Mb | chr2: 79 Mb-8 Mb0 | chr4: 54 Mb-55 Mb | chr7: 66 Mb-67 Mb |
| chr1: 20 Mb0-201 Mb | chr14: 20 Mb-21 Mb | chr2: 8 Mb0-81 Mb | chr4: 55 Mb-56 Mb | chr7: 67 Mb-68 Mb |
| chr1: 201 Mb-202 Mb | chr14: 21 Mb-22 Mb | chr2: 81 Mb-82 Mb | chr4: 56 Mb-57 Mb | chr7: 68 Mb-69 Mb |
| chr1: 202 Mb-203 Mb | chr14: 22 Mb-23 Mb | chr2: 82 Mb-83 Mb | chr4: 57 Mb-58 Mb | chr7: 69 Mb-70 Mb |
| chr1: 203 Mb-204 Mb | chr14: 23 Mb-24 Mb | chr2: 83 Mb-84 Mb | chr4: 58 Mb-59 Mb | chr7: 70 Mb-71 Mb |
| chr1: 204 Mb-205 Mb | chr14: 24 Mb-25 Mb | chr2: 84 Mb-85 Mb | chr4: 59 Mb-60 Mb | chr7: 71 Mb-72 Mb |

TABLE 1-continued

| | | | | |
|---|---|---|---|---|
| chr1: 205 Mb-206 Mb | chr14: 25 Mb-26 Mb | chr2: 85 Mb-86 Mb | chr4: 60 Mb-61 Mb | chr7: 72 Mb-73 Mb |
| chr1: 206 Mb-207 Mb | chr14: 26 Mb-27 Mb | chr2: 86 Mb-87 Mb | chr4: 61 Mb-62 Mb | chr7: 73 Mb-74 Mb |
| chr1: 207 Mb-208 Mb | chr14: 27 Mb-28 Mb | chr2: 87 Mb-88 Mb | chr4: 62 Mb-63 Mb | chr7: 74 Mb-75 Mb |
| chr1: 208 Mb-209 Mb | chr14: 28 Mb-29 Mb | chr2: 88 Mb-89 Mb | chr4: 63 Mb-64 Mb | chr7: 75 Mb-76 Mb |
| chr1: 209 Mb-210 Mb | chr14: 29 Mb-30 Mb | chr2: 89 Mb-90 Mb | chr4: 64 Mb-65 Mb | chr7: 76 Mb-77 Mb |
| chr1: 210 Mb-211 Mb | chr14: 30 Mb-31 Mb | chr2: 90 Mb-91 Mb | chr4: 65 Mb-66 Mb | chr7: 77 Mb-78 Mb |
| chr1: 211 Mb-212 Mb | chr14: 31 Mb-32 Mb | chr2: 91 Mb-92 Mb | chr4: 66 Mb-67 Mb | chr7: 78 Mb-79 Mb |
| chr1: 212 Mb-213 Mb | chr14: 32 Mb-33 Mb | chr2: 92 Mb-93 Mb | chr4: 67 Mb-68 Mb | chr7: 79 Mb-8 Mb0 |
| chr1: 213 Mb-214 Mb | chr14: 33 Mb-34 Mb | chr2: 95 Mb-96 Mb | chr4: 68 Mb-69 Mb | chr7: 8 Mb0-81 Mb |
| chr1: 214 Mb-215 Mb | chr14: 34 Mb-35 Mb | chr2: 96 Mb-97 Mb | chr4: 69 Mb-70 Mb | chr7: 81 Mb-82 Mb |
| chr1: 215 Mb-216 Mb | chr14: 35 Mb-36 Mb | chr2: 97 Mb-98 Mb | chr4: 70 Mb-71 Mb | chr7: 82 Mb-83 Mb |
| chr1: 216 Mb-217 Mb | chr14: 36 Mb-37 Mb | chr2: 98 Mb-99 Mb | chr4: 71 Mb-72 Mb | chr7: 83 Mb-84 Mb |
| chr1: 217 Mb-218 Mb | chr14: 37 Mb-38 Mb | chr2: 99 Mb-100 Mb | chr4: 72 Mb-73 Mb | chr7: 84 Mb-85 Mb |
| chr1: 218 Mb-219 Mb | chr14: 38 Mb-39 Mb | chr2: 100 Mb-101 Mb | chr4: 73 Mb-74 Mb | chr7: 85 Mb-86 Mb |
| chr1: 219 Mb-220 Mb | chr14: 39 Mb-40 Mb | chr2: 101 Mb-102 Mb | chr4: 74 Mb-75 Mb | chr7: 86 Mb-87 Mb |
| chr1: 220 Mb-221 Mb | chr14: 40 Mb-41 Mb | chr2: 102 Mb-103 Mb | chr4: 75 Mb-76 Mb | chr7: 87 Mb-88 Mb |
| chr1: 221 Mb-222 Mb | chr14: 41 Mb-42 Mb | chr2: 103 Mb-104 Mb | chr4: 76 Mb-77 Mb | chr7: 88 Mb-89 Mb |
| chr1: 222 Mb-223 Mb | chr14: 42 Mb-43 Mb | chr2: 104 Mb-105 Mb | chr4: 77 Mb-78 Mb | chr7: 89 Mb-90 Mb |
| chr1: 223 Mb-224 Mb | chr14: 43 Mb-44 Mb | chr2: 105 Mb-106 Mb | chr4: 78 Mb-79 Mb | chr7: 90 Mb-91 Mb |
| chr1: 224 Mb-225 Mb | chr14: 44 Mb-45 Mb | chr2: 106 Mb-107 Mb | chr4: 79 Mb-8 Mb0 | chr7: 91 Mb-92 Mb |
| chr1: 225 Mb-226 Mb | chr14: 45 Mb-46 Mb | chr2: 107 Mb-108 Mb | chr4: 8 Mb0-81 Mb | chr7: 92 Mb-93 Mb |
| chr1: 226 Mb-227 Mb | chr14: 46 Mb-47 Mb | chr2: 108 Mb-109 Mb | chr4: 81 Mb-82 Mb | chr7: 93 Mb-94 Mb |
| chr1: 227 Mb-228 Mb | chr14: 47 Mb-48 Mb | chr2: 109 Mb-110 Mb | chr4: 82 Mb-83 Mb | chr7: 94 Mb-95 Mb |
| chr1: 228 Mb-229 Mb | chr14: 48 Mb-49 Mb | chr2: 110 Mb-111 Mb | chr4: 83 Mb-84 Mb | chr7: 95 Mb-96 Mb |
| chr1: 229 Mb-230 Mb | chr14: 49 Mb-50 Mb | chr2: 111 Mb-112 Mb | chr4: 84 Mb-85 Mb | chr7: 96 Mb-97 Mb |
| chr1: 230 Mb-231 Mb | chr14: 50 Mb-51 Mb | chr2: 112 Mb-113 Mb | chr4: 85 Mb-86 Mb | chr7: 97 Mb-98 Mb |
| chr1: 231 Mb-232 Mb | chr14: 51 Mb-52 Mb | chr2: 113 Mb-114 Mb | chr4: 86 Mb-87 Mb | chr7: 98 Mb-99 Mb |
| chr1: 232 Mb-233 Mb | chr14: 52 Mb-53 Mb | chr2: 114 Mb-115 Mb | chr4: 87 Mb-88 Mb | chr7: 99 Mb-100 Mb |
| chr1: 233 Mb-234 Mb | chr14: 53 Mb-54 Mb | chr2: 115 Mb-116 Mb | chr4: 88 Mb-89 Mb | chr7: 100 Mb-101 Mb |
| chr1: 234 Mb-235 Mb | chr14: 54 Mb-55 Mb | chr2: 116 Mb-117 Mb | chr4: 89 Mb-90 Mb | chr7: 101 Mb-102 Mb |
| chr1: 235 Mb-236 Mb | chr14: 55 Mb-56 Mb | chr2: 117 Mb-118 Mb | chr4: 90 Mb-91 Mb | chr7: 102 Mb-103 Mb |
| chr1: 236 Mb-237 Mb | chr14: 56 Mb-57 Mb | chr2: 118 Mb-119 Mb | chr4: 91 Mb-92 Mb | chr7: 103 Mb-104 Mb |
| chr1: 237 Mb-238 Mb | chr14: 57 Mb-58 Mb | chr2: 119 Mb-120 Mb | chr4: 92 Mb-93 Mb | chr7: 104 Mb-105 Mb |
| chr1: 238 Mb-239 Mb | chr14: 58 Mb-59 Mb | chr2: 120 Mb-121 Mb | chr4: 93 Mb-94 Mb | chr7: 105 Mb-106 Mb |
| chr1: 239 Mb-240 Mb | chr14: 59 Mb-60 Mb | chr2: 121 Mb-122 Mb | chr4: 94 Mb-95 Mb | chr7: 106 Mb-107 Mb |
| chr1: 240 Mb-241 Mb | chr14: 60 Mb-61 Mb | chr2: 122 Mb-123 Mb | chr4: 95 Mb-96 Mb | chr7: 107 Mb-108 Mb |
| chr1: 241 Mb-242 Mb | chr14: 61 Mb-62 Mb | chr2: 123 Mb-124 Mb | chr4: 96 Mb-97 Mb | chr7: 108 Mb-109 Mb |
| chr1: 242 Mb-243 Mb | chr14: 62 Mb-63 Mb | chr2: 124 Mb-125 Mb | chr4: 97 Mb-98 Mb | chr7: 109 Mb-110 Mb |
| chr1: 243 Mb-244 Mb | chr14: 63 Mb-64 Mb | chr2: 125 Mb-126 Mb | chr4: 98 Mb-99 Mb | chr7: 110 Mb-111 Mb |
| chr1: 244 Mb-245 Mb | chr14: 64 Mb-65 Mb | chr2: 126 Mb-127 Mb | chr4: 99 Mb-100 Mb | chr7: 111 Mb-112 Mb |
| chr1: 245 Mb-246 Mb | chr14: 65 Mb-66 Mb | chr2: 127 Mb-128 Mb | chr4: 100 Mb-101 Mb | chr7: 112 Mb-113 Mb |
| chr1: 246 Mb-247 Mb | chr14: 66 Mb-67 Mb | chr2: 128 Mb-129 Mb | chr4: 101 Mb-102 Mb | chr7: 113 Mb-114 Mb |
| chr1: 247 Mb-248 Mb | chr14: 67 Mb-68 Mb | chr2: 129 Mb-130 Mb | chr4: 102 Mb-103 Mb | chr7: 114 Mb-115 Mb |
| chr1: 248 Mb-249 Mb | chr14: 68 Mb-69 Mb | chr2: 130 Mb-131 Mb | chr4: 103 Mb-104 Mb | chr7: 115 Mb-116 Mb |
| chr1: 249 Mb-249250621 | chr14: 69 Mb-70 Mb | chr2: 131 Mb-132 Mb | chr4: 104 Mb-105 Mb | chr7: 116 Mb-117 Mb |
| chr10: 0-1 Mb | chr14: 70 Mb-71 Mb | chr2: 132 Mb-133 Mb | chr4: 105 Mb-106 Mb | chr7: 117 Mb-118 Mb |
| chr10: 1 Mb-2 Mb | chr14: 71 Mb-72 Mb | chr2: 133 Mb-134 Mb | chr4: 106 Mb-107 Mb | chr7: 118 Mb-119 Mb |
| chr10: 2 Mb-3 Mb | chr14: 72 Mb-73 Mb | chr2: 134 Mb-135 Mb | chr4: 107 Mb-108 Mb | chr7: 119 Mb-120 Mb |
| chr10: 3 Mb-4 Mb | chr14: 73 Mb-74 Mb | chr2: 135 Mb-136 Mb | chr4: 108 Mb-109 Mb | chr7: 120 Mb-121 Mb |
| chr10: 4 Mb-5 Mb | chr14: 74 Mb-75 Mb | chr2: 136 Mb-137 Mb | chr4: 109 Mb-110 Mb | chr7: 121 Mb-122 Mb |
| chr10: 5 Mb-6 Mb | chr14: 75 Mb-76 Mb | chr2: 137 Mb-138 Mb | chr4: 110 Mb-111 Mb | chr7: 122 Mb-123 Mb |
| chr10: 6 Mb-7 Mb | chr14: 76 Mb-77 Mb | chr2: 138 Mb-139 Mb | chr4: 111 Mb-112 Mb | chr7: 123 Mb-124 Mb |
| chr10: 7 Mb-8 Mb | chr14: 77 Mb-78 Mb | chr2: 139 Mb-140 Mb | chr4: 112 Mb-113 Mb | chr7: 124 Mb-125 Mb |
| chr10: 8 Mb-9 Mb | chr14: 78 Mb-79 Mb | chr2: 140 Mb-141 Mb | chr4: 113 Mb-114 Mb | chr7: 125 Mb-126 Mb |
| chr10: 9 Mb-10 Mb | chr14: 79 Mb-8 Mb0 | chr2: 141 Mb-142 Mb | chr4: 114 Mb-115 Mb | chr7: 126 Mb-127 Mb |
| chr10: 10 Mb-11 Mb | chr14: 8 Mb0-81 Mb | chr2: 142 Mb-143 Mb | chr4: 115 Mb-116 Mb | chr7: 127 Mb-128 Mb |
| chr10: 11 Mb-12 Mb | chr14: 81 Mb-82 Mb | chr2: 143 Mb-144 Mb | chr4: 116 Mb-117 Mb | chr7: 128 Mb-129 Mb |
| chr10: 12 Mb-13 Mb | chr14: 82 Mb-83 Mb | chr2: 144 Mb-145 Mb | chr4: 117 Mb-118 Mb | chr7: 129 Mb-130 Mb |
| chr10: 13 Mb-14 Mb | chr14: 83 Mb-84 Mb | chr2: 145 Mb-146 Mb | chr4: 118 Mb-119 Mb | chr7: 130 Mb-131 Mb |
| chr10: 14 Mb-15 Mb | chr14: 84 Mb-85 Mb | chr2: 146 Mb-147 Mb | chr4: 119 Mb-120 Mb | chr7: 131 Mb-132 Mb |
| chr10: 15 Mb-16 Mb | chr14: 85 Mb-86 Mb | chr2: 147 Mb-148 Mb | chr4: 120 Mb-121 Mb | chr7: 132 Mb-133 Mb |
| chr10: 16 Mb-17 Mb | chr14: 86 Mb-87 Mb | chr2: 148 Mb-149 Mb | chr4: 121 Mb-122 Mb | chr7: 133 Mb-134 Mb |
| chr10: 17 Mb-18 Mb | chr14: 87 Mb-88 Mb | chr2: 149 Mb-150 Mb | chr4: 122 Mb-123 Mb | chr7: 134 Mb-135 Mb |
| chr10: 18 Mb-19 Mb | chr14: 88 Mb-89 Mb | chr2: 150 Mb-151 Mb | chr4: 123 Mb-124 Mb | chr7: 135 Mb-136 Mb |
| chr10: 19 Mb-20 Mb | chr14: 89 Mb-90 Mb | chr2: 151 Mb-152 Mb | chr4: 124 Mb-125 Mb | chr7: 136 Mb-137 Mb |
| chr10: 20 Mb-21 Mb | chr14: 90 Mb-91 Mb | chr2: 152 Mb-153 Mb | chr4: 125 Mb-126 Mb | chr7: 137 Mb-138 Mb |
| chr10: 21 Mb-22 Mb | chr14: 91 Mb-92 Mb | chr2: 153 Mb-154 Mb | chr4: 126 Mb-127 Mb | chr7: 138 Mb-139 Mb |
| chr10: 22 Mb-23 Mb | chr14: 92 Mb-93 Mb | chr2: 154 Mb-155 Mb | chr4: 127 Mb-128 Mb | chr7: 139 Mb-140 Mb |
| chr10: 23 Mb-24 Mb | chr14: 93 Mb-94 Mb | chr2: 155 Mb-156 Mb | chr4: 128 Mb-129 Mb | chr7: 140 Mb-141 Mb |
| chr10: 24 Mb-25 Mb | chr14: 94 Mb-95 Mb | chr2: 156 Mb-157 Mb | chr4: 129 Mb-130 Mb | chr7: 141 Mb-142 Mb |
| chr10: 25 Mb-26 Mb | chr14: 95 Mb-96 Mb | chr2: 157 Mb-158 Mb | chr4: 130 Mb-131 Mb | chr7: 142 Mb-143 Mb |
| chr10: 26 Mb-27 Mb | chr14: 96 Mb-97 Mb | chr2: 158 Mb-159 Mb | chr4: 131 Mb-132 Mb | chr7: 143 Mb-144 Mb |
| chr10: 27 Mb-28 Mb | chr14: 97 Mb-98 Mb | chr2: 159 Mb-160 Mb | chr4: 132 Mb-133 Mb | chr7: 144 Mb-145 Mb |
| chr10: 28 Mb-29 Mb | chr14: 98 Mb-99 Mb | chr2: 160 Mb-161 Mb | chr4: 133 Mb-134 Mb | chr7: 145 Mb-146 Mb |
| chr10: 29 Mb-30 Mb | chr14: 99 Mb-100 Mb | chr2: 161 Mb-162 Mb | chr4: 134 Mb-135 Mb | chr7: 146 Mb-147 Mb |
| chr10: 30 Mb-31 Mb | chr14: 100 Mb-101 Mb | chr2: 162 Mb-163 Mb | chr4: 135 Mb-136 Mb | chr7: 147 Mb-148 Mb |
| chr10: 31 Mb-32 Mb | chr14: 101 Mb-102 Mb | chr2: 163 Mb-164 Mb | chr4: 136 Mb-137 Mb | chr7: 148 Mb-149 Mb |
| chr10: 32 Mb-33 Mb | chr14: 102 Mb-103 Mb | chr2: 164 Mb-165 Mb | chr4: 137 Mb-138 Mb | chr7: 149 Mb-150 Mb |
| chr10: 33 Mb-34 Mb | chr14: 103 Mb-104 Mb | chr2: 165 Mb-166 Mb | chr4: 138 Mb-139 Mb | chr7: 150 Mb-151 Mb |
| chr10: 34 Mb-35 Mb | chr14: 104 Mb-105 Mb | chr2: 166 Mb-167 Mb | chr4: 139 Mb-140 Mb | chr7: 151 Mb-152 Mb |

TABLE 1-continued

| | | | | |
|---|---|---|---|---|
| chr10: 35 Mb-36 Mb | chr14: 105 Mb-106 Mb | chr2: 167 Mb-168 Mb | chr4: 140 Mb-141 Mb | chr7: 152 Mb-153 Mb |
| chr10: 36 Mb-37 Mb | chr14: 106 Mb-107 Mb | chr2: 168 Mb-169 Mb | chr4: 141 Mb-142 Mb | chr7: 153 Mb-154 Mb |
| chr10: 37 Mb-38 Mb | chr14: 107 Mb-107349540 | chr2: 169 Mb-170 Mb | chr4: 142 Mb-143 Mb | chr7: 154 Mb-155 Mb |
| chr10: 38 Mb-39 Mb | chr15: 20 Mb-21 Mb | chr2: 170 Mb-171 Mb | chr4: 143 Mb-144 Mb | chr7: 155 Mb-156 Mb |
| chr10: 39 Mb-40 Mb | chr15: 21 Mb-22 Mb | chr2: 171 Mb-172 Mb | chr4: 144 Mb-145 Mb | chr7: 156 Mb-157 Mb |
| chr10: 42 Mb-43 Mb | chr15: 22 Mb-23 Mb | chr2: 172 Mb-173 Mb | chr4: 145 Mb-146 Mb | chr7: 157 Mb-158 Mb |
| chr10: 43 Mb-44 Mb | chr15: 23 Mb-24 Mb | chr2: 173 Mb-174 Mb | chr4: 146 Mb-147 Mb | chr7: 158 Mb-159 Mb |
| chr10: 44 Mb-45 Mb | chr15: 24 Mb-25 Mb | chr2: 174 Mb-175 Mb | chr4: 147 Mb-148 Mb | chr7: 159 Mb-159138663 |
| chr10: 45 Mb-46 Mb | chr15: 25 Mb-26 Mb | chr2: 175 Mb-176 Mb | chr4: 148 Mb-149 Mb | chr8: 0-1 Mb |
| chr10: 46 Mb-47 Mb | chr15: 26 Mb-27 Mb | chr2: 176 Mb-177 Mb | chr4: 149 Mb-150 Mb | chr8: 1 Mb-2 Mb |
| chr10: 47 Mb-48 Mb | chr15: 27 Mb-28 Mb | chr2: 177 Mb-178 Mb | chr4: 150 Mb-151 Mb | chr8: 2 Mb-3 Mb |
| chr10: 48 Mb-49 Mb | chr15: 28 Mb-29 Mb | chr2: 178 Mb-179 Mb | chr4: 151 Mb-152 Mb | chr8: 3 Mb-4 Mb |
| chr10: 49 Mb-50 Mb | chr15: 29 Mb-30 Mb | chr2: 179 Mb-18 Mb0 | chr4: 152 Mb-153 Mb | chr8: 4 Mb-5 Mb |
| chr10: 50 Mb-51 Mb | chr15: 30 Mb-31 Mb | chr2: 18 Mb0-181 Mb | chr4: 153 Mb-154 Mb | chr8: 5 Mb-6 Mb |
| chr10: 51 Mb-52 Mb | chr15: 31 Mb-32 Mb | chr2: 181 Mb-182 Mb | chr4: 154 Mb-155 Mb | chr8: 6 Mb-7 Mb |
| chr10: 52 Mb-53 Mb | chr15: 32 Mb-33 Mb | chr2: 182 Mb-183 Mb | chr4: 155 Mb-156 Mb | chr8: 7 Mb-8 Mb |
| chr10: 53 Mb-54 Mb | chr15: 33 Mb-34 Mb | chr2: 183 Mb-184 Mb | chr4: 156 Mb-157 Mb | chr8: 8 Mb-9 Mb |
| chr10: 54 Mb-55 Mb | chr15: 34 Mb-35 Mb | chr2: 184 Mb-185 Mb | chr4: 157 Mb-158 Mb | chr8: 9 Mb-10 Mb |
| chr10: 55 Mb-56 Mb | chr15: 35 Mb-36 Mb | chr2: 185 Mb-186 Mb | chr4: 158 Mb-159 Mb | chr8: 10 Mb-11 Mb |
| chr10: 56 Mb-57 Mb | chr15: 36 Mb-37 Mb | chr2: 186 Mb-187 Mb | chr4: 159 Mb-160 Mb | chr8: 11 Mb-12 Mb |
| chr10: 57 Mb-58 Mb | chr15: 37 Mb-38 Mb | chr2: 187 Mb-188 Mb | chr4: 160 Mb-161 Mb | chr8: 12 Mb-13 Mb |
| chr10: 58 Mb-59 Mb | chr15: 38 Mb-39 Mb | chr2: 188 Mb-189 Mb | chr4: 161 Mb-162 Mb | chr8: 13 Mb-14 Mb |
| chr10: 59 Mb-60 Mb | chr15: 39 Mb-40 Mb | chr2: 189 Mb-190 Mb | chr4: 162 Mb-163 Mb | chr8: 14 Mb-15 Mb |
| chr10: 60 Mb-61 Mb | chr15: 40 Mb-41 Mb | chr2: 190 Mb-191 Mb | chr4: 163 Mb-164 Mb | chr8: 15 Mb-16 Mb |
| chr10: 61 Mb-62 Mb | chr15: 41 Mb-42 Mb | chr2: 191 Mb-192 Mb | chr4: 164 Mb-165 Mb | chr8: 16 Mb-17 Mb |
| chr10: 62 Mb-63 Mb | chr15: 42 Mb-43 Mb | chr2: 192 Mb-193 Mb | chr4: 165 Mb-166 Mb | chr8: 17 Mb-18 Mb |
| chr10: 63 Mb-64 Mb | chr15: 43 Mb-44 Mb | chr2: 193 Mb-194 Mb | chr4: 166 Mb-167 Mb | chr8: 18 Mb-19 Mb |
| chr10: 64 Mb-65 Mb | chr15: 44 Mb-45 Mb | chr2: 194 Mb-195 Mb | chr4: 167 Mb-168 Mb | chr8: 19 Mb-20 Mb |
| chr10: 65 Mb-66 Mb | chr15: 45 Mb-46 Mb | chr2: 195 Mb-196 Mb | chr4: 168 Mb-169 Mb | chr8: 20 Mb-21 Mb |
| chr10: 66 Mb-67 Mb | chr15: 46 Mb-47 Mb | chr2: 196 Mb-197 Mb | chr4: 169 Mb-170 Mb | chr8: 21 Mb-22 Mb |
| chr10: 67 Mb-68 Mb | chr15: 47 Mb-48 Mb | chr2: 197 Mb-198 Mb | chr4: 170 Mb-171 Mb | chr8: 22 Mb-23 Mb |
| chr10: 68 Mb-69 Mb | chr15: 48 Mb-49 Mb | chr2: 198 Mb-199 Mb | chr4: 171 Mb-172 Mb | chr8: 23 Mb-24 Mb |
| chr10: 69 Mb-70 Mb | chr15: 49 Mb-50 Mb | chr2: 199 Mb-20 Mb0 | chr4: 172 Mb-173 Mb | chr8: 24 Mb-25 Mb |
| chr10: 70 Mb-71 Mb | chr15: 50 Mb-51 Mb | chr2: 20 Mb0-201 Mb | chr4: 173 Mb-174 Mb | chr8: 25 Mb-26 Mb |
| chr10: 71 Mb-72 Mb | chr15: 51 Mb-52 Mb | chr2: 201 Mb-202 Mb | chr4: 174 Mb-175 Mb | chr8: 26 Mb-27 Mb |
| chr10: 72 Mb-73 Mb | chr15: 52 Mb-53 Mb | chr2: 202 Mb-203 Mb | chr4: 175 Mb-176 Mb | chr8: 27 Mb-28 Mb |
| chr10: 73 Mb-74 Mb | chr15: 53 Mb-54 Mb | chr2: 203 Mb-204 Mb | chr4: 176 Mb-177 Mb | chr8: 28 Mb-29 Mb |
| chr10: 74 Mb-75 Mb | chr15: 54 Mb-55 Mb | chr2: 204 Mb-205 Mb | chr4: 177 Mb-178 Mb | chr8: 29 Mb-30 Mb |
| chr10: 75 Mb-76 Mb | chr15: 55 Mb-56 Mb | chr2: 205 Mb-206 Mb | chr4: 178 Mb-179 Mb | chr8: 30 Mb-31 Mb |
| chr10: 76 Mb-77 Mb | chr15: 56 Mb-57 Mb | chr2: 206 Mb-207 Mb | chr4: 179 Mb-18 Mb0 | chr8: 31 Mb-32 Mb |
| chr10: 77 Mb-78 Mb | chr15: 57 Mb-58 Mb | chr2: 207 Mb-208 Mb | chr4: 18 Mb0-181 Mb | chr8: 32 Mb-33 Mb |
| chr10: 78 Mb-79 Mb | chr15: 58 Mb-59 Mb | chr2: 208 Mb-209 Mb | chr4: 181 Mb-182 Mb | chr8: 33 Mb-34 Mb |
| chr10: 79 Mb-8 Mb0 | chr15: 59 Mb-60 Mb | chr2: 209 Mb-210 Mb | chr4: 182 Mb-183 Mb | chr8: 34 Mb-35 Mb |
| chr10: 8 Mb0-81 Mb | chr15: 60 Mb-61 Mb | chr2: 210 Mb-211 Mb | chr4: 183 Mb-184 Mb | chr8: 35 Mb-36 Mb |
| chr10: 81 Mb-82 Mb | chr15: 61 Mb-62 Mb | chr2: 211 Mb-212 Mb | chr4: 184 Mb-185 Mb | chr8: 36 Mb-37 Mb |
| chr10: 82 Mb-83 Mb | chr15: 62 Mb-63 Mb | chr2: 212 Mb-213 Mb | chr4: 185 Mb-186 Mb | chr8: 37 Mb-38 Mb |
| chr10: 83 Mb-84 Mb | chr15: 63 Mb-64 Mb | chr2: 213 Mb-214 Mb | chr4: 186 Mb-187 Mb | chr8: 38 Mb-39 Mb |
| chr10: 84 Mb-85 Mb | chr15: 64 Mb-65 Mb | chr2: 214 Mb-215 Mb | chr4: 187 Mb-188 Mb | chr8: 39 Mb-40 Mb |
| chr10: 85 Mb-86 Mb | chr15: 65 Mb-66 Mb | chr2: 215 Mb-216 Mb | chr4: 188 Mb-189 Mb | chr8: 40 Mb-41 Mb |
| chr10: 86 Mb-87 Mb | chr15: 66 Mb-67 Mb | chr2: 216 Mb-217 Mb | chr4: 189 Mb-190 Mb | chr8: 41 Mb-42 Mb |
| chr10: 87 Mb-88 Mb | chr15: 67 Mb-68 Mb | chr2: 217 Mb-218 Mb | chr4: 190 Mb-191 Mb | chr8: 42 Mb-43 Mb |
| chr10: 88 Mb-89 Mb | chr15: 68 Mb-69 Mb | chr2: 218 Mb-219 Mb | chr4: 191 Mb-191154276 | chr8: 43 Mb-44 Mb |
| chr10: 89 Mb-90 Mb | chr15: 69 Mb-70 Mb | chr2: 219 Mb-220 Mb | chr5: 0-1 Mb | chr8: 47 Mb-48 Mb |
| chr10: 90 Mb-91 Mb | chr15: 70 Mb-71 Mb | chr2: 220 Mb-221 Mb | chr5: 1 Mb-2 Mb | chr8: 48 Mb-49 Mb |
| chr10: 91 Mb-92 Mb | chr15: 71 Mb-72 Mb | chr2: 221 Mb-222 Mb | chr5: 2 Mb-3 Mb | chr8: 49 Mb-50 Mb |
| chr10: 92 Mb-93 Mb | chr15: 72 Mb-73 Mb | chr2: 222 Mb-223 Mb | chr5: 3 Mb-4 Mb | chr8: 50 Mb-51 Mb |
| chr10: 93 Mb-94 Mb | chr15: 73 Mb-74 Mb | chr2: 223 Mb-224 Mb | chr5: 4 Mb-5 Mb | chr8: 51 Mb-52 Mb |
| chr10: 94 Mb-95 Mb | chr15: 74 Mb-75 Mb | chr2: 224 Mb-225 Mb | chr5: 5 Mb-6 Mb | chr8: 52 Mb-53 Mb |
| chr10: 95 Mb-96 Mb | chr15: 75 Mb-76 Mb | chr2: 225 Mb-226 Mb | chr5: 6 Mb-7 Mb | chr8: 53 Mb-54 Mb |
| chr10: 96 Mb-97 Mb | chr15: 76 Mb-77 Mb | chr2: 226 Mb-227 Mb | chr5: 7 Mb-8 Mb | chr8: 54 Mb-55 Mb |
| chr10: 97 Mb-98 Mb | chr15: 77 Mb-78 Mb | chr2: 227 Mb-228 Mb | chr5: 8 Mb-9 Mb | chr8: 55 Mb-56 Mb |
| chr10: 98 Mb-99 Mb | chr15: 78 Mb-79 Mb | chr2: 228 Mb-229 Mb | chr5: 9 Mb-10 Mb | chr8: 56 Mb-57 Mb |
| chr10: 99 Mb-100 Mb | chr15: 79 Mb-8 Mb0 | chr2: 229 Mb-230 Mb | chr5: 10 Mb-11 Mb | chr8: 57 Mb-58 Mb |
| chr10: 100 Mb-101 Mb | chr15: 8 Mb0-81 Mb | chr2: 230 Mb-231 Mb | chr5: 11 Mb-12 Mb | chr8: 58 Mb-59 Mb |
| chr10: 101 Mb-102 Mb | chr15: 81 Mb-82 Mb | chr2: 231 Mb-232 Mb | chr5: 12 Mb-13 Mb | chr8: 59 Mb-60 Mb |
| chr10: 102 Mb-103 Mb | chr15: 82 Mb-83 Mb | chr2: 232 Mb-233 Mb | chr5: 13 Mb-14 Mb | chr8: 60 Mb-61 Mb |
| chr10: 103 Mb-104 Mb | chr15: 83 Mb-84 Mb | chr2: 233 Mb-234 Mb | chr5: 14 Mb-15 Mb | chr8: 61 Mb-62 Mb |
| chr10: 104 Mb-105 Mb | chr15: 84 Mb-85 Mb | chr2: 234 Mb-235 Mb | chr5: 15 Mb-16 Mb | chr8: 62 Mb-63 Mb |
| chr10: 105 Mb-106 Mb | chr15: 85 Mb-86 Mb | chr2: 235 Mb-236 Mb | chr5: 16 Mb-17 Mb | chr8: 63 Mb-64 Mb |
| chr10: 106 Mb-107 Mb | chr15: 86 Mb-87 Mb | chr2: 236 Mb-237 Mb | chr5: 17 Mb-18 Mb | chr8: 64 Mb-65 Mb |
| chr10: 107 Mb-108 Mb | chr15: 87 Mb-88 Mb | chr2: 237 Mb-238 Mb | chr5: 18 Mb-19 Mb | chr8: 65 Mb-66 Mb |
| chr10: 108 Mb-109 Mb | chr15: 88 Mb-89 Mb | chr2: 238 Mb-239 Mb | chr5: 19 Mb-20 Mb | chr8: 66 Mb-67 Mb |
| chr10: 109 Mb-110 Mb | chr15: 89 Mb-90 Mb | chr2: 239 Mb-240 Mb | chr5: 20 Mb-21 Mb | chr8: 67 Mb-68 Mb |
| chr10: 110 Mb-111 Mb | chr15: 90 Mb-91 Mb | chr2: 240 Mb-241 Mb | chr5: 21 Mb-22 Mb | chr8: 68 Mb-69 Mb |
| chr10: 111 Mb-112 Mb | chr15: 91 Mb-92 Mb | chr2: 241 Mb-242 Mb | chr5: 22 Mb-23 Mb | chr8: 69 Mb-70 Mb |
| chr10: 112 Mb-113 Mb | chr15: 92 Mb-93 Mb | chr2: 242 Mb-243 Mb | chr5: 23 Mb-24 Mb | chr8: 70 Mb-71 Mb |
| chr10: 113 Mb-114 Mb | chr15: 93 Mb-94 Mb | chr2: 243 Mb-243199373 | chr5: 24 Mb-25 Mb | chr8: 71 Mb-72 Mb |
| chr10: 114 Mb-115 Mb | chr15: 94 Mb-95 Mb | chr20: 0-1 Mb | chr5: 25 Mb-26 Mb | chr8: 72 Mb-73 Mb |
| chr10: 115 Mb-116 Mb | chr15: 95 Mb-96 Mb | chr20: 1 Mb-2 Mb | chr5: 26 Mb-27 Mb | chr8: 73 Mb-74 Mb |
| chr10: 116 Mb-117 Mb | chr15: 96 Mb-97 Mb | chr20: 2 Mb-3 Mb | chr5: 27 Mb-28 Mb | chr8: 74 Mb-75 Mb |

TABLE 1-continued

| | | | | |
|---|---|---|---|---|
| chr10: 117 Mb-118 Mb | chr15: 97 Mb-98 Mb | chr20: 3 Mb-4 Mb | chr5: 28 Mb-29 Mb | chr8: 75 Mb-76 Mb |
| chr10: 118 Mb-119 Mb | chr15: 98 Mb-99 Mb | chr20: 4 Mb-5 Mb | chr5: 29 Mb-30 Mb | chr8: 76 Mb-77 Mb |
| chr10: 119 Mb-120 Mb | chr15: 99 Mb-100 Mb | chr20: 5 Mb-6 Mb | chr5: 30 Mb-31 Mb | chr8: 77 Mb-78 Mb |
| chr10: 120 Mb-121 Mb | chr15: 100 Mb-101 Mb | chr20: 6 Mb-7 Mb | chr5: 31 Mb-32 Mb | chr8: 78 Mb-79 Mb |
| chr10: 121 Mb-122 Mb | chr15: 101 Mb-102 Mb | chr20: 7 Mb-8 Mb | chr5: 32 Mb-33 Mb | chr8: 79 Mb-8 Mb0 |
| chr10: 122 Mb-123 Mb | chr15: 102 Mb-102531392 | chr20: 8 Mb-9 Mb | chr5: 33 Mb-34 Mb | chr8: 8 Mb0-81 Mb |
| chr10: 123 Mb-124 Mb | chr16: 0-1 Mb | chr20: 9 Mb-10 Mb | chr5: 34 Mb-35 Mb | chr8: 81 Mb-82 Mb |
| chr10: 124 Mb-125 Mb | chr16: 1 Mb-2 Mb | chr20: 10 Mb-11 Mb | chr5: 35 Mb-36 Mb | chr8: 82 Mb-83 Mb |
| chr10: 125 Mb-126 Mb | chr16: 2 Mb-3 Mb | chr20: 11 Mb-12 Mb | chr5: 36 Mb-37 Mb | chr8: 83 Mb-84 Mb |
| chr10: 126 Mb-127 Mb | chr16: 3 Mb-4 Mb | chr20: 12 Mb-13 Mb | chr5: 37 Mb-38 Mb | chr8: 84 Mb-85 Mb |
| chr10: 127 Mb-128 Mb | chr16: 4 Mb-5 Mb | chr20: 13 Mb-14 Mb | chr5: 38 Mb-39 Mb | chr8: 85 Mb-86 Mb |
| chr10: 128 Mb-129 Mb | chr16: 5 Mb-6 Mb | chr20: 14 Mb-15 Mb | chr5: 39 Mb-40 Mb | chr8: 86 Mb-87 Mb |
| chr10: 129 Mb-130 Mb | chr16: 6 Mb-7 Mb | chr20: 15 Mb-16 Mb | chr5: 40 Mb-41 Mb | chr8: 87 Mb-88 Mb |
| chr10: 130 Mb-131 Mb | chr16: 7 Mb-8 Mb | chr20: 16 Mb-17 Mb | chr5: 41 Mb-42 Mb | chr8: 88 Mb-89 Mb |
| chr10: 131 Mb-132 Mb | chr16: 8 Mb-9 Mb | chr20: 17 Mb-18 Mb | chr5: 42 Mb-43 Mb | chr8: 89 Mb-90 Mb |
| chr10: 132 Mb-133 Mb | chr16: 9 Mb-10 Mb | chr20: 18 Mb-19 Mb | chr5: 43 Mb-44 Mb | chr8: 90 Mb-91 Mb |
| chr10: 133 Mb-134 Mb | chr16: 10 Mb-11 Mb | chr20: 19 Mb-20 Mb | chr5: 44 Mb-45 Mb | chr8: 91 Mb-92 Mb |
| chr10: 134 Mb-135 Mb | chr16: 11 Mb-12 Mb | chr20: 20 Mb-21 Mb | chr5: 45 Mb-46 Mb | chr8: 92 Mb-93 Mb |
| chr10: 135 Mb-135534747 | chr16: 12 Mb-13 Mb | chr20: 21 Mb-22 Mb | chr5: 49 Mb-50 Mb | chr8: 93 Mb-94 Mb |
| chr11: 0-1 Mb | chr16: 13 Mb-14 Mb | chr20: 22 Mb-23 Mb | chr5: 50 Mb-51 Mb | chr8: 94 Mb-95 Mb |
| chr11: 1 Mb-2 Mb | chr16: 14 Mb-15 Mb | chr20: 23 Mb-24 Mb | chr5: 51 Mb-52 Mb | chr8: 95 Mb-96 Mb |
| chr11: 2 Mb-3 Mb | chr16: 15 Mb-16 Mb | chr20: 24 Mb-25 Mb | chr5: 52 Mb-53 Mb | chr8: 96 Mb-97 Mb |
| chr11: 3 Mb-4 Mb | chr16: 16 Mb-17 Mb | chr20: 25 Mb-26 Mb | chr5: 53 Mb-54 Mb | chr8: 97 Mb-98 Mb |
| chr11: 4 Mb-5 Mb | chr16: 17 Mb-18 Mb | chr20: 26 Mb-27 Mb | chr5: 54 Mb-55 Mb | chr8: 98 Mb-99 Mb |
| chr11: 5 Mb-6 Mb | chr16: 18 Mb-19 Mb | chr20: 29 Mb-30 Mb | chr5: 55 Mb-56 Mb | chr8: 99 Mb-100 Mb |
| chr11: 6 Mb-7 Mb | chr16: 19 Mb-20 Mb | chr20: 30 Mb-31 Mb | chr5: 56 Mb-57 Mb | chr8: 100 Mb-101 Mb |
| chr11: 7 Mb-8 Mb | chr16: 20 Mb-21 Mb | chr20: 31 Mb-32 Mb | chr5: 57 Mb-58 Mb | chr8: 101 Mb-102 Mb |
| chr11: 8 Mb-9 Mb | chr16: 21 Mb-22 Mb | chr20: 32 Mb-33 Mb | chr5: 58 Mb-59 Mb | chr8: 102 Mb-103 Mb |
| chr11: 9 Mb-10 Mb | chr16: 22 Mb-23 Mb | chr20: 33 Mb-34 Mb | chr5: 59 Mb-60 Mb | chr8: 103 Mb-104 Mb |
| chr11: 10 Mb-11 Mb | chr16: 23 Mb-24 Mb | chr20: 34 Mb-35 Mb | chr5: 60 Mb-61 Mb | chr8: 104 Mb-105 Mb |
| chr11: 11 Mb-12 Mb | chr16: 24 Mb-25 Mb | chr20: 35 Mb-36 Mb | chr5: 61 Mb-62 Mb | chr8: 105 Mb-106 Mb |
| chr11: 12 Mb-13 Mb | chr16: 25 Mb-26 Mb | chr20: 36 Mb-37 Mb | chr5: 62 Mb-63 Mb | chr8: 106 Mb-107 Mb |
| chr11: 13 Mb-14 Mb | chr16: 26 Mb-27 Mb | chr20: 37 Mb-38 Mb | chr5: 63 Mb-64 Mb | chr8: 107 Mb-108 Mb |
| chr11: 14 Mb-15 Mb | chr16: 27 Mb-28 Mb | chr20: 38 Mb-39 Mb | chr5: 64 Mb-65 Mb | chr8: 108 Mb-109 Mb |
| chr11: 15 Mb-16 Mb | chr16: 28 Mb-29 Mb | chr20: 39 Mb-40 Mb | chr5: 65 Mb-66 Mb | chr8: 109 Mb-110 Mb |
| chr11: 16 Mb-17 Mb | chr16: 29 Mb-30 Mb | chr20: 40 Mb-41 Mb | chr5: 66 Mb-67 Mb | chr8: 110 Mb-111 Mb |
| chr11: 17 Mb-18 Mb | chr16: 30 Mb-31 Mb | chr20: 41 Mb-42 Mb | chr5: 67 Mb-68 Mb | chr8: 111 Mb-112 Mb |
| chr11: 18 Mb-19 Mb | chr16: 31 Mb-32 Mb | chr20: 42 Mb-43 Mb | chr5: 68 Mb-69 Mb | chr8: 112 Mb-113 Mb |
| chr11: 19 Mb-20 Mb | chr16: 32 Mb-33 Mb | chr20: 43 Mb-44 Mb | chr5: 69 Mb-70 Mb | chr8: 113 Mb-114 Mb |
| chr11: 20 Mb-21 Mb | chr16: 33 Mb-34 Mb | chr20: 44 Mb-45 Mb | chr5: 70 Mb-71 Mb | chr8: 114 Mb-115 Mb |
| chr11: 21 Mb-22 Mb | chr16: 34 Mb-35 Mb | chr20: 45 Mb-46 Mb | chr5: 71 Mb-72 Mb | chr8: 115 Mb-116 Mb |
| chr11: 22 Mb-23 Mb | chr16: 35 Mb-36 Mb | chr20: 46 Mb-47 Mb | chr5: 72 Mb-73 Mb | chr8: 116 Mb-117 Mb |
| chr11: 23 Mb-24 Mb | chr16: 46 Mb-47 Mb | chr20: 47 Mb-48 Mb | chr5: 73 Mb-74 Mb | chr8: 117 Mb-118 Mb |
| chr11: 24 Mb-25 Mb | chr16: 47 Mb-48 Mb | chr20: 48 Mb-49 Mb | chr5: 74 Mb-75 Mb | chr8: 118 Mb-119 Mb |
| chr11: 25 Mb-26 Mb | chr16: 48 Mb-49 Mb | chr20: 49 Mb-50 Mb | chr5: 75 Mb-76 Mb | chr8: 119 Mb-120 Mb |
| chr11: 26 Mb-27 Mb | chr16: 49 Mb-50 Mb | chr20: 50 Mb-51 Mb | chr5: 76 Mb-77 Mb | chr8: 120 Mb-121 Mb |
| chr11: 27 Mb-28 Mb | chr16: 50 Mb-51 Mb | chr20: 51 Mb-52 Mb | chr5: 77 Mb-78 Mb | chr8: 121 Mb-122 Mb |
| chr11: 28 Mb-29 Mb | chr16: 51 Mb-52 Mb | chr20: 52 Mb-53 Mb | chr5: 78 Mb-79 Mb | chr8: 122 Mb-123 Mb |
| chr11: 29 Mb-30 Mb | chr16: 52 Mb-53 Mb | chr20: 53 Mb-54 Mb | chr5: 79 Mb-8 Mb0 | chr8: 123 Mb-124 Mb |
| chr11: 30 Mb-31 Mb | chr16: 53 Mb-54 Mb | chr20: 54 Mb-55 Mb | chr5: 8 Mb0-81 Mb | chr8: 124 Mb-125 Mb |
| chr11: 31 Mb-32 Mb | chr16: 54 Mb-55 Mb | chr20: 55 Mb-56 Mb | chr5: 81 Mb-82 Mb | chr8: 125 Mb-126 Mb |
| chr11: 32 Mb-33 Mb | chr16: 55 Mb-56 Mb | chr20: 56 Mb-57 Mb | chr5: 82 Mb-83 Mb | chr8: 126 Mb-127 Mb |
| chr11: 33 Mb-34 Mb | chr16: 56 Mb-57 Mb | chr20: 57 Mb-58 Mb | chr5: 83 Mb-84 Mb | chr8: 127 Mb-128 Mb |
| chr11: 34 Mb-35 Mb | chr16: 57 Mb-58 Mb | chr20: 58 Mb-59 Mb | chr5: 84 Mb-85 Mb | chr8: 128 Mb-129 Mb |
| chr11: 35 Mb-36 Mb | chr16: 58 Mb-59 Mb | chr20: 59 Mb-60 Mb | chr5: 85 Mb-86 Mb | chr8: 129 Mb-130 Mb |
| chr11: 36 Mb-37 Mb | chr16: 59 Mb-60 Mb | chr20: 60 Mb-61 Mb | chr5: 86 Mb-87 Mb | chr8: 130 Mb-131 Mb |
| chr11: 37 Mb-38 Mb | chr16: 60 Mb-61 Mb | chr20: 61 Mb-62 Mb | chr5: 87 Mb-88 Mb | chr8: 131 Mb-132 Mb |
| chr11: 38 Mb-39 Mb | chr16: 61 Mb-62 Mb | chr20: 62 Mb-63 Mb | chr5: 88 Mb-89 Mb | chr8: 132 Mb-133 Mb |
| chr11: 39 Mb-40 Mb | chr16: 62 Mb-63 Mb | chr21: 9 Mb-10 Mb | chr5: 89 Mb-90 Mb | chr8: 133 Mb-134 Mb |
| chr11: 40 Mb-41 Mb | chr16: 63 Mb-64 Mb | chr21: 10 Mb-11 Mb | chr5: 90 Mb-91 Mb | chr8: 134 Mb-135 Mb |
| chr11: 41 Mb-42 Mb | chr16: 64 Mb-65 Mb | chr21: 11 Mb-12 Mb | chr5: 91 Mb-92 Mb | chr8: 135 Mb-136 Mb |
| chr11: 42 Mb-43 Mb | chr16: 65 Mb-66 Mb | chr21: 14 Mb-15 Mb | chr5: 92 Mb-93 Mb | chr8: 136 Mb-137 Mb |
| chr11: 43 Mb-44 Mb | chr16: 66 Mb-67 Mb | chr21: 15 Mb-16 Mb | chr5: 93 Mb-94 Mb | chr8: 137 Mb-138 Mb |
| chr11: 44 Mb-45 Mb | chr16: 67 Mb-68 Mb | chr21: 16 Mb-17 Mb | chr5: 94 Mb-95 Mb | chr8: 138 Mb-139 Mb |
| chr11: 45 Mb-46 Mb | chr16: 68 Mb-69 Mb | chr21: 17 Mb-18 Mb | chr5: 95 Mb-96 Mb | chr8: 139 Mb-140 Mb |
| chr11: 46 Mb-47 Mb | chr16: 69 Mb-70 Mb | chr21: 18 Mb-19 Mb | chr5: 96 Mb-97 Mb | chr8: 140 Mb-141 Mb |
| chr11: 47 Mb-48 Mb | chr16: 70 Mb-71 Mb | chr21: 19 Mb-20 Mb | chr5: 97 Mb-98 Mb | chr8: 141 Mb-142 Mb |
| chr11: 48 Mb-49 Mb | chr16: 71 Mb-72 Mb | chr21: 20 Mb-21 Mb | chr5: 98 Mb-99 Mb | chr8: 142 Mb-143 Mb |
| chr11: 49 Mb-50 Mb | chr16: 72 Mb-73 Mb | chr21: 21 Mb-22 Mb | chr5: 99 Mb-100 Mb | chr8: 143 Mb-144 Mb |
| chr11: 50 Mb-51 Mb | chr16: 73 Mb-74 Mb | chr21: 22 Mb-23 Mb | chr5: 100 Mb-101 Mb | chr8: 144 Mb-145 Mb |
| chr11: 51 Mb-52 Mb | chr16: 74 Mb-75 Mb | chr21: 23 Mb-24 Mb | chr5: 101 Mb-102 Mb | chr8: 145 Mb-146 Mb |
| chr11: 55 Mb-56 Mb | chr16: 75 Mb-76 Mb | chr21: 24 Mb-25 Mb | chr5: 102 Mb-103 Mb | chr8: 146 Mb-146364022 |
| chr11: 56 Mb-57 Mb | chr16: 76 Mb-77 Mb | chr21: 25 Mb-26 Mb | chr5: 103 Mb-104 Mb | chr9: 0-1 Mb |
| chr11: 57 Mb-58 Mb | chr16: 77 Mb-78 Mb | chr21: 26 Mb-27 Mb | chr5: 104 Mb-105 Mb | chr9: 1 Mb-2 Mb |
| chr11: 58 Mb-59 Mb | chr16: 78 Mb-79 Mb | chr21: 27 Mb-28 Mb | chr5: 105 Mb-106 Mb | chr9: 2 Mb-3 Mb |
| chr11: 59 Mb-60 Mb | chr16: 79 Mb-8 Mb0 | chr21: 28 Mb-29 Mb | chr5: 106 Mb-107 Mb | chr9: 3 Mb-4 Mb |
| chr11: 60 Mb-61 Mb | chr16: 8 Mb0-81 Mb | chr21: 29 Mb-30 Mb | chr5: 107 Mb-108 Mb | chr9: 4 Mb-5 Mb |
| chr11: 61 Mb-62 Mb | chr16: 81 Mb-82 Mb | chr21: 30 Mb-31 Mb | chr5: 108 Mb-109 Mb | chr9: 5 Mb-6 Mb |
| chr11: 62 Mb-63 Mb | chr16: 82 Mb-83 Mb | chr21: 31 Mb-32 Mb | chr5: 109 Mb-110 Mb | chr9: 6 Mb-7 Mb |
| chr11: 63 Mb-64 Mb | chr16: 83 Mb-84 Mb | chr21: 32 Mb-33 Mb | chr5: 110 Mb-111 Mb | chr9: 7 Mb-8 Mb |

TABLE 1-continued

| | | | | |
|---|---|---|---|---|
| chr11: 64 Mb-65 Mb | chr16: 84 Mb-85 Mb | chr21: 33 Mb-34 Mb | chr5: 111 Mb-112 Mb | chr9: 8 Mb-9 Mb |
| chr11: 65 Mb-66 Mb | chr16: 85 Mb-86 Mb | chr21: 34 Mb-35 Mb | chr5: 112 Mb-113 Mb | chr9: 9 Mb-10 Mb |
| chr11: 66 Mb-67 Mb | chr16: 86 Mb-87 Mb | chr21: 35 Mb-36 Mb | chr5: 113 Mb-114 Mb | chr9: 10 Mb-11 Mb |
| chr11: 67 Mb-68 Mb | chr16: 87 Mb-88 Mb | chr21: 36 Mb-37 Mb | chr5: 114 Mb-115 Mb | chr9: 11 Mb-12 Mb |
| chr11: 68 Mb-69 Mb | chr16: 88 Mb-89 Mb | chr21: 37 Mb-38 Mb | chr5: 115 Mb-116 Mb | chr9: 12 Mb-13 Mb |
| chr11: 69 Mb-70 Mb | chr16: 89 Mb-90 Mb | chr21: 38 Mb-39 Mb | chr5: 116 Mb-117 Mb | chr9: 13 Mb-14 Mb |
| chr11: 70 Mb-71 Mb | chr16: 90 Mb-90354753 | chr21: 39 Mb-40 Mb | chr5: 117 Mb-118 Mb | chr9: 14 Mb-15 Mb |
| chr11: 71 Mb-72 Mb | chr17: 0-1 Mb | chr21: 40 Mb-41 Mb | chr5: 118 Mb-119 Mb | chr9: 15 Mb-16 Mb |
| chr11: 72 Mb-73 Mb | chr17: 1 Mb-2 Mb | chr21: 41 Mb-42 Mb | chr5: 119 Mb-120 Mb | chr9: 16 Mb-17 Mb |
| chr11: 73 Mb-74 Mb | chr17: 2 Mb-3 Mb | chr21: 42 Mb-43 Mb | chr5: 120 Mb-121 Mb | chr9: 17 Mb-18 Mb |
| chr11: 74 Mb-75 Mb | chr17: 3 Mb-4 Mb | chr21: 43 Mb-44 Mb | chr5: 121 Mb-122 Mb | chr9: 18 Mb-19 Mb |
| chr11: 75 Mb-76 Mb | chr17: 4 Mb-5 Mb | chr21: 44 Mb-45 Mb | chr5: 122 Mb-123 Mb | chr9: 19 Mb-20 Mb |
| chr11: 76 Mb-77 Mb | chr17: 5 Mb-6 Mb | chr21: 45 Mb-46 Mb | chr5: 123 Mb-124 Mb | chr9: 20 Mb-21 Mb |
| chr11: 77 Mb-78 Mb | chr17: 6 Mb-7 Mb | chr21: 46 Mb-47 Mb | chr5: 124 Mb-125 Mb | chr9: 21 Mb-22 Mb |
| chr11: 78 Mb-79 Mb | chr17: 7 Mb-8 Mb | chr21: 47 Mb-48 Mb | chr5: 125 Mb-126 Mb | chr9: 22 Mb-23 Mb |
| chr11: 79 Mb-8 Mb0 | chr17: 8 Mb-9 Mb | chr21: 48 Mb-48129895 | chr5: 126 Mb-127 Mb | chr9: 23 Mb-24 Mb |
| chr11: 8 Mb0-81 Mb | chr17: 9 Mb-10 Mb | chr22: 16 Mb-17 Mb | chr5: 127 Mb-128 Mb | chr9: 24 Mb-25 Mb |
| chr11: 81 Mb-82 Mb | chr17: 10 Mb-11 Mb | chr22: 17 Mb-18 Mb | chr5: 128 Mb-129 Mb | chr9: 25 Mb-26 Mb |
| chr11: 82 Mb-83 Mb | chr17: 11 Mb-12 Mb | chr22: 18 Mb-19 Mb | chr5: 129 Mb-130 Mb | chr9: 26 Mb-27 Mb |
| chr11: 83 Mb-84 Mb | chr17: 12 Mb-13 Mb | chr22: 19 Mb-20 Mb | chr5: 130 Mb-131 Mb | chr9: 27 Mb-28 Mb |
| chr11: 84 Mb-85 Mb | chr17: 13 Mb-14 Mb | chr22: 20 Mb-21 Mb | chr5: 131 Mb-132 Mb | chr9: 28 Mb-29 Mb |
| chr11: 85 Mb-86 Mb | chr17: 14 Mb-15 Mb | chr22: 21 Mb-22 Mb | chr5: 132 Mb-133 Mb | chr9: 29 Mb-30 Mb |
| chr11: 86 Mb-87 Mb | chr17: 15 Mb-16 Mb | chr22: 22 Mb-23 Mb | chr5: 133 Mb-134 Mb | chr9: 30 Mb-31 Mb |
| chr11: 87 Mb-88 Mb | chr17: 16 Mb-17 Mb | chr22: 23 Mb-24 Mb | chr5: 134 Mb-135 Mb | chr9: 31 Mb-32 Mb |
| chr11: 88 Mb-89 Mb | chr17: 17 Mb-18 Mb | chr22: 24 Mb-25 Mb | chr5: 135 Mb-136 Mb | chr9: 32 Mb-33 Mb |
| chr11: 89 Mb-90 Mb | chr17: 18 Mb-19 Mb | chr22: 25 Mb-26 Mb | chr5: 136 Mb-137 Mb | chr9: 33 Mb-34 Mb |
| chr11: 90 Mb-91 Mb | chr17: 19 Mb-20 Mb | chr22: 26 Mb-27 Mb | chr5: 137 Mb-138 Mb | chr9: 34 Mb-35 Mb |
| chr11: 91 Mb-92 Mb | chr17: 20 Mb-21 Mb | chr22: 27 Mb-28 Mb | chr5: 138 Mb-139 Mb | chr9: 35 Mb-36 Mb |
| chr11: 92 Mb-93 Mb | chr17: 21 Mb-22 Mb | chr22: 28 Mb-29 Mb | chr5: 139 Mb-140 Mb | chr9: 36 Mb-37 Mb |
| chr11: 93 Mb-94 Mb | chr17: 22 Mb-23 Mb | chr22: 29 Mb-30 Mb | chr5: 140 Mb-141 Mb | chr9: 37 Mb-38 Mb |
| chr11: 94 Mb-95 Mb | chr17: 25 Mb-26 Mb | chr22: 30 Mb-31 Mb | chr5: 141 Mb-142 Mb | chr9: 38 Mb-39 Mb |
| chr11: 95 Mb-96 Mb | chr17: 26 Mb-27 Mb | chr22: 31 Mb-32 Mb | chr5: 142 Mb-143 Mb | chr9: 39 Mb-40 Mb |
| chr11: 96 Mb-97 Mb | chr17: 27 Mb-28 Mb | chr22: 32 Mb-33 Mb | chr5: 143 Mb-144 Mb | chr9: 40 Mb-41 Mb |
| chr11: 97 Mb-98 Mb | chr17: 28 Mb-29 Mb | chr22: 33 Mb-34 Mb | chr5: 144 Mb-145 Mb | chr9: 41 Mb-42 Mb |
| chr11: 98 Mb-99 Mb | chr17: 29 Mb-30 Mb | chr22: 34 Mb-35 Mb | chr5: 145 Mb-146 Mb | chr9: 42 Mb-43 Mb |
| chr11: 99 Mb-100 Mb | chr17: 30 Mb-31 Mb | chr22: 35 Mb-36 Mb | chr5: 146 Mb-147 Mb | chr9: 43 Mb-44 Mb |
| chr11: 100 Mb-101 Mb | chr17: 31 Mb-32 Mb | chr22: 36 Mb-37 Mb | chr5: 147 Mb-148 Mb | chr9: 44 Mb-45 Mb |
| chr11: 101 Mb-102 Mb | chr17: 32 Mb-33 Mb | chr22: 37 Mb-38 Mb | chr5: 148 Mb-149 Mb | chr9: 45 Mb-46 Mb |
| chr11: 102 Mb-103 Mb | chr17: 33 Mb-34 Mb | chr22: 38 Mb-39 Mb | chr5: 149 Mb-150 Mb | chr9: 46 Mb-47 Mb |
| chr11: 103 Mb-104 Mb | chr17: 34 Mb-35 Mb | chr22: 39 Mb-40 Mb | chr5: 150 Mb-151 Mb | chr9: 47 Mb-48 Mb |
| chr11: 104 Mb-105 Mb | chr17: 35 Mb-36 Mb | chr22: 40 Mb-41 Mb | chr5: 151 Mb-152 Mb | chr9: 65 Mb-66 Mb |
| chr11: 105 Mb-106 Mb | chr17: 36 Mb-37 Mb | chr22: 41 Mb-42 Mb | chr5: 152 Mb-153 Mb | chr9: 66 Mb-67 Mb |
| chr11: 106 Mb-107 Mb | chr17: 37 Mb-38 Mb | chr22: 42 Mb-43 Mb | chr5: 153 Mb-154 Mb | chr9: 67 Mb-68 Mb |
| chr11: 107 Mb-108 Mb | chr17: 38 Mb-39 Mb | chr22: 43 Mb-44 Mb | chr5: 154 Mb-155 Mb | chr9: 68 Mb-69 Mb |
| chr11: 108 Mb-109 Mb | chr17: 39 Mb-40 Mb | chr22: 44 Mb-45 Mb | chr5: 155 Mb-156 Mb | chr9: 69 Mb-70 Mb |
| chr11: 109 Mb-110 Mb | chr17: 40 Mb-41 Mb | chr22: 45 Mb-46 Mb | chr5: 156 Mb-157 Mb | chr9: 70 Mb-71 Mb |
| chr11: 110 Mb-111 Mb | chr17: 41 Mb-42 Mb | chr22: 46 Mb-47 Mb | chr5: 157 Mb-158 Mb | chr9: 71 Mb-72 Mb |
| chr11: 111 Mb-112 Mb | chr17: 42 Mb-43 Mb | chr22: 47 Mb-48 Mb | chr5: 158 Mb-159 Mb | chr9: 72 Mb-73 Mb |
| chr11: 112 Mb-113 Mb | chr17: 43 Mb-44 Mb | chr22: 48 Mb-49 Mb | chr5: 159 Mb-160 Mb | chr9: 73 Mb-74 Mb |
| chr11: 113 Mb-114 Mb | chr17: 44 Mb-45 Mb | chr22: 49 Mb-50 Mb | chr5: 160 Mb-161 Mb | chr9: 74 Mb-75 Mb |
| chr11: 114 Mb-115 Mb | chr17: 45 Mb-46 Mb | chr22: 50 Mb-51 Mb | chr5: 161 Mb-162 Mb | chr9: 75 Mb-76 Mb |
| chr11: 115 Mb-116 Mb | chr17: 46 Mb-47 Mb | chr22: 51 Mb-51304566 | chr5: 162 Mb-163 Mb | chr9: 76 Mb-77 Mb |
| chr11: 116 Mb-117 Mb | chr17: 47 Mb-48 Mb | chr3: 0-1 Mb | chr5: 163 Mb-164 Mb | chr9: 77 Mb-78 Mb |
| chr11: 117 Mb-118 Mb | chr17: 48 Mb-49 Mb | chr3: 1 Mb-2 Mb | chr5: 164 Mb-165 Mb | chr9: 78 Mb-79 Mb |
| chr11: 118 Mb-119 Mb | chr17: 49 Mb-50 Mb | chr3: 2 Mb-3 Mb | chr5: 165 Mb-166 Mb | chr9: 79 Mb-8 Mb0 |
| chr11: 119 Mb-120 Mb | chr17: 50 Mb-51 Mb | chr3: 3 Mb-4 Mb | chr5: 166 Mb-167 Mb | chr9: 8 Mb0-81 Mb |
| chr11: 120 Mb-121 Mb | chr17: 51 Mb-52 Mb | chr3: 4 Mb-5 Mb | chr5: 167 Mb-168 Mb | chr9: 81 Mb-82 Mb |
| chr11: 121 Mb-122 Mb | chr17: 52 Mb-53 Mb | chr3: 5 Mb-6 Mb | chr5: 168 Mb-169 Mb | chr9: 82 Mb-83 Mb |
| chr11: 122 Mb-123 Mb | chr17: 53 Mb-54 Mb | chr3: 6 Mb-7 Mb | chr5: 169 Mb-170 Mb | chr9: 83 Mb-84 Mb |
| chr11: 123 Mb-124 Mb | chr17: 54 Mb-55 Mb | chr3: 7 Mb-8 Mb | chr5: 170 Mb-171 Mb | chr9: 84 Mb-85 Mb |
| chr11: 124 Mb-125 Mb | chr17: 55 Mb-56 Mb | chr3: 8 Mb-9 Mb | chr5: 171 Mb-172 Mb | chr9: 85 Mb-86 Mb |
| chr11: 125 Mb-126 Mb | chr17: 56 Mb-57 Mb | chr3: 9 Mb-10 Mb | chr5: 172 Mb-173 Mb | chr9: 86 Mb-87 Mb |
| chr11: 126 Mb-127 Mb | chr17: 57 Mb-58 Mb | chr3: 10 Mb-11 Mb | chr5: 173 Mb-174 Mb | chr9: 87 Mb-88 Mb |
| chr11: 127 Mb-128 Mb | chr17: 58 Mb-59 Mb | chr3: 11 Mb-12 Mb | chr5: 174 Mb-175 Mb | chr9: 88 Mb-89 Mb |
| chr11: 128 Mb-129 Mb | chr17: 59 Mb-60 Mb | chr3: 12 Mb-13 Mb | chr5: 175 Mb-176 Mb | chr9: 89 Mb-90 Mb |
| chr11: 129 Mb-130 Mb | chr17: 60 Mb-61 Mb | chr3: 13 Mb-14 Mb | chr5: 176 Mb-177 Mb | chr9: 90 Mb-91 Mb |
| chr11: 130 Mb-131 Mb | chr17: 61 Mb-62 Mb | chr3: 14 Mb-15 Mb | chr5: 177 Mb-178 Mb | chr9: 91 Mb-92 Mb |
| chr11: 131 Mb-132 Mb | chr17: 62 Mb-63 Mb | chr3: 15 Mb-16 Mb | chr5: 178 Mb-179 Mb | chr9: 92 Mb-93 Mb |
| chr11: 132 Mb-133 Mb | chr17: 63 Mb-64 Mb | chr3: 16 Mb-17 Mb | chr5: 179 Mb-18 Mb0 | chr9: 93 Mb-94 Mb |
| chr11: 133 Mb-134 Mb | chr17: 64 Mb-65 Mb | chr3: 17 Mb-18 Mb | chr5: 18 Mb0-180915260 | chr9: 94 Mb-95 Mb |
| chr11: 134 Mb-135 Mb | chr17: 65 Mb-66 Mb | chr3: 18 Mb-19 Mb | chr6: 0-1 Mb | chr9: 95 Mb-96 Mb |
| chr12: 0-1 Mb | chr17: 66 Mb-67 Mb | chr3: 19 Mb-20 Mb | chr6: 1 Mb-2 Mb | chr9: 96 Mb-97 Mb |
| chr12: 1 Mb-2 Mb | chr17: 67 Mb-68 Mb | chr3: 20 Mb-21 Mb | chr6: 2 Mb-3 Mb | chr9: 97 Mb-98 Mb |
| chr12: 2 Mb-3 Mb | chr17: 68 Mb-69 Mb | chr3: 21 Mb-22 Mb | chr6: 3 Mb-4 Mb | chr9: 98 Mb-99 Mb |
| chr12: 3 Mb-4 Mb | chr17: 69 Mb-70 Mb | chr3: 22 Mb-23 Mb | chr6: 4 Mb-5 Mb | chr9: 99 Mb-100 Mb |
| chr12: 4 Mb-5 Mb | chr17: 70 Mb-71 Mb | chr3: 23 Mb-24 Mb | chr6: 5 Mb-6 Mb | chr9: 100 Mb-101 Mb |
| chr12: 5 Mb-6 Mb | chr17: 71 Mb-72 Mb | chr3: 24 Mb-25 Mb | chr6: 6 Mb-7 Mb | chr9: 101 Mb-102 Mb |
| chr12: 6 Mb-7 Mb | chr17: 72 Mb-73 Mb | chr3: 25 Mb-26 Mb | chr6: 7 Mb-8 Mb | chr9: 102 Mb-103 Mb |
| chr12: 7 Mb-8 Mb | chr17: 73 Mb-74 Mb | chr3: 26 Mb-27 Mb | chr6: 8 Mb-9 Mb | chr9: 103 Mb-104 Mb |
| chr12: 8 Mb-9 Mb | chr17: 74 Mb-75 Mb | chr3: 27 Mb-28 Mb | chr6: 9 Mb-10 Mb | chr9: 104 Mb-105 Mb |

TABLE 1-continued

| | | | | |
|---|---|---|---|---|
| chr12: 9 Mb-10 Mb | chr17: 75 Mb-76 Mb | chr3: 28 Mb-29 Mb | chr6: 10 Mb-11 Mb | chr9: 105 Mb-106 Mb |
| chr12: 10 Mb-11 Mb | chr17: 76 Mb-77 Mb | chr3: 29 Mb-30 Mb | chr6: 11 Mb-12 Mb | chr9: 106 Mb-107 Mb |
| chr12: 11 Mb-12 Mb | chr17: 77 Mb-78 Mb | chr3: 30 Mb-31 Mb | chr6: 12 Mb-13 Mb | chr9: 107 Mb-108 Mb |
| chr12: 12 Mb-13 Mb | chr17: 78 Mb-79 Mb | chr3: 31 Mb-32 Mb | chr6: 13 Mb-14 Mb | chr9: 108 Mb-109 Mb |
| chr12: 13 Mb-14 Mb | chr17: 79 Mb-8 Mb0 | chr3: 32 Mb-33 Mb | chr6: 14 Mb-15 Mb | chr9: 109 Mb-110 Mb |
| chr12: 14 Mb-15 Mb | chr17: 8 Mb0-81 Mb | chr3: 33 Mb-34 Mb | chr6: 15 Mb-16 Mb | chr9: 110 Mb-111 Mb |
| chr12: 15 Mb-16 Mb | chr17: 81 Mb-81195210 | chr3: 34 Mb-35 Mb | chr6: 16 Mb-17 Mb | chr9: 111 Mb-112 Mb |
| chr12: 16 Mb-17 Mb | chr18: 0-1 Mb | chr3: 35 Mb-36 Mb | chr6: 17 Mb-18 Mb | chr9: 112 Mb-113 Mb |
| chr12: 17 Mb-18 Mb | chr18: 1 Mb-2 Mb | chr3: 36 Mb-37 Mb | chr6: 18 Mb-19 Mb | chr9: 113 Mb-114 Mb |
| chr12: 18 Mb-19 Mb | chr18: 2 Mb-3 Mb | chr3: 37 Mb-38 Mb | chr6: 19 Mb-20 Mb | chr9: 114 Mb-115 Mb |
| chr12: 19 Mb-20 Mb | chr18: 3 Mb-4 Mb | chr3: 38 Mb-39 Mb | chr6: 20 Mb-21 Mb | chr9: 115 Mb-116 Mb |
| chr12: 20 Mb-21 Mb | chr18: 4 Mb-5 Mb | chr3: 39 Mb-40 Mb | chr6: 21 Mb-22 Mb | chr9: 116 Mb-117 Mb |
| chr12: 21 Mb-22 Mb | chr18: 5 Mb-6 Mb | chr3: 40 Mb-41 Mb | chr6: 22 Mb-23 Mb | chr9: 117 Mb-118 Mb |
| chr12: 22 Mb-23 Mb | chr18: 6 Mb-7 Mb | chr3: 41 Mb-42 Mb | chr6: 23 Mb-24 Mb | chr9: 118 Mb-119 Mb |
| chr12: 23 Mb-24 Mb | chr18: 7 Mb-8 Mb | chr3: 42 Mb-43 Mb | chr6: 24 Mb-25 Mb | chr9: 119 Mb-120 Mb |
| chr12: 24 Mb-25 Mb | chr18: 8 Mb-9 Mb | chr3: 43 Mb-44 Mb | chr6: 25 Mb-26 Mb | chr9: 120 Mb-121 Mb |
| chr12: 25 Mb-26 Mb | chr18: 9 Mb-10 Mb | chr3: 44 Mb-45 Mb | chr6: 26 Mb-27 Mb | chr9: 121 Mb-122 Mb |
| chr12: 26 Mb-27 Mb | chr18: 10 Mb-11 Mb | chr3: 45 Mb-46 Mb | chr6: 27 Mb-28 Mb | chr9: 122 Mb-123 Mb |
| chr12: 27 Mb-28 Mb | chr18: 11 Mb-12 Mb | chr3: 46 Mb-47 Mb | chr6: 28 Mb-29 Mb | chr9: 123 Mb-124 Mb |
| chr12: 28 Mb-29 Mb | chr18: 12 Mb-13 Mb | chr3: 47 Mb-48 Mb | chr6: 29 Mb-30 Mb | chr9: 124 Mb-125 Mb |
| chr12: 29 Mb-30 Mb | chr18: 13 Mb-14 Mb | chr3: 48 Mb-49 Mb | chr6: 31 Mb-32 Mb | chr9: 125 Mb-126 Mb |
| chr12: 30 Mb-31 Mb | chr18: 14 Mb-15 Mb | chr3: 49 Mb-50 Mb | chr6: 32 Mb-33 Mb | chr9: 126 Mb-127 Mb |
| chr12: 31 Mb-32 Mb | chr18: 15 Mb-16 Mb | chr3: 50 Mb-51 Mb | chr6: 33 Mb-34 Mb | chr9: 127 Mb-128 Mb |
| chr12: 32 Mb-33 Mb | chr18: 18 Mb-19 Mb | chr3: 51 Mb-52 Mb | chr6: 34 Mb-35 Mb | chr9: 128 Mb-129 Mb |
| chr12: 33 Mb-34 Mb | chr18: 19 Mb-20 Mb | chr3: 52 Mb-53 Mb | chr6: 35 Mb-36 Mb | chr9: 129 Mb-130 Mb |
| chr12: 34 Mb-35 Mb | chr18: 20 Mb-21 Mb | chr3: 53 Mb-54 Mb | chr6: 36 Mb-37 Mb | chr9: 130 Mb-131 Mb |
| chr12: 37 Mb-38 Mb | chr18: 21 Mb-22 Mb | chr3: 54 Mb-55 Mb | chr6: 37 Mb-38 Mb | chr9: 131 Mb-132 Mb |
| chr12: 38 Mb-39 Mb | chr18: 22 Mb-23 Mb | chr3: 55 Mb-56 Mb | chr6: 38 Mb-39 Mb | chr9: 132 Mb-133 Mb |
| chr12: 39 Mb-40 Mb | chr18: 23 Mb-24 Mb | chr3: 56 Mb-57 Mb | chr6: 39 Mb-40 Mb | chr9: 133 Mb-134 Mb |
| chr12: 40 Mb-41 Mb | chr18: 24 Mb-25 Mb | chr3: 57 Mb-58 Mb | chr6: 40 Mb-41 Mb | chr9: 134 Mb-135 Mb |
| chr12: 41 Mb-42 Mb | chr18: 25 Mb-26 Mb | chr3: 58 Mb-59 Mb | chr6: 41 Mb-42 Mb | chr9: 135 Mb-136 Mb |
| chr12: 42 Mb-43 Mb | chr18: 26 Mb-27 Mb | chr3: 59 Mb-60 Mb | chr6: 42 Mb-43 Mb | chr9: 136 Mb-137 Mb |
| chr12: 43 Mb-44 Mb | chr18: 27 Mb-28 Mb | chr3: 60 Mb-61 Mb | chr6: 43 Mb-44 Mb | chr9: 137 Mb-138 Mb |
| chr12: 44 Mb-45 Mb | chr18: 28 Mb-29 Mb | chr3: 61 Mb-62 Mb | chr6: 44 Mb-45 Mb | chr9: 138 Mb-139 Mb |
| chr12: 45 Mb-46 Mb | chr18: 29 Mb-30 Mb | chr3: 62 Mb-63 Mb | chr6: 45 Mb-46 Mb | chr9: 139 Mb-140 Mb |
| chr12: 46 Mb-47 Mb | chr18: 30 Mb-31 Mb | chr3: 63 Mb-64 Mb | chr6: 46 Mb-47 Mb | chr9: 140 Mb-141 Mb |
| chr12: 47 Mb-48 Mb | chr18: 31 Mb-32 Mb | chr3: 64 Mb-65 Mb | chr6: 47 Mb-48 Mb | chr9: 141 Mb-141213431 |
| chr12: 48 Mb-49 Mb | chr18: 32 Mb-33 Mb | chr3: 65 Mb-66 Mb | | |
| chr12: 49 Mb-50 Mb | chr18: 33 Mb-34 Mb | chr3: 66 Mb-67 Mb | | |
| chr12: 50 Mb-51 Mb | chr18: 34 Mb-35 Mb | chr3: 67 Mb-68 Mb | | |
| chr12: 51 Mb-52 Mb | chr18: 35 Mb-36 Mb | chr3: 68 Mb-69 Mb. | | |

8. The method according to claim 1, wherein the calculating the frequency of mutation signature of extracted cancer-specific single nucleotide variants in step (e) is performed through a method comprising:

(e-i) calculating a number of mutations depending on a type of mutation below:
  (1) a mutation in which cytosine (C) is substituted with thymine (T), adenine (A), or guanine (G),
  (2) a mutation in which thymine is substituted with cytosine, adenine, or guanine,
  (3) a mutation in which the mutation (1) or (2) further comprises a base in a 5' direction thereof,
  (4) a mutation in which the mutation (1) or (2) further comprises a base in a 3' direction thereof, and
  (5) a mutation in which a mutation in which adenine, guanine, cytosine, and thymine are substituted with different bases further comprises a base in each of 5' and 3' directions thereof; and (e-ii) normalizing a sum of the calculated number of mutations by dividing the sum of the calculated number of mutations by a total number of all mutations occurring in all bases.

9. The method according to claim 8, wherein the mutation signature is at least one selected from among mutations shown in Table 2 below

TABLE 2

| | | | | | | | | | |
|---|---|---|---|---|---|---|---|---|---|
| sig-one | C>A | sig-rev | 3CA:C>A | sig-tri | TCG:C>A | sig-tri | TCA:C>T | sig-tri | ATG:T>C |
| sig-one | C>G | sig-rev | 3CT:C>A | sig-tri | TCC:C>A | sig-tri | TCT:C>T | sig-tri | ATC:T>C |
| sig-one | C>T | sig-rev | 3CG:C>A | sig-tri | GCA:C>A | sig-tri | TCG:C>T | sig-tri | TTA:T>C |
| sig-one | T>A | sig-rev | 3CC:C>A | sig-tri | GCT:C>A | sig-tri | TCC:C>T | sig-tri | TTT:T>C |
| sig-one | T>C | sig-rev | 3CA:C>G | sig-tri | GCG:C>A | sig-tri | GCA:C>T | sig-tri | TTG:T>C |
| sig-one | T>G | sig-rev | 3CT:C>G | sig-tri | GCC:C>A | sig-tri | GCT:C>T | sig-tri | TTC:T>C |
| sig-for | 5AC:C>A | sig-rev | 3CG:C>G | sig-tri | CCA:C>A | sig-tri | GCG:C>T | sig-tri | GTA:T>C |
| sig-for | 5TC:C>A | sig-rev | 3CC:C>G | sig-tri | CCT:C>A | sig-tri | GCC:C>T | sig-tri | GTT:T>C |

TABLE 2-continued

| | | | | | | | | | |
|---|---|---|---|---|---|---|---|---|---|
| sig-for | 5GC:C>A | sig-rev | 3CA:C>T | sig-tri | CCG:C>A | sig-tri | CCA:C>T | sig-tri | GTG:T>C |
| sig-for | 5CC:C>A | sig-rev | 3CT:C>T | sig-tri | CCC:C>A | sig-tri | CCT:C>T | sig-tri | GTC:T>C |
| sig-for | 5AC:C>G | sig-rev | 3CG:C>T | sig-tri | ACA:C>G | sig-tri | CCG:C>T | sig-tri | CTA:T>C |
| sig-for | 5TC:C>G | sig-rev | 3CC:C>T | sig-tri | ACT:C>G | sig-tri | CCC:C>T | sig-tri | CTT:T>C |
| sig-for | 5GC:C>G | sig-rev | 3TA:T>A | sig-tri | ACG:C>G | sig-tri | ATA:T>A | sig-tri | CTG:T>C |
| sig-for | 5CC:C>G | sig-rev | 3TT:T>A | sig-tri | ACC:C>G | sig-tri | ATT:T>A | sig-tri | CTC:T>C |
| sig-for | 5AC:C>T | sig-rev | 3TG:T>A | sig-tri | TCA:C>G | sig-tri | ATG:T>A | sig-tri | ATA:T>G |
| sig-for | 5TC:C>T | sig-rev | 3TC:T>A | sig-tri | TCT:C>G | sig-tri | ATC:T>A | sig-tri | ATT:T>G |
| sig-for | 5GC:C>T | sig-rev | 3TA:T>C | sig-tri | TCG:C>G | sig-tri | TTA:T>A | sig-tri | ATG:T>G |
| sig-for | 5CC:C>T | sig-rev | 3TT:T>C | sig-tri | TCC:C>G | sig-tri | TTT:T>A | sig-tri | ATC:T>G |
| sig-for | 5AT:T>A | sig-rev | 3TG:T>C | sig-tri | GCA:C>G | sig-tri | TTG:T>A | sig-tri | TTA:T>G |
| sig-for | 5TT:T>A | sig-rev | 3TC:T>C | sig-tri | GCT:C>G | sig-tri | TTC:T>A | sig-tri | TTT:T>G |
| sig-for | 5GT:T>A | sig-rev | 3TA:T>G | sig-tri | GCG:C>G | sig-tri | GTA:T>A | sig-tri | TTG:T>G |
| sig-for | 5CT:T>A | sig-rev | 3TT:T>G | sig-tri | GCC:C>G | sig-tri | GTT:T>A | sig-tri | TTC:T>G |
| sig-for | 5AT:T>C | sig-rev | 3TG:T>G | sig-tri | CCA:C>G | sig-tri | GTG:T>A | sig-tri | GTA:T>G |
| sig-for | 5TT:T>C | sig-rev | 3TC:T>G | sig-tri | CCT:C>G | sig-tri | GTC:T>A | sig-tri | GTT:T>G |
| sig-for | 5GT:T>C | sig-tri | ACA:C>A | sig-tri | CCG:C>G | sig-tri | CTA:T>A | sig-tri | GTG:T>G |
| sig-for | 5CT:T>C | sig-tri | ACT:C>A | sig-tri | CCC:C>G | sig-tri | CTT:T>A | sig-tri | GTC:T>G |
| sig-for | 5AT:T>G | sig-tri | ACG:C>A | sig-tri | ACA:C>T | sig-tri | CTG:T>A | sig-tri | CTA:T>G |
| sig-for | 5TT:T>G | sig-tri | ACC:C>A | sig-tri | ACT:C>T | sig-tri | CTC:T>A | sig-tri | CTT:T>G |
| sig-for | 5GT:T>G | sig-tri | TCA:C>A | sig-tri | ACG:C>T | sig-tri | ATA:T>C | sig-tri | CTG:T>G |
| sig-for | 5CT:T>G | sig-tri | TCT:C>A | sig-tri | ACC:C>T | sig-tri | ATT:T>C | sig-tri. | CTC:T>G |

10. The method according to claim 1, wherein the reference value in step (i) is 0.5, and a case in which the reference value is 0.5 or more is determined to be cancer.

11. The method according to claim 1, further comprising:
(i) predicting a type of cancer by inputting the combined RMD and frequency of mutation signature of step (f) into a second artificial intelligence model trained to classify types of cancer, wherein the artificial intelligence model transforms the combined RMD and frequency of mutation signature of step (f) into an output value and compares output values.

12. The method according to claim 11, wherein the comparing the output values in step (i) is performed through a method comprising determining a type of cancer showing a highest value among the output values to be cancer of the sample.

13. The method according to claim 11, wherein, when the second artificial intelligence model is a DNN and multi-class classification is trained, a loss function is categorical cross-entropy represented by Equation 2 below:

$$CCE = -\frac{1}{N}\sum_{i=0}^{N}\sum_{j=0}^{J} y_j \cdot \log(\hat{y}_j) + (1-y_j) \cdot \log(1-\hat{y}_j) \quad \text{Equation 2}$$

wherein N is a total number of samples, J is a total number of classes, $y_j$ is a value representing an actual class of a sample, in which if the actual class is j, it is represented as 1, and if the actual class is not j, it is represented as 0, and ŷj is a predicted probability value that the sample belongs to class j and is a predicted probability value that the closer to 1, the higher the probability of belonging to the class.

14. The method according to claim 1, wherein the artificial intelligence model in step (g) is selected from the group consisting of a convolutional neural network (CNN), a deep neural network (DNN), a recurrent neural network (RNN), and an autoencoder.

15. An apparatus for measuring regional mutation density (RMD) and a frequency of mutation signature, comprising:
a decoding unit configured to decode sequence read information by extracting nucleic acids from a biological sample, the sequence read information comprising reads of 5 to 5,000 bp, and comprising at least 5,000 reads, the extracted nucleic acids comprising cell free DNA (cfDNA);
an alignment unit configured to align the decoded sequence read information to a reference genome from a reference genome database to generate aligned sequences;
a mutation detection unit configured to extract cancer-specific single nucleotide variants, wherein the extracting step is performed by detecting single nucleotide variants in the aligned sequences and performing filtering based on the aligned sequences, the filtering comprising removing artifacts and germline mutations generated during the sequencing process;
a single nucleotide variant distribution calculation unit configured to divide a reference genome into predetermined chromosomal bins and calculate a RMD of extracted cancer-specific single nucleotide variants in each bin;
a mutation frequency calculation unit configured to calculate a frequency of 150 mutation signatures of the extracted cancer-specific single nucleotide variants, the 150 mutation signature features comprising:
  (i) 6 basic mutation signatures (C>A, C>G, C>T, T>A, T>C, and T>G);
  (ii.) 24 (4×6) mutation signatures for a base mutation in a 5' direction;
  (iii.) 24 (6×4) mutation signatures for a base mutation in a 3' direction;
  (iv.) 96 (4×6×4) mutation signatures for a base mutation in a 5' direction and a base mutation in a 3' direction;
a combination unit configured to combine the RMD of extracted cancer-specific single nucleotide variants and the frequency of mutation signature of extracted cancer-specific single nucleotide variants;
a cancer diagnosis unit configured to determine whether cancer is present or not by inputting the combined RMD of extracted cancer-specific single nucleotide variants and the mutation frequency thereof into an artificial intelligence model trained to perform cancer diagnosis, wherein the artificial intelligence model transforms the combined RMD and frequency of mutation signature into an output value, that is a probability value between 0 and 1 and compares the output value with a reference value, that is a value between 0 and 1 capable of determining the presence of cancer when compared to the output value; and
determining the presence of cancer when the output value exceeds the reference value;
training the artificial intelligence model for cancer diagnosis using a binary cross-entropy loss function represented by Equation 1 below:

$$BCE = -\frac{1}{N}\sum_{i=0}^{N} y_i \cdot \log(\hat{y}_i) + (1 - y_i) \cdot \log(1 - \hat{y}_i)$$ Equation 1 wherein N is a total number of samples, $\hat{y}_i$ is a probability value predicted by the model that an $i^{th}$ input value is close to class 1, and $y^i$ is an actual class of the $i^{th}$ input value;
wherein the training comprises:
  hyper-parameter tuning using Bayesian optimization;
  inputting regional mutation density and mutation signature data divided into training, validation, and test datasets into the artificial intelligence model;
  performing cancer detection on each of the test datasets using the artificial intelligence model, allowing each dataset to serve once as the test dataset; and
  evaluating model performance using a prediction probability when the entire sample was the test dataset; and
a cancer-type prediction unit configured to predict a type of cancer by inputting the combined RMD of extracted cancer-specific single nucleotide variants of the sample determined to be cancer and the mutation frequency thereof to a second artificial intelligence model trained to classify types of cancer, wherein the second artificial intelligence model transforms the combined RMD and frequency of mutation signature into an output value and compares output values.

16. A non-transitory computer-readable storage medium comprising instructions configured to be executed by a processor for measuring regional mutation density (RMD) and a frequency of mutation signature, by:
a) extracting nucleic acids from a biological sample to obtain sequence read information, the sequence read information comprising reads of 5 to 5,000 bp and comprising at least 5,000 reads, the extracted nucleic acids comprising cell free DNA (cfDNA);
b) aligning the obtained sequence read information to a reference genome from a reference genome database to generate aligned sequence read information;
c) extracting cancer-specific single nucleotide variants, wherein the extracting step is performed by detecting single nucleotide variants in the aligned sequence read information and performing filtering based on the aligned sequence read information, the filtering comprising removing artifacts and germline mutations generated during the sequencing process;
d) dividing the reference genome into predetermined chromosomal bins and calculating a RMD of extracted cancer-specific single nucleotide variants from step (c) in each bin;
e) calculating a frequency of 150 mutation signatures of the extracted cancer-specific single nucleotide variants from step (c), the 150 mutation signature features comprising:
  (i) 6 basic mutation signatures (C>A, C>G, C>T, T>A, T>C, and T>G);
  (ii.) 24 (4×6) mutation signatures for a base mutation in a 5' direction;
  (iii.) 24 (6×4) mutation signatures for a base mutation in a 3' direction;
  (iv.) 96 (4×6×4) mutation signatures for a base mutation in a 5' direction and a base mutation in a 3' direction;
f) combining the RMD of extracted cancer-specific single nucleotide variants calculated in step (d) and the frequency of mutation signature of extracted cancer-specific single nucleotide variants calculated in step (e);
g) inputting the combined RMD and frequency of mutation signature of step (f) into a first artificial intelligence model trained to perform cancer diagnosis;
h) determining an output value using the first artificial intelligence model, wherein the first artificial intelligence model transforms the combined RMD and frequency of mutation signature of step (f) into an output value, that is a probability value between 0 and 1;
i) determining whether cancer is present or not by comparing the output value with a reference value, that is a value between 0 and 1 capable of determining the presence of cancer when compared to the output value; and
determining the presence of cancer when the output value exceeds the reference value;
training the artificial intelligence model for cancer diagnosis using a binary cross-entropy loss function represented by Equation 1 below:

$$BCE = -\frac{1}{N}\sum_{i=0}^{N} y_i \cdot \log(\hat{y}_i) + (1 - y_i) \cdot \log(1 - \hat{y}_i)$$ Equation 1 wherein N is a total number of samples, $\hat{y}_i$ is a probability value predicted by the model that an $i^{th}$ input value is close to class 1, and $y^i$ is an actual class of the $i^{th}$ input value;
   wherein the training comprises:
      hyper-parameter tuning using Bayesian optimization;
      inputting regional mutation density and mutation signature data divided into training, validation, and test datasets into the artificial intelligence model;
      performing cancer detection on each of the test datasets using the artificial intelligence model, allowing each dataset to serve once as the test dataset; and
      evaluating model performance using a prediction probability when the entire sample was the test dataset;
j) inputting the combined RMD and frequency of mutation signature of step (f) into a second artificial intelligence model trained to classify types of cancer;
k) determining an output value using the second artificial intelligence model, wherein the second artificial intelligence model transforms the combined RMD and mutation signature of step (f) into an output value; and
l. Predicting a type of cancer by comparing output values.

* * * * *

UNITED STATES PATENT AND TRADEMARK OFFICE
CERTIFICATE OF CORRECTION

| | | |
|---|---|---|
| PATENT NO. | : 12,331,364 B2 | Page 1 of 2 |
| APPLICATION NO. | : 18/169750 | |
| DATED | : June 17, 2025 | |
| INVENTOR(S) | : JungKyoon Choi et al. | |

It is certified that error appears in the above-identified patent and that said Letters Patent is hereby corrected as shown below:

On the Title Page

Column 2, Line 21, under Other Publications, delete ""Sequencing technlogies—the" and insert --"Sequencing technologies—the--.

Column 2, Line 9, under Abstract, delete "a trained s: artificial" and insert --a trained artificial--.

In the Specification

In Column 7, Line 23, delete "CA; SOLID Sequencer)," and insert --CA; SOLiD Sequencer),--.

In Column 7, Line 32, delete "Detection (SOLID) system," and insert --Detection (SOLiD) system,--.

In Column 10, Line 35 (Approx.), delete "and ŷj is" and insert --and $\hat{y}_j$ is--.

In the Claims

In Column 32, Claim 1, Line 59, delete "comprising: (i) 6" and insert --comprising: (i.) 6--.

In Column 49, Claim 11, Line 44, delete "comprising: (i) predicting" and insert --comprising: (j) predicting--.

In Column 49, Claim 12, Line 52, delete "step (i) is" and insert --step (j) is--.

In Column 50, Claim 13, Line 42 (Approx.), delete "and ŷj is" and insert --and $\hat{y}_j$ is--.

In Column 51, Claim 15, Line 13, delete "comprising: (i) 6" and insert --comprising: (i.) 6--.

Signed and Sealed this
Thirtieth Day of September, 2025

John A. Squires
*Director of the United States Patent and Trademark Office*

CERTIFICATE OF CORRECTION (continued)
U.S. Pat. No. 12,331,364 B2

In Column 52, Claim 16, Line 31 (Approx.), delete "comprising: (i) 6" and insert --comprising: (i.) 6--.

In Column 53, Claim 16, Line 21, delete "and 1. Predicting a" and insert --and l) predicting a--.